(12) United States Patent
Schmidt

(10) Patent No.: US 11,667,679 B2
(45) Date of Patent: Jun. 6, 2023

(54) STREPTAVIDIN MUTEINS AND METHODS OF USING THEM

(71) Applicant: IBA LIFESCIENCES GMBH, Goettingen (DE)

(72) Inventor: Thomas Schmidt, Adelebsen (DE)

(73) Assignee: IBA LIFESCIENCES GMBH, Goettingen (DE)

( * ) Notice: Subject to any disclaimer, the term of this patent is extended or adjusted under 35 U.S.C. 154(b) by 333 days.

(21) Appl. No.: 17/092,037

(22) Filed: Nov. 6, 2020

(65) Prior Publication Data

US 2021/0139545 A1  May 13, 2021

Related U.S. Application Data

(63) Continuation of application No. 16/047,831, filed on Jul. 27, 2018, now Pat. No. 10,844,099, which is a continuation of application No. 14/442,376, filed as application No. PCT/EP2013/074070 on Nov. 18, 2013, now Pat. No. 10,065,996.

(60) Provisional application No. 61/727,283, filed on Nov. 16, 2012.

(30) Foreign Application Priority Data

Aug. 26, 2013 (EP) .................... 13181697

(51) Int. Cl.
*C07K 14/36* (2006.01)
*C12N 15/62* (2006.01)
*G01N 33/68* (2006.01)
*C07K 1/22* (2006.01)

(52) U.S. Cl.
CPC .............. *C07K 14/36* (2013.01); *C12N 15/62* (2013.01); *G01N 33/68* (2013.01); *C07K 1/22* (2013.01); *C07K 2319/22* (2013.01); *C07K 2319/70* (2013.01); *G01N 2333/36* (2013.01)

(58) Field of Classification Search
CPC ...... C07K 14/36; C07K 1/22; C07K 2319/22; C07K 2319/70; C12N 15/62; G01N 33/68; G01N 2333/36
See application file for complete search history.

(56) References Cited

U.S. PATENT DOCUMENTS

| | | | |
|---|---|---|---|
| 5,506,121 A | 4/1996 | Skerra et al. | |
| 5,849,576 A | 12/1998 | Skerra et al. | |
| 6,103,493 A | 8/2000 | Skerra et al. | |
| 6,391,571 B1 * | 5/2002 | Kopetzki | G01N 33/5306 435/7.1 |
| 6,753,165 B1 * | 6/2004 | Cox | C07K 1/1133 435/69.51 |
| 7,776,562 B2 | 8/2010 | Busch et al. | |
| 7,981,632 B2 | 7/2011 | Schmidt | |
| 8,298,782 B2 | 10/2012 | Busch et al. | |
| 8,546,537 B2 | 10/2013 | Kodama et al. | |
| 8,822,260 B2 | 9/2014 | Petti | |
| 8,822,640 B2 | 9/2014 | Wong et al. | |
| 9,150,626 B2 | 10/2015 | Liu et al. | |
| 9,424,774 B2 | 8/2016 | Park | |
| 9,529,003 B2 * | 12/2016 | Kleinfeld | G01N 21/6428 |
| 10,065,996 B2 | 9/2018 | Schmidt | |
| 10,844,099 B2 | 11/2020 | Schmidt | |
| 2004/0018586 A1 * | 1/2004 | Rosendahl | C07K 14/56 435/68.1 |
| 2012/0039879 A1 | 2/2012 | Kodama et al. | |
| 2013/0035471 A1 | 2/2013 | Wong et al. | |
| 2019/0112344 A1 | 4/2019 | Schmidt | |

FOREIGN PATENT DOCUMENTS

| | | |
|---|---|---|
| CA | 2211951 A1 | 8/1996 |
| CA | 2222035 A1 | 3/1997 |
| EP | 0799890 A2 | 10/1997 |
| EP | 0835934 B1 | 6/2010 |
| WO | 9711183 A1 | 3/1997 |
| WO | 02077018 A1 | 10/2002 |
| WO | 2013017954 A2 | 2/2013 |
| WO | 2014076277 A1 | 5/2014 |
| WO | 2017186669 A1 | 11/2017 |

OTHER PUBLICATIONS

Aragana et al., Molecular cloning and nucleotide sequence of the streptavidin gene_ Nucleic Acids Res. Feb. 25, 1986; 14(4 ):11871-1882.
Bayer et al., Close similarity among streptavidin-like, biotin-binding proteins from *Streptomyces*. Biochim Biophys Acta. Jul. 25, 1995;1263(1)160-66.
Braun et al., MuteinDB: the mutein database linking substrates, products and enzymatic reactions directly with genetic variants of enzymes. Database (Oxford). Jun. 21, 2012;2012:bas028.
The International Search Report and Written Opinion issued in PCT/EP2017/059715 dated Jul. 27, 2017—13 gages total.
The Office Action issued by the Canadian Patent Office in Canadian Application No. 2891820 dated Aug. 12, 2019.
Wictionary entry of "mutein", retrieved Aug. 16, 2017 from https://en.wiktionary.org/wiki/mutein (1 page).
(Continued)

*Primary Examiner* — Marcela M Cordero Garcia

(74) *Attorney, Agent, or Firm* — Acuity Law Group, PC; Michael A. Whittaker

(57) ABSTRACT

The invention concerns novel streptavidin muteins. In one embodiment such a the mutein
(a) contains at least two cysteine residues in the region of the amino acid positions 44 to 53 with reference to the amino acid sequence of wild type streptavidin as set forth at SEQ ID NO: 212 and
(b) has a higher binding affinity than
(i) a streptavidin mutein "1" (SEQ ID NO: 112) that comprises the amino acid sequence $Val^{44}$-$Thr^{45}$-$Ala^{46}$-$Arg^{47}$ (SEQ ID NO: 98), or
(ii) wild type-streptavidin of which amino acid residues 14 to 139 are shown as SEQ ID NO: 212
for peptide ligands comprising the amino acid sequence Trp-Ser-His-Pro-Gln-Phe-Glu-Lys (SEQ ID NO: 100).

19 Claims, 13 Drawing Sheets

Specification includes a Sequence Listing.

(56) References Cited

OTHER PUBLICATIONS

Fletcher et al, Self-assembly of proteins and their nucleic acids. J Nanobiotechnology. Jan. 28, 2003;1(1):1 (16 pages).

Redei, 3rd Edition, vol. 2 M-Z, p. 1308, Springer, 2008; excerpt of the entry "mutein" (1 page).

Junttila et al., Single-step Strep-tag® purification for the isolation and identification of protein complexes from mammalian cells. Proteomics. Apr. 2005;5(5):1199-1203.

Knabel et al., Reversible MHC multimer staining for functional isolation of T-cell populations and effective adoptive transfer. Nat Med. Jun. 2002;8(6):631-637.

Korndorfer and Skerra, Improved affinity of engineered streptavidin for the Strep-tag II peptide is due to a fixed open conformation of the lid-like loop at the binding site. Protein Sci. Apr. 2002;11(4):883-893.

Reznik et al., Streptavidins with intersubunit crosslinks have enhanced stability. Nat Biotechnol. Aug. 1996;14 (8):1007-1011.

Schmidt and Skerra, One-step affinity purification of bacterially produced proteins by means of the "Strep tag" and immobilized recombinant core streptavidin. J Chromatogr A. Aug. 5, 1994;676(2):337-345.

Schmidt and Skerra, The Strep-tag system for one-step purification and high-affinity detection or capturing of proteins. Nat Protoc. 2007;2(6):1528-1535.

Stemberger et al., Novel Serial Positive Enrichment Technology Enables Clinical Multiparameter Cell Sorting. PLoS ONE, 2012;71(4): e35798 (11 pages total).

Voss and Skerra, Mutagenesis of a flexible loop in streptavidin leads to higher affinity for the Strep-tag II peptide and improved performance in recombinant protein purification. Protein Eng Aug. 1997;10(8):975-982.

Weber et al., Structural Origins of High-Affinity Biotin Binding to Streptavidin. Science. Jan. 6, 1989;243(4887):85-88.

Yanisch-Peron et al., Improved M13 phage cloning vectors and host strains: nucleotide sequences of the M13mp18 and pUC19 vectors. Gene. 1985;33(1):103-119.

* cited by examiner

Figure 2A streptavidin muteins without deletion

| | |
|---|---|
| + amino acids found at Pos117: | W;Y;F;H;Q;N;E;D;R;L;M;T;S;A;G |
| - not found at Pos117: | K;I;V;P;C |
| + amino acids found at Pos120: | W;Y;F;D;R;L;I;M;V;P;C;S;A;G |
| - not found at Pos120: | H;Q;N;E;K;T |
| + amino acids found at Pos121: | W;Y;F;Q;L;I;M;V;C;S;A;G |
| - not found at Pos121: | H;N;E;D;K;R;P;T | streptavidin muteins with deletion at position 118 and/or 119

| | |
|---|---|
| + amino acids found at Pos117: | H;Q;N;E;K;R;I;T;S;A |
| - not found at Pos117: | W;Y;F;D;L;M;V;P;C;G |
| + amino acids found at Pos120: | W;V |
| - not found at Pos120: | Y;F;H;Q;N;E;D;K;R;L;I;M;P;T;C;S;A;G |
| + amino acids found at Pos121: | Y;F;D;R;L;M;T;S |
| - not found at Pos121: | W;H;Q;N;E;K;I;V;P;C;A;G |

Figure 2B

| | Position: | 117 | 118 | 119 | 120 | 121 |
|---|---|---|---|---|---|---|
| Motif1 (SEQ ID NO: 199): | | Glu<br>Asp<br>Arg<br>His<br>Asn<br>Gln<br>Thr<br>Ser<br>Leu<br>Met | Asn | Ala | Gly | Phe<br>Tyr<br>Met |
| Motif2 (SEQ ID NO: 200): | | Tyr<br>Phe<br>Arg<br>Trp<br>Gln<br>Trp<br>Ser<br>Ala<br>Val | Asn | Ala | Tyr<br>Phe<br>Leu<br>Ile<br>Met | Leu<br>Ile<br>Met<br>Gln<br>Gly |
| Motif3 (SEQ ID NO: 201): | | His<br>Glu<br>Gln<br>Thr<br>Ala<br>Ile<br>Arg<br>Asn<br>Lys<br>Ser | ---- | ---- | Trp<br>Val | Tyr<br>Leu<br>Met<br>Arg<br>Thr<br>Ser<br>Phe |

Fig. 3

```
Wt streptavidin amino acid sequence (residues 14 to 139; SEQ ID
NO: 212)
14
EAGITGTWYNQLGSTFIVTAGADGALTGTYESAVGNAESRYVLTGRYDSAPATDGSGTALGWTV
AWKNNYRNAHSATTWSGQYVGGAEARINTQWLLTSGTTEANAWKSTLVGHDTFTKVKPSAAS
     139
``` pASK75-phoA; SEQ ID NO. 1:

CCATCGAATGGCCAGATGATTAATTCCTAATTTTTGTTGACACTCTATCATTGATAGAGTTATTTTACCACTCCCTAT
CAGTGATAGAGAAAAGTGAAATGAATAGTTCGACAAAAATCTAGAACATGGAGAAAATAAAGTGAAACAAAGCA
CTATTGCACTGGCACTCTTACCGTTACTGTTTACCCCTGTGACAAAAGCCCGGACACCAGAAATGCCTGTTCTGGA
AAACCGGGCTGCTCAGGGCGATATTACTGCACCCGGCGGTGCTCGCCGTTTAACGGGTGATCAGACTGCCGCTCT
GCGTGATTCTCTTAGCGATAAACCTGCAAAAAATATTATTTTGCTGATTGGCGATGGGATGGGGGACTCGGAAATT
ACTGCCGCACGTAATTATGCCGAAGGTGCGGGCGGCTTTTTTAAAGGTATAGATGCCTTACCGCTTACCGGGCAAT
ACACTCACTATGCGCTGAATAAAAAAACCGGCAAACCGGACTACGTCACCGACTCGGCTGCATCAGCAACCGCCT
GGTCAACCGGTGTCAAAACCTATAACGGCGCGCTGGGCGTCGATATTCACGAAAAGATCACCCAACGATTCTGG
AAATGGCAAAAGCCGCAGGTCTGGCGACCGGTAACGTTTCTACCGCAGAGTTGCAGGATGCCACGCCCGCTGCGC
TGGTGGCACATGTGACCTCGCGCAAATGCTACGGTCCGAGCGCGACCAGTGAAAAATGTCCGGGTAACGCTCTGG
AAAAAGGCGGAAAAGGATCGATTACCGAACAGCTGCTTAACGCTCGTGCCGACGTTACGCTTGGCGGCGGCGCA
AAAACCTTTGCTGAAACGGCAACCGCTGGTGAATGGCAGGGAAAAACGCTGCGTGAACAGGCACAGGCGCGTGG
TTATCAGTTGGTGAGCGATGCTGCCTCACTGAATTCGGTGACGGAAGCGAATCAGCAAAAACCCCTGCTTGGCCT
GTTTGCTGACGGCAATATGCCAGTGCGCTGGCTAGGACCGAAAGCAACGTACCATGGCAATATCGATAAGCCCGC
AGTCACCTGTACGCCAAATCCGCAACGTAATGACAGTGTACCAACCCTGGCGCAGATGACCGACAAAGCCATTGA
ATTGTTGAGTAAAAATGAGAAAGGCTTTTTCCTGCAAGTTGAAGGTGCGTCAATCGATAAACAGGATCATGCTGC
GAATCCTTGTGGGCAAATTGGCGAGACGGTCGATCTCGATGAAGCCGTACAACGGGCGCTGGAATTCGCTAAAAA
GGAGGGTAACACGCTGGTCATAGTCACCGCTGATCACGCCCACGCCAGCCAGATTGTTGCGCCGGATACCAAAGC
TCCGGGCCTCACCCAGGCGCTAAATACCAAAGATGGCGCAGTGATGGTGATGAGTTACGGGAACTCCGAAGAGG
ATTCACAAGAACATACCGGCAGTCAGTTGCGTATTGCGGCGTATGGCCCGCATGCCGCCAATGTTGTTGGACTGAC
CGACCAGACCGATCTCTTCTACACCATGAAAGCCGCTCTGGGGCTGAAAccgcctagcgctTGGTCTCACCCGCAGTTC
GAAAAATAATAAGCTTGACCTGTGAAGTGAAAAATGGCGCACATTGTGCGACATTTTTTTTGTCTGCCGTTTACCG
CTACTGCGTCACGGATCTCCACGCGCCCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTCCCTTCCTTTCTCGCCACGTTCGCCGGCTT
TCCCCGTCAAGCTCTAAATCGGGGGCTCCCTTTAGGGTTCCGATTTAGTGCTTTACGGCACCTCGACCCCAAAAAAC
TTGATTAGGGTGATGGTTCACGTAGTGGGCCATCGCCCTGATAGACGGTTTTTCGCCCTTTGACGTTGGAGTCCAC
GTTCTTTAATAGTGGACTCTTGTTCCAAACTGGAACAACACTCAACCCTATCTCGGTCTATTCTTTTGATTTATAAGG
GATTTTGCCGATTTCGGCCTATTGGTTAAAAAATGAGCTGATTTAACAAAAATTTAACGCGAATTTTAACAAAATAT
TAACGCTTACAATTTCAGGTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAAAGGAAGAGTATGAGTA
TTCAACATTTCCGTGTCGCCCTTATTCCCTTTTTTGCGGCATTTTGCCTTCCTGTTTTTGCTCACCCAGAAACGCTGGT
GAAAGTAAAAGATGCTGAAGATCAGTTGGGTGCACGAGTGGGTTACATCGAACTGGATCTCAACAGCGGTAAGA

Fig. 3 continued

```
TCCTTGAGAGTTTTCGCCCCGAAGAACGTTTTCCAATGATGAGCACTTTTAAAGTTCTGCTATGTGGCGCGGTATTA
TCCCGTATTGACGCCGGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTTTGCACAACATGGGGG
ATCATGTAACTCGCCTTGATCGTTGGGAACCGGAGCTGAATGAAGCCATACCAAACGACGAGCGTGACACCACGA
TGCCTGTAGCAATGGCAACAACGTTGCGCAAACTATTAACTGGCGAACTACTTACTCTAGCTTCCCGGCAACAATT
GATAGACTGGATGGAGGCGGATAAAGTTGCAGGACCACTTCTGCGCTCGGCCCTTCCGGCTGGCTGGTTTATTGC
TGATAAATCGGAGCCGGTGAGCGTGGCTCTCGCGGTATCATTGCAGCACTGGGGCCAGATGGTAAGCCCTCCCG
TATCGTAGTTATCTACACGACGGGGAGTCAGGCAACTATGGATGAACGAAATAGACAGATCGCTGAGATAGGTGC
CTCACTGATTAAGCATTGGTAGGAATTAATGATGTCTCGTTTAGATAAAAGTAAAGTGATTAACAGCGCATTAGAG
CTGCTTAATGAGGTCGGAATCGAAGGTTTAACAACCCGTAAACTCGCCCAGAAGCTAGGTGTAGAGCAGCCTACA
TTGTATTGGCATGTAAAAAATAAGCGGGCTTTGCTCGACGCCTTAGCCATTGAGATGTTAGATAGGCACCATACTC
ACTTTTGCCCTTTAGAAGGGGAAAGCTGGCAAGATTTTTTACGTAATAACGCTAAAAGTTTTAGATGTGCTTTACTA
AGTCATCGCGATGGAGCAAAAGTACATTTAGGTACACGGCCTACAGAAAAACAGTATGAAACTCTCGAAAATCAA
TTAGCCTTTTTATGCCAACAAGGTTTTTCACTAGAGAATGCATTATATGCACTCAGCGCAGTGGGGCATTTTACTTT
AGGTTGCGTATTGGAAGATCAAGAGCATCAAGTCGCTAAAGAAGAAAGGGAAACACCTACTACTGATAGTATGCC
GCCATTATTACGACAAGCTATCGAATTATTTGATCACCAAGGTGCAGAGCCAGCCTTCTTATTCGGCCTTGAATTGA
TCATATGCGGATTAGAAAAACAACTTAAATGTGAAAGTGGGTCTTAAAAGCAGCATAACCTTTTTCCGTGATGGTA
ACTTCACTAGTTTAAAAGGATCTAGGTGAAGATCCTTTTTGATAATCTCATGACCAAAATCCCTTAACGTGAGTTTT
CGTTCCACTGAGCGTCAGACCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAGCTACCAACTCTTTTTCCGA
AGGTAACTGGCTTCAGCAGAGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCTATGAGAAAGCGCCAC
GCTTCCCGAAGGGAGAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTTGAGCGTCGATTTTGT
GATGCTCGTCAGGGGGCGGAGCCTATGGAAAAACGCCAGCAACGCGGCCTTTTTACGGTTCCTGGCCTTTTGCT
GGCCTTTTGCTCACATGACCCGACA
``` pASK-IBA2-cytochromeb562; SEQ ID NO. 2:

```
CCATCGAATGGCCAGATGATTAATTCCTAATTTTTGTTGACACTCTATCATTGATAGAGTTATTTTACCACTCCCTAT
CAGTGATAGAGAAAAGTGAAATGAATAGTTCGACAAAAATCTAGATAACGAGGGCAAAAAATGAAAAAGACAG
CTATCGCGATTGCAGTGGCACTGGCTGGTTTCGCTACCGTAGCGCAGGCCGCTGATCTTGAAGACAATATGGAAA
CCCTCAACGACAATTTAAAAGTGATCGAAAAGCGGATAACGCGGCGCAAGTCAAAGACGCGTTAACGAAGATG
CGCGCCGCAGCCCTGGATGCGCAAAAAGCAACGCCGCCGAAGCTCGAAGATAAATCACCGGACAGCCCGGAAAT
```

Fig. 3 continued

GAAAGATTTCCGCCACGGTTTCGACATTCTGGTCGGTCAGATTGACGACGCGCTGAAGCTGGCAAATGAAGGTAA
AGTAAAAGAAGCGCAGGCTGCTGCAGAGCAACTGAAAACGACCCGCAACGCCTATCACCAGAAGTATCGTCCGCC
GAGCGCTTGGAGCCACCCGCAGTTCGAAAAATAATAAGCTTGACCTGTGAAGTGAAAAATGGCGCACATTGTGCG
ACATTTTTTTTGTCTGCCGTTTACCGCTACTGCGTCACGGATCTCCACGCGCCCTGTAGCGGCGCATTAAGCGCGGC
GGGTGTGGTGGTTACGCGCAGCGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCCTTTAGGGTTCCGATTTAGTGCT
TTACGGCACCTCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACACTCAACCCTATCT
CGGTCTATTCTTTTGATTTATAAGGGATTTTGCCGATTTCGGCCTATTGGTTAAAAAATGAGCTGATTTAACAAAAA
TTTAACGCGAATTTTAACAAAATATTAACGCTTACAATTTCAGGTGGCACTTTTCGGGGAAATGTGCGCGGAACCC
CTATTTGTTTATTTTTCTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGGGTGCACGAGTGGGTTACATCG
AACTGGATCTCAACAGCGGTAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGGTCGCCGCATACACTATTCT
CAGAATGACTTGGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGACCGAAGGAGCTA
ACCGCTTTTTTGCACAACATGGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAACTATTAACTGGCGAACTAC
TTACTCTAGCTTCCCGGCAACAATTGATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGCTCTCGCGGTATCATTGCAGCACT
GGGGCCAGATGGTAAGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAGGAATTAATGATGTCTCGTTTAGATAAAAG
TAAAGTGATTAACAGCGCATTAGAGCTGCTTAATGAGGTCGGAATCGAAGGTTTAACAACCCGTAAACTCGCCCA
GAAGCTAGGTGTAGAGCAGCCTACATTGTATTGGCATGTAAAAAATAAGCGGGCTTTGCTCGACGCCTTAGCCATT
GAGATGTTAGATAGGCACCATACTCACTTTTGCCCTTTAGAAGGGGAAAGCTGGCAAGATTTTTTACGTAATAACG
CTAAAAGTTTTAGATGTGCTTTACTAAGTCATCGCGATGGAGCAAAAGTACATTTAGGTACACGGCCTACAGAAAA
ACAGTATGAAACTCTCGAAAATCAATTAGCCTTTTTATGCCAACAAGGTTTTTCACTAGAGAATGCATTATATGCAC
TCAGCGCAGTGGGGCATTTTACTTTAGGTTGCGTATTGGAAGATCAAGAGCATCAAGTCGCTAAAGAAGAAAGGG
AAACACCTACTACTGATAGTATGCCGCCATTATTACGACAAGCTATCGAATTATTTGATCACCAAGGTGCAGAGCC
AGCCTTCTTATTCGGCCTTGAATTGATCATATGCGGATTAGAAAAACAACTTAAATGTGAAAGTGGGTCTTAAAAG
CAGCATAACCTTTTTCCGTGATGGTAACTTCACTAGTTTAAAAGGATCTAGGTGAAGATCCTTTTTGATAATCTCAT
GACCAAAATCCCTTAACGTGAGTTTTCGTTCCACTGAGCGTCAGACCCCGTAGAAAAGATCAAAGGATCTTCTTGA
GATCCTTTTTTTCTGCGCGTAATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACCAAATACTGTCCTTCTAGTGT
AGCCGTAGTTAGGCCACCACTTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCGAACTGAGATACCTACA

Fig. 3 continued

GCGTGAGCTATGAGAAAGCGCCACGCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATCTTTATAGTCCTGTCGGGTTTCGCCA
CCTCTGACTTGAGCGTCGATTTTTGTGATGCTCGTCAGGGGGGCGGAGCCTATGGAAAAACGCCAGCAACGCGGC
CTTTTTACGGTTCCTGGCCTTTTGCTGGCCTTTTGCTCACATGACCCGACA pASK-IBA2-SAm1; SEQ ID NO. 3:

CCATCGAATGGCCAGATGATTAATTCCTAATTTTTGTTGACACTCTATCATTGATAGAGTTATTTTACCACTCCCTAT
CAGTGATAGAGAAAAGTGAAATGAATAGTTCGACAAAAATCTAGATAACGAGGGCAAAAA**ATGAAAAAGACAG
CTATCGCGATTGCAGTGGCACTGGCTGGTTTCGCTACCGTAGCGCAGGCT**GCAGAAGCAGGTATCACCGGCACCT
GGTACAACCAGCTCGGCTCGACCTTCATCGTGACCGCGGGTGCAGACGGAGCTCTGACCGGTACCTACGTCACGG
CGCGTGGCAACGCCGAGAGCCGCTACGTCCTGACCGGTCGTTACGACAGCGCCCCGGCCACCGACGGCAGCGGC
ACCGCCCTCGGTTGGACGGTGGCCTGGAAGAATAACTACCGCAACGCCCACTCCGCGACCACGTGGAGCGGCCA
GTACGTCGGCGGCGCCGAGGCGAGGATCAACACCCAGTGGCTGCTGACCTCCGGCACCACCGAGGCCAACGCCT
GGAAGTCCACGCTGGTCGGCCACGACACCTTCACCAAGGTGAAGCCGTCCGCCGCCTCCTAATAAGCTTGACCTGT
GAAGTGAAAAATGGCGCACATTGTGCGACATTTTTTTTGTCTGCCGTTTACCGCTACTGCGTCACGGATCTCCACGC
GCCCTGTAGCGGCGCATTAAGCGCGGCGGGTGTGGTGGTTACGCGCAGCGTGACCGCTACACTTGCCAGCGCCCT
AGCGCCCGCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTAGGGTGATGGTTCACGTA
GTGGGCCATCGCCCTGATAGACGGTTTTTCGCCCTTTGACGTTGGAGTCCACGTTCTTTAATAGTGGACTCTTGTTC
CAAACTGGAACAACACTCAACCCTATCTCGGTCTATTCTTTTGATTTATAAGGGATTTTGCCGATTTCGGCCTATTG
GTTAAAAAATGAGCTGATTTAACAAAAATTTAACGCGAATTTTAACAAAATATTAACGCTTACAATTTCAGGTGGC
ACTTTTCGGGGAAATGTGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAAGTAAAAGATGCTGAAGAT
CAGTTGGGTGCACGAGTGGGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGCGTGACACCACGATGCCTGTAGCAATGGCAACAA
CGTTGCGCAAACTATTAACTGGCGAACTACTTACTCTAGCTTCCCGGCAACAATTgATAGACTGGATGGAGGCGGA
TAAAGTTGCAGGACCACTTCTGCGCTCGGCCCTTCCGGCTGGCTGGTTTATTGCTGATAAATCTGGAGCCGGTGAG
CGTGGCTCTCGCGGTATCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGATTAAGCATTGGTAG
GAATTAATGATGTCTCGTTTAGATAAAAGTAAAGTGATTAACAGCGCATTAGAGCTGCTTAATGAGGTCGGAATC
GAAGGTTTAACAACCCGTAAACTCGCCCAGAAGCTAGGTGTAGAGCAGCCTACATTGTATTGGCATGTAAAA

Fig. 3 continued

```
AATAAGCGGGCTTTGCTCGACGCCTTAGCCATTGAGATGTTAGATAGGCACCATACTCACTTTTGCCCTTTAGAAG
GGGAAAGCTGGCAAGATTTTTTACGTAATAACGCTAAAAGTTTTAGATGTGCTTTACTAAGTCATCGCGATGGAGC
AAAAGTACATTTAGGTACACGGCCTACAGAAAAACAGTATGAAACTCTCGAAAATCAATTAGCCTTTTTATGCCAA
CAAGGTTTTTCACTAGAGAATGCATTATATGCACTCAGCGCaGTGGGGCATTTTACTTTAGGTTGCGTATTGGAAG
ATCAAGAGCATCAAGTCGCTAAAGAAGAAAGGGAAACACCTACTACTGATAGTATGCCGCCATTATTACGACAAG
CTATCGAATTATTTGATCACCAAGGTGCAGAGCCAGCCTTCTTATTCGGCCTTGAATTGATCATATGCGGATTAGAA
AAACAACTTAAATGTGAAAGTGGGTCTTAAAAGCAGCATAACCTTTTTCCGTGATGGTAACTTCACTAGTTTAAAA
GGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTGGCCTTTTGCTCACATG
ACCCGACA
``` pASK-IBA2-SAm4001; SEQ ID NO. 4:

```
CCATCGAATGGCCAGATGATTAATTCCTAATTTTTGTTGACACTCTATCATTGATAGAGTTATTTTACCACTCCCTAT
CAGTGATAGAGAAAAGTGAAATGAATAGTTCGACAAAAATCTAGATAACGAGGGCAAAAAATGAAAAAGACAG
CTATCGCGATTGCAGTGGCACTGGCTGGTTTCGCTACCGTAGCGCAGGCTGCAGAAGCAGGTATCACCGGCACCT
GGTACAACCAGCTCGGCTCGACCTTCATCGTGACCGCGGGTGCAGACGGAGCTCTGACCGGTACCTACGCTTGCG
GCCGGGGCAACGCCGAGTGCCGCTACGTCCTGACCGGTCGTTACGACAGCGCCCCGGCCACCGACGGCAGCGGC
ACCGCCCTCGGTTGGACGGTGGCCTGGAAGAATAACTACCGCAACGCCCACTCCGCGACCACGTGGAGCGGCCA
GTACGTCGGCGGCGCCGAGGCGAGGATCAACACCCAGTGGCTGCTGACCTCCGGCACCACCGAGGCCAACGCCT
GGAAGTCCACGCTGGTCGGCCACGACACCTTCACCAAGGTGAAGCCGTCCGCCGCCTCCTAATAAGCTTGACCTGT
GAAGTGAAAAATGGCGCACATTGTGCGACATTTTTTTTGTCTGCCGTTTACCGCTACTGCGTCACGGATCTCCACGC
GCCCTGTAGCGGCGCATTAAGCGCGGCGGGTGTGGTGGTTACGCGCAGCGTGACCGCTACACTTGCCAGCGCCCT
AGCGCCCGCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTAGGGTGATGGTTCACGTA
GTGGGCCATCGCCCTGATAGACGGTTTTTCGCCCTTTGACGTTGGAGTCCACGTTCTTTAATAGTGGACTCTTGTTC
CAAACTGGAACAACACTCAACCCTATCTCGGTCTATTCTTTTGATTTATAAGGGATTTTGCCGATTTCGGCCTATTG
GTTAAAAAATGAGCTGATTTAACAAAAATTTAACGCGAATTTTAACAAAATATTAACGCTTACAATTTCAGGTGGC
ACTTTTCGGGGAAATGTGCGCGGAACCCCTATTTGTTTATTTTTCTAAATACATTCAAATATGTATCCGCTCATGAG
```

Fig. 3 continued

```
ACAATAACCCTGATAAATGCTTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAAGTAAAAGATGCTGAAGAT
CAGTTGGGTGCACGAGTGGGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGCGTGACACCACGATGCCTGTAGCAATGGCAACAA
CGTTGCGCAAACTATTAACTGGCGAACTACTTACTCTAGCTTCCCGGCAACAATTgATAGACTGGATGGAGGCGGA
TAAAGTTGCAGGACCACTTCTGCGCTCGGCCCTTCCGGCTGGCTGGTTTATTGCTGATAAATCTGGAGCCGGTGAG
CGTGGCTCTCGCGGTATCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGATTAAGCATTGGTAG
GAATTAATGATGTCTCGTTTAGATAAAAGTAAAGTGATTAACAGCGCATTAGAGCTGCTTAATGAGGTCGGAATC
GAAGGTTTAACAACCCGTAAACTCGCCCAGAAGCTAGGTGTAGAGCAGCCTACATTGTATTGGCATGTAAAAAAT
AAGCGGGCTTTGCTCGACGCCTTAGCCATTGAGATGTTAGATAGGCACCATACTCACTTTTGCCCTTTAGAAGGGG
AAAGCTGGCAAGATTTTTTACGTAATAACGCTAAAAGTTTTAGATGTGCTTTACTAAGTCATCGCGATGGAGCAAA
AGTACATTTAGGTACACGGCCTACAGAAAAACAGTATGAAACTCTCGAAAATCAATTAGCCTTTTTATGCCAACAA
GGTTTTTCACTAGAGAATGCATTATATGCACTCAGCGCaGTGGGGCATTTTACTTTAGGTTGCGTATTGGAAGATC
AAGAGCATCAAGTCGCTAAAGAAGAAAGGGAAACACCTACTACTGATAGTATGCCGCCATTATTACGACAAGCTA
TCGAATTATTTGATCACCAAGGTGCAGAGCCAGCCTTCTTATTCGGCCTTGAATTGATCATATGCGGATTAGAAAA
ACAACTTAAATGTGAAAGTGGGTCTTAAAAGCAGCATAACCTTTTTCCGTGATGGTAACTTCACTAGTTTAAAAGG
ATCTAGGTGAAGATCCTTTTTGATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCAGGGGGGC
GGAGCCTATGGAAAAACGCCAGCAACGCGGCCTTTTTACGGTTCCTGGCCTTTTGCTGGCCTTTTGCTCACATGAC
CCGACA
```

Fig. 3 continued

GFP-StrepII (SEQ ID NO: 104):

MSKGEELFTGVVPILVELDGDVNGHKFSVSGEGEGDATYGKLTLKFICTTGKLPVPWPTLVTTFSYGVQCFSRYPDHMK
RHDFFKSAMPEGYVQERTIFFKDDGNYKTRAEVKFEGDTLVNRIELKGIDFKEDGNILGHKLEYNYNSHNVYIMADKQK

NGIKVNFKIRHNIEDGSVQLADHYQQNTPIGDGPVLLPDNHYLSTQSALSKDPNEKRDHMVLLEFVTAAGITHGMDEL
YQSA<u>WSHPQFEK</u>

GFP-di-tag3 (SEQ ID NO: 105):

MSKGEELFTGVVPILVELDGDVNGHKFSVSGEGEGDATYGKLTLKFICTTGKLPVPWPTLVTTFSYGVQCFSRYPDHMK
RHDFFKSAMPEGYVQERTIFFKDDGNYKTRAEVKFEGDTLVNRIELKGIDFKEDGNILGHKLEYNYNSHNVYIMADKQK
NGIKVNFKIRHNIEDGSVQLADHYQQNTPIGDGPVLLPDNHYLSTQSALSKDPNEKRDHMVLLEFVTAAGITHGMDEL
YQSA<u>WSHPQFEK</u>GGGSGGGSGGGS<u>WSHPQFEK</u>

Cytb562-StrepII (SEQ ID NO: 106):

ADLEDNMETLNDNLKVIEKADNAAQVKDALTKMRAAALDAQKATPPKLEDKSPDSPEMKDFRHGFDILVGQIDDALK
LANEGKVKEAQAAAEQLKTTRNAYHQKYRPPSA<u>WSHPQFEK</u>

Cytb562-di-tag3 (SEQ ID NO: 107):

ADLEDNMETLNDNLKVIEKADNAAQVKDALTKMRAAALDAQKATPPKLEDKSPDSPEMKDFRHGFDILVGQIDDALK
LANEGKVKEAQAAAEQLKTTRNAYHQKYRPPSA<u>WSHPQFEK</u>GGGSGGGSGGGS<u>WSHPQFEK</u>

The sequence of the strep-tagII module is underlined

Fig. 4

Sequence alignment showing positions 14-139 of wild-type and mutein proteins.

Common sequence framework (positions 14-139):
EAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEA...STLVGHDTFTKVGHDTFTKVPSAAS Labels (top to bottom):
- Wt
- mutein"1"
- mutein"2"
- Table1
- m400
- m402
- Table2
- m4001
- Table3
- mutein"1"-m36
- mutein"1"-m23
- mutein"1"-m41
- mutein"1"-m4
- mutein"1"-m12
- mutein"1"-m22
- mutein"1"-m31
- mutein"1"-m32
- mutein"1"-m35
- mutein"1"-m38
- mutein"1"-m40
- mutein"1"-m42
- mutein"1"-m45
- mutein"1"-m46
- mutein"1"-m47
- mutein"1"-m7
- mutein"1"-m10
- mutein"1"-m17
- mutein"1"-m21
- mutein"1"-m24
- mutein"1"-m27
- mutein"1"-m28
- mutein"1"-m30
- mutein"1"-m33
- mutein"1"-m1
- mutein"1"-m3
- mutein"1"-m8
- mutein"1"-m15
- mutein"1"-m6
- mutein"1"-m9
- mutein"1"-m20
- mutein"1"-m34
- mutein"1"-m14
- mutein"1"-m18
- mutein"1"-m19

Fig. 4 continued

```
              14        20        30        40        50        60        70        80        90       100       110       120       130    139
              |         |         |         |         |         |         |         |         |         |         |         |         |      |
Table4
m4001-m8:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEENAGFSTLVGHDTFTKVKPSAAS
m4001-m21:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEDNAGYSTLVGHDTFTKVKPSAAS
m4001-m9:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEENAGYSTLVGHDTFTKVKPSAAS
m4001-m1:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTERNAMMSTLVGHDTFTKVKPSAAS
m4001-m2:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTERNAGFSTLVGHDTFTKVKPSAAS
m4001-m3:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEANAPASTLVGHDTFTKVKPSAAS
m4001-m5:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEANAMVSTLVGHDTFTKVKPSAAS
m4001-m13:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEANASASTLVGHDTFTKVKPSAAS
m4001-m14:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEANAGFSTLVGHDTFTKVKPSAAS
m4001-m24:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEQNAMVSTLVGHDTFTKVKPSAAS
m4001-m4:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTENNAGYSTLVGHDTFTKVKPSAAS
m4001-m6:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEANAAVSTLVGHDTFTKVKPSAAS
m4001-m7:     EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTESNAMISTLVGHDTFTKVKPSAAS
m4001-m10:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEHNAGYSTLVGHDTFTKVKPSAAS
m4001-m15:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTESNAMASTLVGHDTFTKVKPSAAS
m4001-m23:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEQNAVASTLVGHDTFTKVKPSAAS
m4001-m17:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEYNAYMSTLVGHDTFTKVKPSAAS
m4001-m12:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTELNAWGSTLVGHDTFTKVKPSAAS
m4001-m20:    EAAGITGTWYNQLGSTFIVTAGADGALTGTYACGRGNAECRIVLTGRYDSAPATDGSGTALGWTVAWKNNYRNAHSATTWSGQYVGGAEAARINTQWLLTSGTTEHNASMSTLVGHDTFTKVKPSAAS
Table5
mutein"1"-m207: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEYNAFLSTLVGHDTFTKVKPSAAS
mutein"1"-m106: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTET---WLSTLVGHDTFTKVKPSAAS
mutein"1"-m111: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEH---WLSTLVGHDTFTKVKPSAAS
mutein"1"-m100: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEI---WRSTLVGHDTFTKVKPSAAS
mutein"1"-m110: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEH---WTSTLVGHDTFTKVKPSAAS
mutein"1"-m104: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEF---NAXISTLVGHDTFTKVKPSAAS
mutein"1"-m108: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEF---NAYLSTLVGHDTFTKVKPSAAS
Table6
mutein"1"-m207: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTET---WLSTLVGHDTFTKVKPSAAS
mutein"1"-m212: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEH---WLSTLVGHDTFTKVKPSAAS
mutein"1"-m202: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEI---WRSTLVGHDTFTKVKPSAAS
mutein"1"-m204: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEH---WTSTLVGHDTFTKVKPSAAS
mutein"1"-m206: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTET---WRSTLVGHDTFTKVKPSAAS
mutein"1"-m208: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEA---WRSTLVGHDTFTKVKPSAAS
mutein"1"-m203: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTER---WSSTLVGHDTFTKVKPSAAS
mutein"1"-m209: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTER---WRSTLVGHDTFTKVKPSAAS
mutein"1"-m200: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEN---WRSTLVGHDTFTKVKPSAAS
mutein"1"-m201: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEK---WSSTLVGHDTFTKVKPSAAS
mutein"1"-m205: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTES---VFSTLVGHDTFTKVKPSAAS
mutein"1"-m211: EAAGITGTWYNQLGSTFIVTAGADGALTGTYVTARGNAESRYVLTGRYDSAPATDGSGTALGWTVAWKNNYRNAHSATTWSGQYVGGAEAARINTQWLLTSGTTEK---WTSTLVGHDTFTKVKPSAAS
```

Fig. 4 continued

```
Table 7           14         20         30         40         50         60         70         80         90        100        110        120        130    139
                   |          |          |          |          |          |          |          |          |          |          |          |          |      |
mutein"1"-m300: EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEA---WYSTLVGHDTFTKVKPSAAS
mutein"1"-m301: EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEH---WMSTLVGHDTFTKVKPSAAS
mutein"1"-m302: EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEH---WYSTLVGHDTFTKVKPSAAS
mutein"1"-m303: EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEE---WYSTLVGHDTFTKVKPSAAS
mutein"1"-m304: EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEQ---WYSTLVGHDTFTKVKPSAAS
Example 12
Mutein m1-9:    EAGITGTWYNQLGSTFIVTAGADGALTGTYVTARGMAESRYVLTGRYDSAPATDGSGTALGWTVAWKNNYRNAHSATTWSGQYVGGAEAARINTQWLLTSGTTEENAGYSTLVGHDTFTKVKPSAAS
```

When the muteins were secreted by E. coli to the periplasm, as done during screening within the filter sandwich assay, the resulting protein sequences were produced as shown above with an additional alanine at the N-terminal end (position 13). When the muteins were produced by E. coli in the cytosol as inclusion bodies for subsequent refolding, purification and analysis, the resulting protein sequences were produced as shown above with an additional methionine at the N-terminal end (position 13). Deleted amino acids are indicated by a dash (-). Amino acid numbering has been conducted in case of deletions in a manner maintaining comparability at equivalent positions. It has, however, to be noted that the molecules containing deletions are decreased in length by the number of deletions which is 2 for the corresponding muteins of Figure 4. This means that the muteins of Figure 4 without deletions contain a total of 127 amino acids while those with deletions contain a total of 125 amino acids. The amino acid residues resulting from randomized codons in the different libraries are shown in bold.

STREPTAVIDIN MUTEINS AND METHODS OF USING THEM

CROSS-REFERENCE TO RELATED APPLICATIONS

The present application is continuation of U.S. patent application Ser. No. 16/047,831, filed Jul. 27, 2018, now U.S. Pat. No. 10,844,099, which is a continuation of U.S. patent application Ser. No. 14/442,376, filed May 12, 2015, now U.S. Pat. No. 10,065,996, which is the United States national stage patent application of International Application No. PCT/EP2013/074070, filed Nov. 18, 2013, which claims the right of priority of U.S. Provisional Application No. 61/727,283 filed Nov. 16, 2012, and of European Patent Application No. 13 181 697.7 filed Aug. 26, 2013, the entire contents of each of which are incorporated herein by reference for all purposes.

SEQUENCE LISTING

The instant application contains a Sequence Listing which has been submitted in ASCII format via EFS-Web and is hereby incorporated by reference in its entirety. Said ASCII copy, created on Nov. 6, 2020, is named SCH-2600-CT2_SeqListing_txt and is 152 kilobytes in size.

FIELD OF THE INVENTION

The present invention relates to novel streptavidin muteins, methods of producing such muteins by means of recombinant DNA technology as well as the use of these streptavidin muteins for the isolation, purification and determination of biological substances such as recombinant proteins or biological entities such as cells having specific receptor molecules on the cell surface.

BACKGROUND

Short peptide affinity tags have become indispensable in protein research. They cannot only be used for affinity purification but also for detection and assay of any fused recombinant protein without the need for any prior knowledge of its biochemical properties. The affinity tag Strep-Tag®II (Schmidt & Skerra, Nature Protocols 2 (2007), 1528-1535; U.S. Pat. No. 5,506,121, having the sequence Trp-Ser-His-Pro-Gln-Phe-Glu-Lys, SEQ ID NO: 100) is particularly popular for providing recombinant proteins at high purity and functionality by using physiological conditions within a rapid one-step protocol. The currently most efficient streptavidin based receptor for the Strep-Tag®II affinity tag are streptavidin muteins with improved binding affinity that are named Strep-Tactin® (Voss & Skerra, Protein Engineering 10 (1997), 975-982; U.S. Pat. No. 6,103,493 or European Patent 0 835 934). The Strep-Tag®II binds to the biotin binding pocket enabling mild competitive elution with biotin derivatives, preferably desthiobiotin, for repeated use of the affinity resins. The Strep-Tag®II:Strep-Tactin® system has provided powerful applications in the last 15 years for purification, detection and assay of recombinant proteins (reviewed in Schmidt & Skerra, Nature Protocols 2 (2007), 1528-1535) and even of cells (Knabel et al., Nature Medicine 8 (2002), 631-637).

The Strep-Tag®II:Strep-Tactin® interaction is characterized by comparatively fast binding and dissociation kinetics and a medium binding affinity. Fast kinetics support higher flow rates during column chromatography where fast association kinetics ensures efficient binding and fast dissociation kinetics enables efficient competitive elution.

On the other hand, medium binding affinity and fast dissociation kinetics are limiting when at least one of the binding partners—Strep-Tag®II fusion protein or Strep-Tactin®—is applied or present at low concentration. Examples for the first case are poor expression resulting in diluted extracts with respect to the Strep-Tag®II fusion protein or using large buffer volumes for cell lysis after expression or secreting the Strep-Tag®II fusion protein into the cell culture supernatant. In all examples, a large sample volume containing the target protein at low concentration needs to be applied to the affinity column often resulting in column breakthough, significant loss of Strep-Tag®II fusion protein and reduced yield. The other variant of working under suboptimal conditions for this medium binding affinity interaction is diluting the Strep-Tactin® reaction partner as it is the case in batch purification which, as compared to column purification, equally may result in reduced yield for the Strep-Tag®II fusion protein.

These limitations were reduced by developing the Di-tag affinity tag (similar or slightly different sequences are also also known under the names Strep-Tag®III, One-STrEP-tag or Twin-Strep-Tag®) consisting of a sequential arrangement of two (or more) Strep-Tag®II moieties connected by a short linker. The linker and also the streptavidin binding moieties may be used in different variations. Examples of Di-tag sequences are the di-tag3 sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 103) or the di-tag2 sequence Trp-Ser-His-Pro-Gln-Phe-Glu-Lys-(GlyGlyGlySer)$_2$-Trp-Ser-His-Pro-Gln-Phe-Glu-Lys (SEQ ID NO: 109) (Junttila et al., Proteomics 5 (2005), 1199-1203; U.S. Pat. No. 7,981,632). The biochemical reason for improved binding is the avidity effect, i.e. the combined synergistic binding of two streptavidin binding moieties to tetrameric Strep-Tactin®. This switches the comparatively fast off rate under non-competitive conditions to more steady binding while preserving efficient elution capability by adding a competitor that reverses the synergistic effect. In fact, the Di-tag features all beneficial application properties of Strep-Tag®II, including efficient elution under competitive conditions, but additionally enables a more universal use in applications requiring more stable binding. One drawback is, however, that it has a considerably larger size (factor 3) than the short Strep-Tag®II which makes adverse effects to the fused recombinant proteins more probable.

In addition to affinity purification, also assays may be quite demanding regarding binding affinity and dissociation kinetics, particularly when extensive washing is required. Thus, if a Strep-Tag®II fusion protein to be analyzed is bound to a Strep-Tactin® coated solid phase, significant loss might occur during washing due to comparatively fast dissociation kinetics finally resulting in reduced sensitivity of the whole assay. Examples are ELISA or BiaCore™ or Quarz Crystal Microbalance (QCM) experiments where the recombinant Strep-Tag®(II) fusion protein is immobilized on a microtitre plate or CM5 chip or sensor surface, respectively, each coated with Strep-Tactin®. The same is true, e.g., for applications where low amounts of a Strep-Tag®(II) fusion protein, immobilized on a solid phase, are to be detected by Strep-Tactin® conjugated to a label in a sensitive manner. Examples are ELISA or Western blot or cell based assay experiments where the recombinant Strep-Tag®(II) fusion protein is immobilized on or bound to a microtitre plate or membrane (nitrocellulose/PVDF) or a cell membrane, respectively. A cell membrane can also be considered as a solid phase as a bound Strep-Tag®(II) protein can be, e.g., detected by labeled Strep-Tactin® via FACS. In fact, any detection method for a Strep-tag(II) fusion protein would be improved by a streptavidin mutein with increased binding affinity for the Strep-tag(II) or a Di-tag.

For these reasons a streptavidin mutein having a higher binding affinity for the short Strep-tag(II) than those muteins disclosed by U.S. Pat. No. 6,103,493 is still desirable. With such a streptavidin mutein, applications could be rendered possible using the short Strep-Tag®II affinity tag which are currently only feasible by using the Di-tag. But also applications like purification, detection or assay for Di-tag fusion proteins would be enhanced by a streptavidin mutein with higher binding affinity for streptavidin binding peptides than the streptavidin muteins of U.S. Pat. No. 6,103,493. Examples for such applications are highly demanding situations in the purification applications described above or/and capture of diluted Di-tag fusion proteins in a batch format, e.g. capture of protein complexes with streptavidin mutein coated magnetic beads or/and in detection assays where highest sensitivity combined with extended washing is required. Such streptavidin muteins with enhanced affinities would also be desirable for most stable immobilization of fusion proteins carrying a streptavidin affinity tag such as the Strep-Tag®II or the Di-tag, wherein these fusion proteins are to be characterized or assayed or detected on a solid phase, like, e.g., a chip for surface plasmon resonance (SPR), coated with said streptavidin muteins and wherein optionally said solid phase coated with said streptavidin muteins can be easily and under mild conditions be regenerated which means be deliberated again from the first Strep-Tag®II or the Di-tag fusion protein to become ready for the binding of another Strep-Tag®II or the Di-tag fusion protein.

It is therefore an object of the present invention to provide a streptavidin mutein having higher affinity than those muteins disclosed by U.S. Pat. No. 6,103,493 for streptavidin binding peptides such as the Strep-Tag®II and/or Di-tag affinity peptide(s).

SUMMARY OF THE INVENTION

In a first aspect the invention provides a streptavidin mutein, wherein the streptavidin mutein
(a) contains at least two cysteine residues in the region of the amino acid positions 44 to 53 with reference to the amino acid sequence of wild type streptavidin as set forth at SEQ ID NO: 15 and
(b) has a higher binding affinity than each of
 (i) a streptavidin mutein that comprises the amino acid sequence $Val^{44}$-$Thr^{45}$-$Ala^{46}$-$Arg^{47}$ (SEQ ID NO: 98), or
 (ii) a streptavidin mutein that comprises the amino acid sequence $Ile^{44}$-$Gly^{45}$-$Ala^{46}$-$Arg^{47}$ (SEQ ID NO: 99) at amino acid positions 44 to 47, or
 (iii) wild type-streptavidin (SEQ ID NO: 15)
for peptide ligands comprising the amino acid sequence Trp-Ser-His-Pro-Gln-Phe-Glu-Lys (SEQ ID NO: 100).

In a second aspect, the invention provides a streptavidin mutein, wherein the streptavidin mutein
(a) contains at least one mutation in the region of amino acid positions 115 to 121 with reference to the amino acid sequence of wild type streptavidin as set forth at SEQ ID NO: 15 and
(b) has a higher binding affinity than each of
 (i) a streptavidin mutein that comprises the amino acid sequence $Val^{44}$-$Thr^{45}$-$Ala^{46}$-$Arg^{47}$ (SEQ ID NO: 98), or
 (ii) a streptavidin mutein that comprises the amino acid sequence $Ile^{44}$-$Gly^{45}$-$Ala^{46}$-$Arg^{47}$ (SEQ ID NO: 99) at amino acid positions 44 to 47, or
 (iii) wild type-streptavidin (SEQ ID NO: 15) for peptide ligands comprising the amino acid sequence Trp-Ser-His-Pro-Gln-Phe-Glu-Lys (SEQ ID NO: 100).

In a third aspect, the invention provides a nucleic acid molecule that comprises a sequence coding for a streptavidin mutein according to the first or second aspect. The nucleic acid might be a vector comprising at least one copy of such nucleic acid molecule in an operatively functionally environment.

In a fourth aspect, the invention provides a cell that is transformed or transfected with a nucleic acid or a vector according to the third aspect.

The invention also provides a method of producing a streptavidin mutein according to the first or second aspect, comprising:
(a) transforming a suitable host cell with a vector which contains a nucleic acid coding for the streptavidin mutein,
(b) culturing the host cell under conditions in which an expression of the streptavidin mutein takes place,
(c) isolating the mutein.

The invention also provides a method of isolating, purifying or determining a protein that is fused with a) a peptide sequence of the formula Trp-Xaa-His-Pro-Gln-Phe-Yaa-Zaa (SEQ ID NO: 101) in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gn-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg, comprising contacting a sample containing said protein with a streptavidin mutein as described herein, under suitable conditions to bind the peptide sequence to the streptavidin mutein, and separating the resulting complex from said sample.

The invention also provides a method of immobilizing a protein which is fused with a) a peptide sequence of formula Trp-Xaa-His-Pro-Gln-Phe-Yaa-Zaa (SEQ ID NO: 101) in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg, comprising contacting said protein to a solid phase which carries a streptavidin mutein according to the first or second aspect, under conditions for immobilizing said protein.

The invention also provides a method of determining or isolating a substance which carries a group capable of binding to streptavidin, comprising contacting said substance with the streptavidin mutein as described herein under suitable conditions for binding thereto, and determining or isolating said substance.

The invention also provides a reagent kit comprising a streptavidin mutein as described herein, and at least one reagent selected from the group consisting of a conventional buffer, an auxiliary substance and an additive. The invention also provides a streptavidin mutein as described herein immobilized on a solid support such as a chromatography resin, an ELISA plate or a chip for surface plasmon resonance (SPR) measurements.

These aspects of the invention will be more fully understood in view of the following description, drawings and non-limiting examples.

DETAILED DESCRIPTION

In evolutionary research approaches it has now been surprisingly found that the binding affinity of streptavidin muteins for the Strep-Tag®II affinity peptide (Trp-Ser-His-Pro-Gln-Phe-Glu-Lys, SEQ ID NO: 100) can be significantly increased in different ways. In a first set of experiments, streptavidin muteins with significantly increased binding affinity for the Strep-Tag®II in comparison to the binding affinity disclosed by U.S. Pat. No. 6,103,493 for mutein "1" (SEQ ID NO: 16) (44-47=VTAR) and mutein "2" (SEQ ID NO: 17) (44-47=IGAR) could be obtained by introducing a disulfide bridge in the region of amino acids 44 to 53. In a second set of experiments, the binding affinity for the Strep-tagII could be improved by mutation in the region of amino acid positions 115 to 121. Similar mutations/amino acid exchanges in the region of the amino acid positions 115 to 121 were observed, irrespective which streptavidin mutein in the region of amino acids 44 to 53 was used as starting point, i.e. mutein "1" disclosed by U.S. Pat. No. 6,103,493 or the most preferred disulfide containing mutein of the present invention, thereby indicating that the affinity increase found by mutation(s) in the region of the amino acid positions 115 to 121 is not dependent on the sequence of amino acids 44 to 53. Thus, each of these two aspects of the invention improves the Strep-Tag®II binding affinity of any streptavidin mutein including wild type streptavidin (wt-streptavidin).

The streptavidin muteins of the present invention may correspond to the amino acid sequence of wt-streptavidin outside the region of the amino acid positions 115-121. On the other hand the amino acid sequence according to the invention can also be different to the wt-streptavidin sequence outside the region of the amino acids 115 to 121. Likewise, the streptavidin muteins of the present invention that contain two cysteine residues in the region of amino acids 44 to 53 can also have mutations at other sequence positions of streptavidin. Such variants of the streptavidin sequence include naturally occurring as well as artificially produced variants and the modifications are understood as substitution including those disclosed by U.S. Pat. No. 6,103,493, those containing a disulfide bond, insertions, deletions of amino acid residues as well as N- or/and C-terminal deletions or additions.

The term "higher affinity" or "higher binding affinity" as used herein refers to the affinity measured for a complex composed of a streptavidin mutein according to the invention and the Strep-Tag®II (WSHPQFEK, SEQ ID NO: 100) peptide ligand compared to the affinity of a complex that the Strep-Tag®II ligand forms with i) a streptavidin mutein that comprises the amino acid sequence Val$^{44}$-Thr$^{45}$-Ala$^{46}$-Arg$^{47}$ (SEQ ID NO: 98), or (ii) a streptavidin mutein that comprises the amino acid sequence Ile$^{44}$-Gly$^{45}$-Ala$^{46}$-Arg$^{47}$ (SEQ ID NO: 99) at amino acid positions 44 to 47, or (iii) wild type-streptavidin (SEQ ID NO: 15). It is however also possible that the muteins of the present invention also have a higher affinity for other streptavidin binding peptides such as WRHPQFGG (SEQ ID NO: 102, Strep-Tag®) or the Di-tag3 of SEQ ID NO: 103 than wild-type (wt) streptavidin or the streptavidin muteins "1" and "2" that are known from U.S. Pat. No. 6,103,493 or European Patent 0 835 934).

"Higher affinity" or "higher binding affinity" can, for example, be determined using the streptavidin variants to be compared (wt streptavidin; streptavidin muteins according to U.S. Pat. No. 6,103,493 and streptavidin muteins according to the present invention) immobilized to Sepharose® and the Strep-Tag®II as a C-terminal fusion to the red colored protein cytochromeb562. The binding affinity of said cytochromeb562-Strep-Tag®II fusion protein to the different streptavidin variants immobilized on Sepharose® can be visually followed in chromatography experiments in which a column with the different immobilized streptavidin muteins are loaded with the cytochromeb562-Strep-tagII fusion protein and are subsequently washed. Washing the column with large buffer volumes induces bleeding of cytochromeb562-Strep-tagII fusion protein from the Sepharose column with immobilized streptavidin (mutein). This effect is more related to binding affinity than to off kinetics because efficient rebinding is enabled in the column matrix densely packed with streptavidin mutein coated resin as long as the flow rates of the washing buffer are moderate. Thus, lower binding affinity reduces the capacity of the column for the Strep-Tag® fusion protein to be purified since protein is lost from a maximally loaded affinity column in dependency of the applied volume of washing buffer. In other words, the capacity diminishing effect is less pronounced when the binding affinity between the Strep-Tag® fusion protein and the streptavidin mutein immobilized to the column is higher. A further way to test binding affinity in such a chromatography based assay format is to apply a comparatively large volume of diluted colored cytochromeb562 with C-terminal Strep-Tag®II to columns harboring the different immobilized streptavidin muteins and to determine the enrichment of the tagged cytochromeb562 on the column. Enrichment is more pronounced on columns harboring a streptavidin mutein with higher affinity for the Strep-Tag®II. Being measured by applying the Strep-Tag®II fusion protein at a certain flow rate—which must be controlled to be similar in all cases under comparison—to the columns with the different immobilized streptavidin muteins, binding affinity determined in this manner is specified by parameters such as association and dissociation rate constants ($k_{on}$ and $k_{off}$) meaning kinetic parameters rather than thermodynamic equilibrium parameters. In fact in such a flow based assay, an interaction of a certain affinity that is determined by faster on and off kinetics thereby reaching or approaching faster equilibrium on the column is preferable over an interaction of equal affinity but being determined by slower kinetics.

Using these chromatography based systems for binding affinity assessment has the advantage of being closely comparable to affinity purification, one of the most important practical applications of the streptavidin muteins of the present invention, thereby avoiding measurement method dependent variations indicating favorable differences that cannot be translated into a practical advantage for affinity chromatography as, as explained above, performance is not only dependent on the overall affinity constant but also on the underlying kinetics. Using cytochromeb562 as fusion partner for the affinity tag Strep-Tag®II, which is not related to bacterial alkaline phosphatase that has been used as fusion partner during library screenings to select the different streptavidin muteins, ensures that the observed differences in these assays for binding affinity assessment are due to an interaction between the streptavidin mutein and Strep-Tag®II and not to non-specific interactions between the streptavidin mutein and bacterial alkaline phosphatase that potentially could have been selected during screening.

A further assay for binding affinity assessment is ELISA by using the muteins immobilized to the wells of a microtitre plate and applying different concentrations of the Strep-Tag®II fused to an enzyme like bacterial alkaline phosphatase and measuring the extent of complex formation in dependence of the applied concentration. The dissociation constant ($K_D$) of the binding affinity between streptavidin mutein and Strep-Tag®II peptide can, for example, be determined as described in Example 5 of U.S. Pat. No. 6,103,493 or as described in Example 10 herein.

Further methods to determine binding affinities are fluorescence titration (for example as described in Example 6 of U.S. Pat. No. 6,103,493), titration calorimetry or surface plasmon resonance (SPR) measurements such as BiaCore™ measurement. The binding affinity determined in this manner is specified by parameters such as affinity ($K_A$) or dissociation ($K_D$) constants or also by parameters such as affinity rate ($k_{on}$) and dissociation rate ($k_{off}$) constants in case of SPR measurements such as BiaCore™.

The increase of the binding affinity which is obtained with a streptavidin mutein modified according to the present invention within the region of the amino acid positions 115 to 121 and/or containing a disulfide bridge within the region of the amino acid positions 44 to 53 compared to the unmodified streptavidin (mutein) is (independently from the method used to determine the binding affinity) in general at least by a factor of 1.1, preferably at least by a factor of 1.2, more preferably at least by a factor of 1.5, more preferably at least by a factor of 2, more preferably at by least a factor of 3, more preferably at least by a factor of 5, more preferably at least by a factor of 10, and even more preferably at least by a factor of 20.

Preferred streptavidin muteins according to the invention comprise at least one disulfide bridge formed by cysteine residues at positions 45 and 52, thereby connecting these amino acid positions 45 and 52. In such embodiments, amino acid 44 is typically glycine or alanine and amino acid 46 is typically alanine or more preferably glycine and amino acid 47 is typically arginine.

Other preferred streptavidin muteins according to the invention comprise at least one mutation at the amino acid positions 117, 120 and 121 and/or comprise a deletion of amino acids 118 and 119 and substitution of at least of amino acid position 121.

It is clear from the present invention that deletion of amino acids in loops are not only tolerated but may be even favorable for improved Strep-Tag®II binding affinity so that streptavidin muteins containing additional deletions, substitutions or additions outside the preferred changes at the positions specified within the present invention for higher binding affinity fall also within the scope of the present invention.

Thus, the term "mutation" as used herein also includes a deletion of an amino acid residue. In this respect, it is however noted that a streptavidin mutein in which the entire loop of the amino acids 114 to 121 of streptavidin (TTE-ANAWK, SEQ ID NO: 195) or the loop region of amino acids 115 to 121 of streptavidin (TEANAWK, SEQ ID NO: 196) is deleted is not encompassed in the present invention. Rather in muteins that contain one or more mutations within the segment of amino acids 115 to 121, at least one amino acid is present at one of the position 115 to 121. In some of these embodiments, an amino acid is present at positions 117, 118, 119, 120 and 121 while the amino acid at position 118 and/or 119 is deleted. Thus, in such muteins the segment formed by sequence positions 115 to 121 is shorted by either one or two amino acids. In line with the above disclosure that muteins in which the entire segment of amino acids 115 to 121 is deleted are not encompassed in the present invention, the muteins of streptavidin as described in Fletcher et al, Journal of Biotechnology 2003, are not encompassed by the present invention. This means that the following streptavidin muteins are excluded: 1. A mutein in which the wild type amino acid residues Thr-Thr-Glu-Asp-Asn-Ala-Trp-Lys (TTEANAWK, SEQ ID NO: 195) at sequence positions 114 to 121 are deleted. This mutein is designated SAPV in Fletcher et al. 2. The two muteins designated SAPV-Alb5 and SAPV-84 in Fletcher et al in which the deleted nine amino acid residues Thr-Thr-Glu-Asp-Asn-Ala-Trp-Lys (SEQ ID NO: 195) are replaced by the amino acid sequence HPYFYAPELLFFAK (SEQ ID NO: 197) or EGGKETLTPSELRDLV (SEQ ID NO 198).

Preferred streptavidin muteins according to the invention are derived from streptavidin variants which are shortened at the N- or/and the C-terminus. The minimal streptavidins which are N- and C-terminally shortened known from the state of the art are particularly preferred. A preferred polypeptide according to the present invention comprises outside of the mutagenized region the amino acid sequence of a minimal streptavidin which begins N-terminally in the region of the amino acid positions 10 to 16 and terminates C-terminally in the region of the amino acid positions 133 to 142. The polypeptide particularly preferable corresponds to a minimal streptavidin outside of the mutation region which comprises an amino acid sequence from position Ala13 to Ser139 and optionally has an N-terminal methionine residue instead of Ala13. In this application the numbering of amino acid positions refers throughout to the numbering of wt-streptavidin (Argarana et al., Nucleic Acids Res. 14 (1986), 1871-1882, cf. also FIG. 3).

Streptavidin muteins carrying one or more mutations in the region of the amino acid positions 115 to 121 according to the invention that are especially preferred are characterized in different subclasses.

First, amino acids that are found at positions 117, 120, and 121 have to be regarded separately depending on the presence or non-presence of the deletion of the two amino acids at positions 118 and 119. Amino acids that are found at positions 117, 120, and 121 in these two different cases and which, therefore, may contribute to improved affinity in each case, are summarized in FIG. 2A.

Muteins without deletion may be characterized as follows: They carry at position 117 most preferably a large hydrophobic residue like Trp, Tyr or Phe or a charged residue like Glu, Asp or Arg or a hydrophilic residue like Asn or Gln, or, less preferred, the hydrophobic residues Leu, Met or Ala, or the polar residues Thr, Ser or His, in combination with i) a small residue like Ser or Ala or, most preferably, Gly at position 120 which is then combined with a hydrophobic residue at position 121, most preferably with a bulky hydrophobic residue like Trp, Tyr or Phe or in combination with ii) a hydrophobic residue at position 120 which is Leu, Ile, Met, or Val or, more preferably, Tyr or Phe, which is then combined with a small residue like Gly, Ala, or Ser, or with Gln, or with a hydrophobic residue like Leu, Val, lie, Trp, Tyr, Phe, or Met at position 121.

Muteins with deleted amino acid positions 118 and 119 may be characterized as follows: Position 117 may be any amino acid with bulky hydrophobic residues like Phe, Tyr or Trp being less preferred and position 120 is then most preferably a Trp and less preferably Val and position 121 is also a hydrophobic amino acid, most preferably Met, Leu, Tyr or Phe, or position 121 is a small hydrophilic residue, most preferably Ser or Thr, or position 121 is Arg. An overview of identified specific mutein sequences in combination with the randomized positions and a qualification of the obtained signal intensity in the filter sandwich screening assay is shown in Tables 1-7.

In some embodiments, a streptavidin mutein of the invention has a first sequence motif for positions 117, 120, and 121 at the sequence 117 to 121 of the wild type sequence that comprises a Gly residue at sequence position 120 ($Gly^{120}$) as most important feature. Such a motif carries preferably a Phe or a Tyr, or less preferably a Met residue at sequence position 121 and a Glu, an Asp, an Arg, a His, a Leu, a Met, an Asn, a Gln, a Thr or a Ser residue at sequence position 117, position 117 thus being more variable in this motif. Such a mutein may have the wild type streptavidin amino acid $Asn^{118}$ and/or $Ala^{119}$ at sequence positions 118 and 119 (cf. the experimental section in which neither $Asn^{118}$ nor $Ala^{119}$ was subjected to mutagenesis but kept constant for the screening experiments, see also FIG. 2B). It is however also within the scope of the present invention that $Asn^{118}$ and $Ala^{119}$ are replaced by another amino acid residue. This mutation might be either a conservative substitution (replacing $Asn^{118}$ by Gln or Asp, for example, or $Ala^{119}$ by Ser, Val or lie, for example) or a non-conservative substitution (replacing $Asn^{118}$ by a positively charged or hydrophobic amino acid residue, for example). This motif1 may be thus characterized by the following consensus sequence1: $Xaa^{117}Gly^{120}Yaa^{121}$, wherein Xaa may be any amino acid and Yaa may be Phe or Tyr or Met.

In a second sequence motif for positions 117 to 121 a streptavidin mutein disclosed here comprises a hydrophobic or aromatic amino acid residue at sequence position 120. This hydrophobic or aromatic amino acid at sequence position 120 is preferably a Tyr, a Phe, a Leu, an lie or a Met. In this second sequence motif, a hydrophobic or aromatic amino acid may also be present (independently selected from position 120) at sequence position 121. Preferred residues at position 121 are Leu, lie, and Met, less preferred are a Gly, a Gln, a Trp, a Ser, an Ala or a Val. In addition, such a mutein may also have, independent from the sequence positions 120 and 121, a mutation at sequence position 117. Preferred mutations at sequence position 117 are a Tyr or a Phe, less preferred are an Arg, a Trp or a Gn residue. Also such a mutein of this second sequence motif may either have the wild type streptavidin amino acid $Asn^{118}$ and/or $Ala^{19}$ or a mutated residue at sequence positions 118 and 119. This motif2 may be thus characterized by the following consensus sequence2: $Aaa^{117}Baa^{120}Caa^{121}$, wherein Aaa may be Tyr, Phe, Arg, Trp or Gln, Baa may be Tyr, Phe, Leu, lie or Met and Caa may be any amino acid.

In a third sequence motif for streptavidin muteins disclosed here having mutations at sequence positions 117 to 121 the residues at sequence positons 118 and 119 are deleted. In this context, at sequence position 117 a His, a Glu, a Gln, a Thr, an Arg, an Asn, a Lys, a Ser, an Ala or an lie residue are preferred, at sequence position 120, the highly preferred amino acid is then a Trp or, less preferred, a Val residue and at sequence position 121 a Tyr, a Leu, a Met, a Thr, a Ser, a Phe or an Arg residue are preferred. This motif3 may be thus characterized by the following consensus sequence3: $Daa^{117}Eaa^{118}Faa^{119}Gaa^{120}Haa^{121}$, wherein Daa and Haa may be any amino acid and Eaa and Faa are both deleted and Gaa may be Trp or Val.

As can be seen in Tables 3 to 7, also streptavidin muteins with improved affinity were found that are not comprised by one of consensus sequences 1 to 3 so that the consensus sequences 1 to 3 cannot be regarded as limiting.

As disclosed by Tables 1 to 7, illustrative streptavidin muteins of the invention have one of the sequences of any of SEQ ID NOs: 18 to 97. at sequence positions 44 to 53 and/or at sequence positions 117 to 121 of the amino acid sequence of wild type streptavidin. These streptavidin muteins can any either the wildtype streptavidin sequence at any of the other sequence positions or the sequence of any known streptavidin muteins, for example, the sequence of the known muteins "1" or "2" that comprise the amino acid sequence $Val^{44}$-$Thr^{45}$-$Ala^{46}$-$Arg^{47}$ (SEQ ID NO: 98) or $Ile^{44}$-$Gly^{45}$-$Ala^{46}$-$Arg^{47}$ (SEQ ID NO: 99) at amino acid positions 44 to 47.

In some embodiments of the invention a mutein comprises the amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64 or SEQ ID NO: 65 at sequence positions 117 to 121 and either the wild-type streptavidin sequence, the sequence of mutein "1" or of mutein "2" at any other position.

In other illustrative embodiments, the streptavidin muteins of the invention may comprise or consist of the sequence of any of the following muteins that are shown in FIG. 4: m400, m402, m4001, mutein"1"-m36, mutein"1"-m23, mutein"1"-m41, mutein"1"-m4, mutein"1"-m12, mutein"1"-m22, mutein"1"-m31, mutein"1"-m32, mutein"1"-m35, mutein"1"-m38, mutein"1"-m40, mutein"1"-m42, mutein"1"-m45, mutein"1"-m46, mutein"1"-m47, mutein"1"-m7, mutein"1"-m10, mutein"1"-m17, mutein"1"-m21, mutein"1"-m24, mutein"1"-m27, mutein"1"-m28, mutein"1"-m30, mutein"1"-m33, mutein"1"-m1, mutein"1"-m3, mutein"1"-m8, mutein"1"-m15, mutein"1"-m6, mutein"1"-m9, mutein"1"-m20, mutein"1"-m34, mutein"1"-m14, mutein"1"-m18, mutein"1"-m19, m4001-m8, m4001-m21, m4001-m9, m4001-m1, m4001-m2, m4001-m3, m4001-m5, m4001-m13, m4001-m14, m4001-m24, m4001-m4, m4001-m6, m4001-m7, m4001-m10, m4001-m15, m4001-m23, m4001-m17, m4001-m12, m4001-m20, mutein"1"-m101, mutein"1"-m106, mutein"1"-m111, mutein"1"-m100, mutein"1"-m110, mutein"1"-m104, mutein"1"-m108, mutein"1"-m207, mutein"1"-m212, mutein"1"-m202, mutein"1"-m204, mutein"1"-m206, mutein"1"-m208, mutein"1"-m203, mutein"1"-m209, mutein"1"-m200, mutein"1"-m201, mutein"1"-m211, mutein"1"-m300, mutein"1"-m301, mutein"1"-m302, mutein"1"-m303, mutein"1"-m304 and m1-9.

For practical use of the muteins of the invention (for example, for affinity chromatography) it may be desirable to employ a ligand which, due to a higher binding affinity or/and due to being present at higher concentrations than the streptavidin binding peptide, can detach the binding of the streptavidin binding peptide (for example, a Strep-Tag®(II) peptide or a Di-tag peptide as described herein) from the streptavidin mutein according to the invention. Usually this ligand acts as competitor of the Strep-Tag® peptide. This (competitive) ligand is usually present in free form, meaning not fused to any protein or other molecule. In this manner it is possible to release (generally by competitive elution) bound streptavidin binding peptide ligands or proteins to which a streptavidin binding peptide such as the Strep-Tag® (II) peptide or a Di-tag peptide is fused under very mild elution conditions. This is, e.g., important for elution of the bound fusion protein from the streptavidin mutein affinity column or to reverse the binding of multimeric low affinity fusion proteins carrying a streptavidin binding peptide that are multimerized via a backbone of streptavidin mutein (multimers) of the present invention. Hence, in this aspect, the present invention concerns those streptavidin muteins whose binding affinity for peptide ligands is such that they can be competitively eluted by other streptavidin ligands like, e.g., biotin, iminobiotin, lipoic acid, thiobiotin, desthiobiotin, diaminobiotin, HABA (hydroxyazobenzene-benzoic acid) or/and dimethyl-HABA. The use of coloured substances such as HABA or dimethyl-HABA may have the advantage that the elution from a column can be checked visually. However, irrespective of this, the binding affinity of the streptavidin muteins of the present invention for peptide ligands, particularly for Strep-Tag®II is, as defined above, higher than that of the underlying wt-streptavidin or than that of the muteins "m1" or "m2" disclosed by U.S. Pat. No. 6,103,493. Therefore, in some embodiments higher affinity ligands like thiobiotin or biotin are preferred for sharp elution. Alternatively, also isolated peptide ligands binding to the biotin binding pocket, e.g. as described herein, may be used for competitive elution. For the sake of completeness, it is noted that the interaction/binding of a streptavidin binding peptide (that is usually fused or conjugated to a protein of interest) to a streptavidin mutein of the invention may not necessarily be disrupted by competitive elution but also by any other means that is able to disrupt this non-covalent complex. For example, if such fusion proteins are immobilized on a surface that is coated with a streptavidin mutein of the invention such as a surface plasmon resonsance chip, an ELISA plate or even a chromatography resin, the binding can be disrupted by change of the pH, for example, by addition of an base such as NaOH (cf. Examples 13 and 14). Such an approach might even be preferred for the regeneration of a surface plasmon resonsance chip or a chromatography resin.

It may be preferable for certain detection methods to use the streptavidin muteins of the present invention in a labeled form. Accordingly a further subject matter of this invention is a polypeptide according to the invention which is characterized in that it carries at least one label. Suitable labeling groups are known to a person skilled in the art and comprise the usual radiolabels, fluorescent labels, luminescent labels and chromophore labels as well as substances and enzymes which generate a substance that can be determined in a chemical or enzymatic reaction. In this connection all labels known for wt-streptavidin can also be coupled to the streptavidin muteins according to the present invention.

A further aspect of the present invention concerns a nucleic acid which comprises a sequence coding for a streptavidin mutein of the present invention. Such a nucleic acid is optionally operatively linked to a sequence coding for a signal peptide and, in a particular embodiment, the sequence coding for the signal peptide is the sequence for the OmpA signal peptide. Moreover it is also possible to use other signal peptides and this may even be preferable especially depending on the expression system or host cell used. A large number of such signal peptides are known in the state of the art and will not be elucidated in detail here. However, cytoplasmic expression is preferred, i.e. with a start methionine instead of the signal sequence (cf. Schmidt & Skerra, J. Chromatogr. A 676 (1994), 337-345).

A further aspect of the present invention concerns a vector which contains at least one copy of an aforementioned nucleic acid in an operatively functional environment. An operatively functional environment is understood as those elements which enable, favor, facilitate or/and increase the expression, i.e. transcription or/and a subsequent processing, of the mRNA. Examples of such elements are promoters, enhancers, transcription initiation sites and termination sites, translation initiation sites, polyA-sites etc.

The vector is selected depending on the intended expression system and for this single copy plasmids, multi-copy plasmids as well as vehicles which facilitate an integration of the nucleic acid into the host genome come into consideration. A large number of suitable vectors are known from the state of the art and will not be described in detail here. They optionally contain standard elements used for vectors such as resistances, selection markers or/and elements which for example enable an amplification of the nucleic acid or the induction of expression.

A further aspect of the present invention concerns a cell which is transformed or transfected with such a vector which carries as an insert at least one copy of a nucleic acid sequence coding for a streptavidin mutein according to the invention. The selection of the cell is not particularly critical and in general it is possible to use any cells that are suitable for such purposes. Prokaryotic as well as eukaryotic cells and yeasts come into consideration. For practical reasons prokaryotic cells are generally preferred and in particular *E. coli* for the expression of an unglycosylated protein as in the present case.

Yet a further aspect of the present invention concerns a process for the production of a streptavidin mutein according to the invention which is characterized by the following steps:

(a) transforming a suitable host cell with a vector which contains a nucleic acid coding for the streptavidin mutein,
(b) culturing the host cell under conditions in which an expression of the streptavidin mutein takes place,
(c) isolating the polypeptide.

With respect to the production process streptavidin muteins according to the invention may have a toxic effect due to their ability to bind to endogeneous biotin. Hence, when culturing the host cell the conditions should be selected such that the expression product that forms is either transported from the inside of the host cell used, for example, into the periplasm or into the culture medium by means of a suitable signal sequence or it aggregates inside the cell in the form of insoluble inclusion bodies. In the former case the streptavidin mutein according to the invention can be isolated from the periplasmic cell fraction or the cell supernatant whereas in the latter case, step (c) of the process according to the invention comprises the lysis of host cells, the isolation of the streptavidin mutein in the form of inclusion bodies and the renaturation of the streptavidin mutein. In this case *E. coli* is preferred as the host cell.

The practical applications for the streptavidin muteins or the streptavidin mutein/peptide ligand system according to the invention are essentially the same as those for conventional streptavidin/biotin or streptavidin/peptide ligand systems. There are advantages especially in situations in which a higher binding strength is desired than that between the native streptavidin or muteins as disclosed by U.S. Pat. No. 6,103,493 and the peptide ligand or in situations in which it is not possible to biotinylate a substrate of interest or is less easy than the corresponding linkage to a peptide ligand.

The advantages over the conventional streptavidin/biotin system or over the system as disclosed by U.S. Pat. No. 6,103,493 apply in particular to affinity chromatography and in purification, isolation or determination methods for recombinant proteins. Accordingly the invention also concerns the use of a streptavidin mutein according to the invention in a method for the isolation, purification, detection or immobilisation of a protein that is fused with a) a peptide sequence of the formula Trp-Xaa-His-Pro-Gln-Phe-Yaa-Zaa in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gn-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg. Affinity peptides with such an sequential arrangement of at least two streptavidin binding modules are known from International Patent Application WO02/077018 or U.S. Pat. No. 7,981,632. In this method of isolating, purifying or detecting, a liquid containing the protein to be isolated or purified is contacted with the optionally immobilized streptavidin mutein under suitable conditions in order to bind the peptide sequence to the streptavidin mutein, the resulting complex is separated from the liquid and the protein is released from the complex or detected. In some embodiments, the peptide sequence is preferably the Strep-Tag®II. In other embodiments, the peptide sequence is preferably the di-tag3 sequence (WSHPQFEKGGGSGGGSGGGSWSHPQFEK; SEQ ID NO: 103), the di-tag2 sequence Trp-Ser-His-Pro-Gln-Phe-Glu-Lys-(GlyGlyGlySer)$_2$-Trp-Ser-His-Pro-Gln-Phe-Glu-Lys (SEQ ID NO: 109) that are described in International Patent Application WO02/077018 or U.S. Pat. No. 7,981,632 or the sequence WSHPQFEKGGGSGGGSGGGSAWSHPQFEK (SEQ ID NO: 110). The peptide sequence is preferably fused to the N- or/and C-terminus of the protein. The streptavidin mutein can be bound to a solid phase or can be capable of binding to it.

An advantage of utilizing the streptavidin mutein/peptide ligand system according to the invention in an isolation or purification method is that very mild conditions can be used to elute the fusion protein carrying the peptide ligand. Hence it is possible to incubate a solid phase coupled to the streptavidin mutein, such as for example an affinity chromatography column to which the fusion protein has been adsorbed, with an adequate concentration of a ligand selected from biotin and derivatives thereof in order to release the fusion protein from the complex again. In this connection the use of biotin has proven to be particularly advantageous.

The streptavidin muteins according to the invention can be used in detection methods in an essentially similar manner to the corresponding methods that are known for conventional streptavidin. A further application is the qualitative or quantitative determination of a protein which is fused with a) a peptide sequence of the formula Trp-Xaa-His-Pro-Gln-Phe-Yaa-Zaa in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gn-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg. In this method the protein to be determined is contacted under suitable conditions with a labeled streptavidin mutein in order to bind the peptide sequence to the streptavidin mutein, is washed and the label is determined. Such a determination method can for example be carried out qualitatively to detect proteins in Western blots or quantitatively as in an ELISA. Suitable labels are all known radioactive and non-radio-active labeling groups e.g. luminescent groups, enzymes, metals, metal complexes etc. The streptavidin can be directly labeled e.g. by covalent coupling. However, indirect labels such as labeled anti-streptavidin antibodies or biotinylated enzymes etc. can also be used.

The advantages over the conventional streptavidin/biotin system or over the system disclosed by U.S. Pat. No. 6,103,493 apply also in particular to affinity chromatography and in purification, isolation or determination methods of cells, preferably mammalian cells. A preferred use in this context is its use to multimerize low affinity ligands (for example, including but not limited to Fab fragments or MHC I molecules), for specific cell surface receptors fused to a peptide sequence of the formula Trp-Xaa-His-Pro-Gln-Phe-Yaa-Zaa in which Xaa represents an arbitrary amino acid and Yaa and Zaa either both denote Gly or Yaa denotes Glu and Zaa denotes Arg or Lys. This use is further described in U.S. Pat. No. 7,776,562 or 8,298,782 for streptavidin muteins disclosed in U.S. Pat. No. 6,103,493. It is also possible to use for this multimerization/reversibly staining or isolation of cells an affinity ligand that is fused to a sequentially arranged streptavidin binding module such as the di-tag3 sequence (WSHPQFEKGGGSGGGSGGGSWSHPQFEK; SEQ ID NO: 103) or any other such sequence described in International Patent Application WO02/077018 or U.S. Pat. No. 7,981,632 together with a streptavidin mutein of the invention. The higher affinity of streptavidin muteins of the present inventions provides multimeric reagents of improved stability and applicability. To be useful in such cell purification applications, the muteins of the present invention are preferably multimerized and optionally directly labeled with a fluorescent dye or immobilized on a magnetic bead or on any other solid support. The magnetic bead may be a micro or a nano bead and the other solid support may be a resin as used in column chromatography to pursue a column purification approach for cell purification.

A further advantageous aspect of the invention is the use of the streptavidin muteins according to the invention to immobilize a protein which is fused with a) a peptide sequence Trp-Xaa-His-Pro-Gln-Phe-Yaa-Zaa (SEQ ID NO: 101) in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gn-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg. In one embodiment, the peptide sequence is the sequence (WSHPQFEKGGGSGGGSGGGSWSHPQFEK; SEQ ID NO: 103). In another embodiment, the peptide sequence is the sequence WSHPQFEKGGGSGGGSGG-SAWSHPQFEK (SEQ ID NO: 110). This immobilization is preferably carried out on solid phases coated with streptavidin muteins of the invention such as microtitre plates, beads (e.g. made of agarose or other polymers like, e.g., polymethacrylate), microbeads made of organic or paramagnetic materials, nanobeads made of organic or paramagnetic materials or sensor chips such as Biacore™ chips or other support as e.g. used for lateral flow assays or for making protein arrays.

In addition, it is of course also possible to use the streptavidin muteins according to the invention in a conventional streptavidin/biotin (derivative) system. In other words this means the use of the streptavidin muteins according to the invention to determine or isolate substances which carry a group capable of binding to streptavidin. If only a part of the wt-streptavidin is replaced by the streptavidin muteins according to the invention, particular effects can be achieved in this connection via the formation of mixed tetramers.

Yet a further aspect of the invention also concerns a reagent kit which contains a streptavidin mutein according to the invention and optionally standard buffer and auxiliary substances and additives. Such a reagent kit is in particular intended to be used in one of the isolation, purification, assay or determination methods described above. However, the kit is also suitable for other methods in which the conventional streptavidin/biotin system is used e.g. for nucleic acid hybridization assays or immunoassays. The reagent kit can contain the streptavidin mutein according to the invention as free, non-modified protein or/and in a solid phase-bound or/and labeled form.

The invention is further illustrated by the following tables, figures and examples:

BRIEF DESCRIPTION OF THE TABLES

TABLES 1-7 show overviews of the different streptavidin mutein sequences resulting from the screening of the different libraries 1-7, respectively, incl. the relative signal intensities obtained from the different streptavidin muteins in the filter sandwich assay. The randomized positions are indicated with Xaa. For comparison, the amino acids of wt streptavidin and of streptavidin mutein "1" of U.S. Pat. No. 6,103,493 at the corresponding positions are given (except Table 4, showing the results of library 4 where the same sequence is denoted to be of m4001 of the present invention because these muteins are derived from m4001 and not from mutein"1" of U.S. Pat. No. 6,103,493). Thus, all muteins shown in Tables 3 and 5-7 are derived from and thus identical with mutein "1" of U.S. Pat. No. 6,103,493 with respect to the region of amino acid positions 44-53. The muteins of Table 4 are derived from and thus identical with mutein m4001 of the present invention with respect to the region of amino acid positions 44-53;

TABLE 8 shows on top the binding affinity results as determined by the ELISA described in Example 10 for the complex between Strep-Tag®II fused to bacterial alkaline phosphatase (BAP-StrepII) and a selection of the streptavidin muteins of the present invention, which are for those mutated in the region of amino acids 117-121 all derived from mutein "1" of U.S. Pat. No. 6,103,493 for amino acid positions 44-53 (and not from the disulfide containing mutein m4001 of the present invention shown in Table 4) in comparison to mutein "1" of U.S. Pat. No. 6,103,493 and m402 and 4001 of the present invention which are mutated in the region of amino acid positions 44-53 only. On the bottom of Table 8 highlighted in grey, the binding affinity results determined by a different ELISA experiment using the same protocol are shown for mutein m1-9 in comparison to m4001, m4, and m23 shown above. The absolute affinity results indicate slightly lower affinity data than those obtained for the same streptavidin muteins in the experiment shown above. This nevertheless demonstrates that affinity of m1-9 is also improved over mutein "1" in this ELISA assay characterizing binding to Strep-Tag®II when fused to bacterial alkaline phosphatase (BAP-StrepII).

TABLE 9 shows the binding affinity results as determined by the affinity chromatography experiment for retention of cytochromeb562 with C-terminally fused Strep-tagII after overload and subsequent defined washing on Sepharose columns with different immobilized streptavidin muteins of the present invention, which are for those mutated in the region of amino acids 117-121 all derived from mutein "1" of U.S. Pat. No. 6,103,493 for amino acid positions 44-53 (and not from the disulfide containing mutein m4001 of the present invention), in comparison to mutein "1" of U.S. Pat. No. 6,103,493, m402 and 4001 of the present invention which are mutated in the region of amino acid positions 44-53 only and in comparison to wt streptavidin;

TABLE 10 shows the binding affinity results as determined by the affinity chromatography experiment for capture of cytochromeb562 with C-terminally fused Strep-tagII out of a dilute solution on Sepharose columns with different immobilized streptavidin muteins of the present invention, which are for those mutated in the region of amino acids 117-121 all derived from mutein "1" of U.S. Pat. No. 6,103,493 for amino acid positions 44-53 (and not from the disulfide containing mutein m4001 of the present invention), in comparison to mutein "1" of U.S. Pat. No. 6,103,493, m402 and 4001 of the present invention which are mutated in the region of amino acid positions 44-53 only and in comparison to wt streptavidin.

TABLE 11 shows the results of kinetic affinity measurements via BiaCore™ for the streptavidin mutein "1" (this known streptavidin mutein has the sequence shown on top of FIG. 4, second line (column 2) and the mutein m1-9. The mutein m1-9 is shown as last mutein in FIG. 4 and is a streptavidin mutein having the amino acids Glu, Gly, Tyr at positions 117, 120, 121, respectively, and otherwise the sequence of mutein "1" (column 2). For the BioCore™ measurement, carboxyl groups on a BiaCore™ S-CM5 sensor chip were activated with standard EDC/NHS chemistry and mutein "1" or mutein m1-9 were coupled via amino groups at 2 different densities using 10 mM acetate pH 5.0 as buffer. The resulting relative immobilized amounts are given in RU (arbitrary units) (column 3). To achieve the low density immobilization both muteins were applied applied at a concentration of 1 μg/ml and a flow rate of 10 μl/min. To achieve the immobilization at higher density, mutein m1-9 was used at a concentration of 20 μg/ml and mutein "1" was used at a concentration of 50 μg/ml. The interaction of such immobilized mutein "1" or mutein m1-9 with 4 different recombinantly expressed and via Strep-Tactin affinity chromatography purified fusion proteins, namely Green Fluorescent Protein (GFP) with either the streptavidin binding peptide Strep-tagII (GFP-StrepII, SEQ ID NO: 104) or the streptavidin binding peptide di-tag3 (GFP-di-tag3, SEQ ID NO: 105) and cytochrome b562 with either the Strep-tagII (Cytb562-StrepII, SEQ ID NO: 106) or the di-tag3 (Cytb562-di-tag3, SEQ ID NO: 107) at the respective C-terminal end (column 1; see Appendix 1 for amino acid sequences as deduced from the recombinant genes), was analyzed at 25° C. on a Biacore T100 instrument using 10 mM HEPES (pH 7.4), 150 mM NaCl, 3.4 mM EDTA, 0.005% Tween 20 as running buffer. Prior to analysis, the fusion protein preparations were dialyzed against Buffer W (100 mM Tris-Cl pH8, 150 mM NaCl, 1 mM EDTA), and checked via analytical size exclusion chromatography to be essentially free of aggregates (a content of max. 5% was accepted, in most cases it was below 1%) to ensure to measure the interaction of monovalent fusion proteins with immobilized streptavidin muteins only. Interaction of 170 or 4350 RU mutein m1-9 was analyzed with Cytb562-StrepII at concentrations of 74, 222, 667, 2000 and 6000 nM; Interaction of 170 or 4350 RU mutein m1-9 was analyzed with Cytb562-di-tag3 at concentrations of 1.2, 3.7, 11.1, 33.3 and 100 nM; Interaction of 170 or 4350 RU mutein m1-9 was analyzed with GFP-StrepII at concentrations of 11.1, 33.3, 100, 300 and 900 nM; Interaction of 170 or 4350 RU mutein m1-9 was analyzed with GFP-di-tag3 at concentrations of 3.7, 11.1, 33.3, 100 and 300 nM; Interaction of 325 or 5567 RU mutein "1" was analyzed with Cytb562-StrepII or Cytb562-di-tag3 at concentrations of 0.22, 0.66, 2, 6 and 18 µM each; Interaction of 325 or 5567 RU mutein "1" was analyzed with GFP-StrepII or GFP-di-tag3 at concentrations of 11.1, 33.3, 100, 300 and 900 nM each. Data were fitted using the kinetic global fit (Langmuir 1:1) and resulting on- and off-rates and deduced dissociation constants are shown in column 4, column 5 and column 6, respectively. BiaCore data were measured by Biaffin GmbH & Co KG, Kassel, Germany.

TABLE 12 shows the results of repeated cycles of affinity chromatography with crude lysates (*E. coli*) for a GFP-StrepII fusion protein: The yield and purity of the fusion protein were determined by analyzing the eluate of the column after addition of 10 mM biotin in Buffer W on a Bioanalyzer 2100 instrument (Agilent Technologies Inc.).

TABLE 13 is a concordance table indicating the sequence identifier that has been assigned to each of the nucleotide and peptide sequences disclosed in the present application.

BRIEF DESCRIPTION OF THE FIGURES

FIG. 1A shows the improved affinity of the disulfide containing streptavidin mutein m4001 of the present invention shown in Table 2 for the peptide ligand Strep-Tag®II in an ELISA as compared to streptavidin mutein "1" disclosed by U.S. Pat. No. 6,103,493.

For this rows of an ELISA plate were each coated with equivalent concentrations of the respective recombinant streptavidin mutein "1" (rhombus) and m4001 (triangles). After saturating with BSA and washing, the wells were incubated with a purified fusion protein consisting of *E. coli* alkaline phosphatase Strep-Tag®II fusion protein (BAP-StrepII)—expressed by pASK75-phoA, the sequence of which is disclosed by SEQ ID NO. 1, and purified by Strep-Tactin® affinity chromatography—at the concentrations shown in the graph. After washing to remove unbound protein, the activity of bound BAP-StrepII fusion protein was measured in the presence of p-nitrophenyl phosphate. The data were fitted by non-linear regression by the least squared error method. The following $K_D$ values were obtained: 0.11 µM for streptavidin mutein "1" of U.S. Pat. No. 6,103,493 and 0.02 µM for m4001. The fitted values for each concentration are shown as well for m4001 (+) and streptavidin mutein "1" of U.S. Pat. No. 6,103,493 (x) demonstrating that experimental data and fit are in good agreement.

Figure 1A:
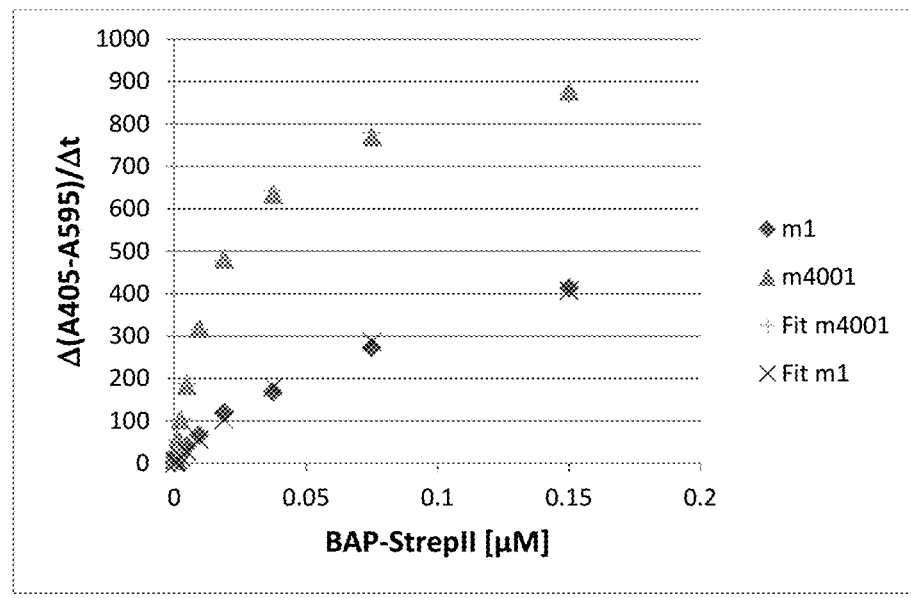
FIGS. 1A-1B show two graphs each showing the binding affinity of recombinant streptavidin mutein "1" disclosed in U.S. Pat. No. 6,103,493 compared to two selected streptavidin muteins according to the present invention in an ELISA.
Figure 1B:
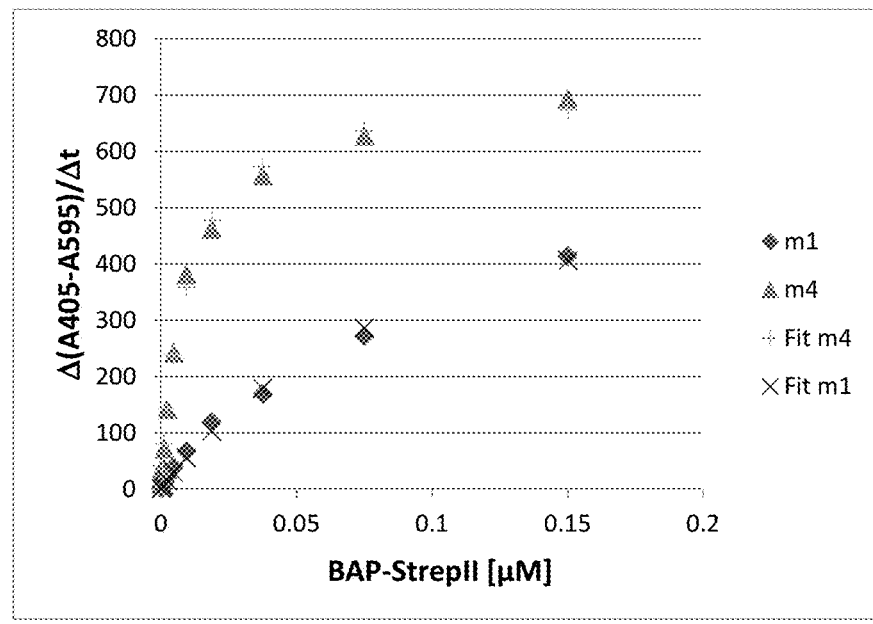

FIG. 1B shows the improved affinity of the streptavidin mutein m4 of the present invention shown in Table 3 for the peptide ligand Strep-Tag®II in an ELISA when compared to streptavidin mutein "1" disclosed by U.S. Pat. No. 6,103,493. For this rows of an ELISA plate were each coated with equivalent concentrations of the respective recombinant streptavidin mutein "1" (rhombus) and m4 (triangles). After saturating with BSA and washing, the wells were incubated with a purified fusion protein consisting of *E. coli* alkaline phosphatase Strep-Tag®II fusion protein (BAP-StrepII)—expressed by pASK75-phoA, the sequence of which is disclosed by SEQ ID NO. 1, and purified by Strep-Tactin® affinity chromatography—at the concentrations shown in the graph. After washing to remove unbound protein, the activity of bound BAP-StrepII fusion protein was measured in the presence of p-nitrophenyl phosphate. The data were fitted by non-linear regression by the least squared error method. The following $K_D$ values were obtained: 0.11 µM for mutein "1" of U.S. Pat. No. 6,103,493 and 0.009 µM for m4. The fitted values for each concentration are shown as well for m4 (+) and streptavidin mutein "1" of U.S. Pat. No. 6,103,493 (x) demonstrating that experimental data and fit are in good agreement.

FIG. 2A shows a non limiting overview about the mutations at sequence positions 117 to 121 found in streptavidin muteins of the invention in which amino acid positions were subjected to mutagenesis. FIG. 2A shows the mutations found in muteins in which amino acid residues 118 and 119 were present and also found in muteins in which amino acid residues 118 and 119 were deleted.

FIG. 2B shows the sequence motives of muteins of the invention having at least one mutation within the peptide segment of residues 117 to 121 of the streptavidin sequence. Preferred residues are shown in bold print, less preferred residues are shown in normal print. Amino acid residues shall be considered positionwise and each may be in principle combined with any other occurring at another position. Sequence motif 1 is characterized in that glycine is highly preferred at position 120 and may be combined with a large hydrophobic residue, preferably tyrosine or phenylalanine, or, less preferably, methionine at position 121 and a charged, preferably glutamate, aspartate, arginine or histidine, or, less preferably, a hydrophilic residue like glutamine, asparagine, serine or threonine or a hydrophobic residue like leucine or methionine at position 117. Sequence motif 2 is characterized in that a large hydrophobic residue, preferably tyrosine or phenylalanine but not tryptophane is highly preferred at position 120 instead of small glycine while leucine, isoleucine or methionine are less preferred at this position 120. Then also hydrophobic residues are preferred at positions 117 and 121, whereby aromatic tyrosine or phenylalanine are preferred for position 117 and large but non-aromatic hydrophobic residues, most preferably leucine, isoleucine and methionine, are preferred for position 121. Less preferred for position 117 are the residues arginine, tryptophane or glutamine and for position 121 the residues glutamine, glycine, tryptophane, serine, alanine or valine. Sequence motif 3 is characterized in that amino acids at positions 118 and 119 are deleted. In this case, tryptophane at original position 120 is strongly preferred and valine is less preferred and these residues may be combined with preferably tyrosine at position 121, whereby also other residues like leucine, methionine, threonine, serine, phenylalanine or arginine may occur at position 121, and with most preferably a hydrogen bond acceptor and/or donator like histidine, glutamine or glutamate or, less preferably also other residues like threonine, arginine, asparagine, lysine, serine, alanine or isoleucine at position 117.

FIG. 3 shows the amino acid sequence of sequence positions 14 to 139 of wild-type streptavidin (SEQ ID NO: 15).

FIG. 4 shows the amino acid sequence of all muteins experimentally generated and characterised herein aligned with the amino acid sequence of amino acid positions 14 to 139 of wild type streptavidin and of the muteins "1" and "2" described in U.S. Pat. No. 6,103,493. When the muteins were secreted by *E. coli* to the periplasm, as done during screening within the filter sandwich assay, the resulting protein sequences were produced with an additional alanine at the N-terminal end (position 13). When the muteins were produced by *E. coli* in the cytosol as inclusion bodies for subsequent refolding, purification and analysis, the resulting protein sequences were produced as shown with an additional methionine at the N-terminal end (position 13). Deleted amino acids are indicated by a dash (-). Amino acid numbering has been conducted in case of deletions in a manner maintaining comparability at equivalent positions. It has, however, to be noted that the molecules containing deletions are decreased in length by the number of deletions which is 2 for the corresponding muteins of FIG. 4. This means that the muteins of FIG. 4 without deletions contain a total of 127 amino acids while those with deletions contain a total of 125 amino acids. The amino acid residues resulting from randomized codons in the different libraries are shown in bold. The sequence identifiers corresponding to the amino acid sequences depicted in FIG. 4 are as follows:

SEQ ID NO: 212 wildtype (Wt) streptavidin,
SEQ ID NO: 112 mutein"1",
SEQ ID NO: 113 mutein"2",
SEQ ID NO: 114 mutein m400,
SEQ ID NO: 115 mutein m402,
SEQ ID NO: 116 mutein m4001,
SEQ ID NO: 117 mutein"1"-m36,
SEQ ID NO: 118 mutein"1"-m23,
SEQ ID NO: 119 mutein"1"-m41,
SEQ ID NO: 120 mutein"1"-m4,
SEQ ID NO: 121 mutein"1"-m12,
SEQ ID NO: 122 mutein"1"-m22,
SEQ ID NO: 123 mutein"1"-m31,
SEQ ID NO: 124 mutein"1"-m32,
SEQ ID NO: 125 mutein"1"-m35,
SEQ ID NO: 126 mutein"1"-m38,
SEQ ID NO: 127 mutein"1"-m40,
SEQ ID NO: 128 mutein"1"-m42,
SEQ ID NO: 129 mutein"1"-m45,
SEQ ID NO: 130 mutein"1"-m46,
SEQ ID NO: 131 mutein"1"-m47,
SEQ ID NO: 132 mutein"1"-m7,
SEQ ID NO: 133 mutein"1"-m10,
SEQ ID NO: 134 mutein"1"-m17,
SEQ ID NO: 135 mutein"1"-m21,
SEQ ID NO: 136 mutein"1"-m24,
SEQ ID NO: 137 mutein"1"-m27,
SEQ ID NO: 138 mutein"1"-m28,
SEQ ID NO: 139 mutein"1"-m30,
SEQ ID NO: 140 mutein"1"-m33,
SEQ ID NO: 141 mutein"1"-m1,
SEQ ID NO: 142 mutein"1"-m3,
SEQ ID NO: 143 mutein"1"-m8,
SEQ ID NO: 144 mutein"1"-m15,
SEQ ID NO: 145 mutein"1"-m6,
SEQ ID NO: 146 mutein"1"-m9,
SEQ ID NO: 147 mutein"1"-m20,
SEQ ID NO: 148 mutein"1"-m34,
SEQ ID NO: 149 mutein"1"-m14,
SEQ ID NO: 150 mutein"1"-m18,
SEQ ID NO: 151 mutein"1"-m19,
SEQ ID NO: 152 m4001-m8,
SEQ ID NO: 153 m4001-m21,
SEQ ID NO: 154 m4001-m9,
SEQ ID NO: 155 m4001-m1,
SEQ ID NO: 156 m4001-m2,
SEQ ID NO: 157 m4001-m3,
SEQ ID NO: 158 m4001-m5,
SEQ ID NO: 159 m4001-m13,
SEQ ID NO: 160 m4001-m14,
SEQ ID NO: 161 m4001-m24,
SEQ ID NO: 162 m4001-m4,
SEQ ID NO: 163 m4001-m6,
SEQ ID NO: 164 m4001-m7,
SEQ ID NO: 165 m4001-m10,
SEQ ID NO: 166 m4001-m15,
SEQ ID NO: 167 m4001-m23,
SEQ ID NO: 168 m4001-m17,
SEQ ID NO: 169 m4001-m12,
SEQ ID NO: 170 m4001-m20,
SEQ ID NO: 171 mutein"1"-m101,
SEQ ID NO: 172 mutein"1"-m106,
SEQ ID NO: 173 mutein"1"-m111,
SEQ ID NO: 174 mutein"1"-m100,
SEQ ID NO: 175 mutein"1"-m110,
SEQ ID NO: 176 mutein"1"-m104,
SEQ ID NO: 177 mutein"1"-m108,
SEQ ID NO: 178 mutein"1"-m207,
SEQ ID NO: 179 mutein"1"-m212,
SEQ ID NO: 180 mutein"1"-m202,
SEQ ID NO: 181 mutein"1"-m204,
SEQ ID NO: 182 mutein"1"-m206,
SEQ ID NO: 183 mutein"1"-m208,
SEQ ID NO: 184 mutein"1"-m203,
SEQ ID NO: 185 mutein"1"-m209,
SEQ ID NO: 186 mutein"1"-m200,
SEQ ID NO: 187 mutein"1"-m201,
SEQ ID NO: 188 mutein"1"-m211,
SEQ ID NO: 189 mutein"1"-m300,
SEQ ID NO: 190 mutein"1"-m301,
SEQ ID NO: 191 mutein"1"-m302,
SEQ ID NO: 192 mutein"1"-m303,
SEQ ID NO: 193 mutein"1"-m304, and
SEQ ID NO: 194 mutein m1-9."

EXAMPLES

General Methods

DNA manipulations were carried out by conventional genetic engineering methods (see e.g. Sambrook et al., Molecular Cloning. A Laboratory Manual (1989), Cold Spring Harbor Press). *E. coli* K12 TG1 (Stratagene) was used for library expression of secreted streptavidin muteins, *E. coli* K12 TOP10 (Life Technologies) for cloning and library expression, and *E. coli* K12 JM83 (Yanisch-Peron et al., (1985), Gene 33, 103-119) for periplasmic expression of

*E. coli* cytochromeb562 and alkaline phosphatase, both fused to Strep-tagII. Cytosolic expression of the muteins for subsequent protein isolation for coupling to Sepharose or for coating microtitre plates was carried out according to Schmidt and Skerra (1994), supra. Plasmid sequencings were carried out according to the standard dideoxy technique by Sequence Laboratories Göttingen GmbH. The primers and oligonucleotides were synthesized using an Applied Biosystems Expedite DNA synthesizer.

Example 1: Preparation of Library1

A plasmid bank with DNA sequences which code for streptavidin derivatives mutagenized in the region of amino acid positions 44 to 52 (with reference to wt-streptavidin) was prepared by PCR amplification of pASK-IBA2-SAm1 using pfu-polymerase (Fermentas) and the following primers P1 and P2:

```
P1:
                                        (SEQ ID NO. 5)
5'-TCG TGA CCG CGG GTG CAG ACG GAG CTC TGA CCG GTA
CCT ACN N(C/G)N N(G/T)G CGC GTG GCA ACG CCG AGN
N(C/G)C GCT ACG TCC TGA CCG GTC GTT
``` where the 3' terminal T was linked via a phosphorothioate bond and

```
P2:
                                        (SEQ ID NO. 6)
5'-AGT AGC GGT AAA CGG CAG A
```

DNA sequences were generated in this manner which contained 32-fold degenerated codons at each of the positions 44, 45 and 52 of streptavidin mutein "1" encoding all of the 20 amino acids or a stop codon. The resulting PCR product was purified by gel electrophoresis, cleaved with SacII and HindIII and ligated into the correspondingly cleaved vector fragment of pASK-IBA2-SAm1.

*E. coli* TOP0 cells were transformed with the vector mixture using the calcium chloride method (Sambrook et al., 1989).

Example 2: Preparation of Library2

A plasmid bank with DNA sequences which code for streptavidin derivatives mutagenized in the region of amino acid positions 44 to 52 (with reference to wt-streptavidin) was prepared by PCR amplification of pASK-IBA2-SAm1 using pfu-polymerase (Fermentas) and the following primers P2 and P3:

```
P3:
                                        (SEQ ID NO. 7)
5'-CTG ACC GGT ACC TAC G(G/C)T TGC NN(G/C) NN(G/T)
GGC AAC GCC GAG TGC CGC TAC GTC CTG A
``` where the 3' terminal A was linked via a phosphorothioate bond and

```
P2:
                                        (SEQ ID NO. 6)
5'-AGT AGC GGT AAA CGG CAG A.
```

DNA sequences were generated in this manner which contained fixed mutations Thr45→Cys and Ser52→Cys, a 2-fold degenerated codon at position 44 encoding Gly or Ala and 32-fold degenerated codons encoding all of the 20 amino acids or a stop codon at each of the positions 46 and 47 of streptavidin mutein "1". The resulting PCR product was purified by gel electrophoresis, cleaved with KpnI and HindIII and ligated into the correspondingly cleaved vector fragment of pASK-IBA2-SAm1.

*E. coli* TOP10 cells were transformed with the vector mixture using the calcium chloride method (Sambrook et al., 1989).

Example 3: Preparation of Library3

A plasmid bank with DNA sequences which code for streptavidin mutein "1" derivatives mutagenized in the region of amino acid positions 115 to 121 (with reference to wt-streptavidin) was prepared by PCR amplification of pASK-IBA2-SAm1 using PfuUltra polymerase (Stratagene) and the following primers P4 and P5:

```
P4:
                                        (SEQ ID NO. 8)
5'-GCC NN(G/C) NN(G/T) TCC ACG CTG GTC GGC CA
``` which was phosphorylated at the 5' end and

```
P5:
                                        (SEQ ID NO. 9)
5'-GTT (A/C)NN CTC GGT GGT GCC GGA GGT
``` equally phosphorylated at the 5' end.

Linear DNA sequences of the whole vector were generated in this manner which contained streptavidin mutein "1" gene variants with 32-fold degenerated codons at each of the positions 117, 120 and 121 encoding all of the 20 amino acids or a stop codon. The resulting PCR product was purified by gel electrophoresis and ligated. This strategy of amplifying the whole vector with a blunt end generating proof-reading polymerase using phosphorylated primers has the advantage that no restriction enzymes have to be used and, moreover, that a one fragment ligation can be performed which, being a monomolecular reaction, is concentration independent and more efficient than a two fragment ligation as used for the generation of libraries 1 and 2.

*E. coli* TOP0 or/and TG1 cells were transformed with the ligated vector mixture using electroporation with a Bio-Rad MicroPulser using the manufacturers standard program Ec2 (0.2 cm cuvettes; 2.5 kV).

Example 4: Preparation of Library4

A plasmid bank with DNA sequences which code for streptavidin mutein m4001 derivatives mutagenized in the region of amino acid positions 115 to 121 (with reference to wt-streptavidin) was prepared by PCR amplification of pASK-IBA2-SAm4001 using PfuUltra polymerase (Stratagene) and the following primers P4 and P5:

```
P4:
                                        (SEQ ID NO. 8)
5'-GCC NN(G/C) NN(G/T) TCC ACG CTG GTC GGC CA
``` which was phosphorylated at the 5' end and

P5:
(SEQ ID NO. 9)
5'-GTT (A/C)NN CTC GGT GGT GCC GGA GGT equally phosphorylated at the 5' end.

Linear DNA sequences of the whole vector were generated in this manner which contained streptavidin mutein m4001 gene variants with 32-fold degenerated codons at each of the positions 117, 120 and 121 encoding all of the 20 amino acids or a stop codon. The resulting PCR product was purified by gel electrophoresis and ligated.

*E. coli* TOP10 or/and TG1 cells were transformed with the ligated vector mixture using electroporation with a Bio-Rad MicroPulser using the manufacturers standard program Ec2 (0.2 cm cuvettes; 2.5 kV).

Example 5: Preparation of Library5

A plasmid bank with DNA sequences which code for streptavidin mutein "1" derivatives mutagenized in the region of amino acid positions 115 to 121 (with reference to wt-streptavidin) was prepared by PCR amplification of pASK-IBA2-SAm1 using PfuUltra polymerase (Stratagene) and the following primers P4 and P6:

P4:
(SEQ ID NO. 8)
5'-GCC NN(G/C) NN(G/T) TCC ACG CTG GTC GGC CA which was phosphorylated at the 5' end and

P6:
(SEQ ID NO. 10)
5'-GTT A(A/T)A CTC GGT GGT GCC GGA GGT equally phosphorylated at the 5' end.

Linear DNA sequences of the whole vector were generated in this manner which contained streptavidin mutein "1" gene variants with a 2-fold degenerated codon at position 117 encoding Phe or Tyr and 32-fold degenerated codons at each of the positions 120 and 121 encoding all of the 20 amino acids or a stop codon. The resulting PCR product was purified by gel electrophoresis and ligated.

*E. coli* TOP10 or/and TG1 cells were transformed with the ligated vector mixture using electroporation with a Bio-Rad MicroPulser using the manufacturers standard program Ec2 (0.2 cm cuvettes; 2.5 kV).

Example 6: Preparation of Library6

A plasmid bank with DNA sequences which code for streptavidin mutein "1" derivatives mutagenized in the region of amino acid positions 115 to 121 (with reference to wt-streptavidin) was prepared by PCR amplification of pASK-IBA2-SAm1 using PfuUltra polymerase (Stratagene) and the following primers P7 and P8:

P7:
(SEQ ID NO. 11)
5'-N(G/C)N N(G/T)T CCA CGC TGG TCG GCC AC which was phosphorylated at the 5' end and

P8:
(SEQ ID NO. 12)
5'-N(A/C)N NCT CGG TGG TGC CGG AGG T equally phosphorylated at the 5' end.

Linear DNA sequences of the whole vector were generated in this manner which contained streptavidin mutein "1" gene variants with deleted amino acid positions 118 and 119 and 32-fold degenerated codons at each of the positions 117, 120 and 121 encoding all of the 20 amino acids or a stop codon. The resulting PCR product was purified by gel electrophoresis and ligated.

*E. coli* TOP10 or/and TG1 cells were transformed with the ligated vector mixture using electroporation with a Bio-Rad MicroPulser using the manufacturers standard program Ec2 (0.2 cm cuvettes; 2.5 kV).

Example 7: Preparation of Library7

A plasmid bank with DNA sequences which code for streptavidin mutein "1" derivatives mutagenized in the region of amino acid positions 115 to 121 (with reference to wt-streptavidin) was prepared by PCR amplification of pASK-IBA2-SAm1 using PfuUltra polymerase (Stratagene) and the following primers P9 and P10:

P9:
(SEQ ID NO. 13)
5'-GGN N(G/T)T CCA CGC TGG TCG GCC AC which was phosphorylated at the 5' end and

P10:
(SEQ ID NO. 14)
5'-A(C/A)N NCT CGG TGG TGC CGG AGG T equally phosphorylated at the 5' end.

Linear DNA sequences of the whole vector were generated in this manner which contained streptavidin mutein "1" gene variants with deleted amino acid positions 118 and 119, a fixed Trp at position 120 and 32-fold degenerated codons at each of the positions 117 and 121 encoding all of the 20 amino acids or a stop codon. The resulting PCR product was purified by gel electrophoresis and ligated.

*E. coli* TOP10 or/and TG1 cells were transformed with the ligated vector mixture using electroporation with a Bio-Rad MicroPulser using the manufacturers standard program Ec2 (0.2 cm cuvettes; 2.5 kV).

Example 8: Identification of Streptavidin Muteins with an Increased Binding Affinity for Peptide Ligands in a Filter Sandwich Assay (Cf. U.S. Pat. No. 6,103,493)

In order to identify streptavidin muteins with an increased binding affinity for peptide ligands, a fusion protein was prepared comprising the alkaline phosphatase of *E. coli* (BAP) and the Strep-Tag®II peptide (WSHPQFEK) which was attached to its C-terminus as encoded by pASK75-phoA (SEQ ID NO. 1). For this pASK75-phoA was expressed with JM83 and the recombinant protein was purified as described in U.S. Pat. No. 6,103,493 with the sole difference that Strep-Tactin® instead of streptavidin affinity chromatography and using desthiobiotin instead of diaminobiotin as the eluting agent according to the procedure of Schmidt and Skerra (2007), supra, was used. Desthiobiotin was removed by dialysis prior to using the BAP-Strep-Tag®II fusion protein (also denoted BAP-StrepII) in further assays.

*E. coli* cells (TG1 or TOP10) transformed with the plasmid banks obtained in example 1-7 were plated out on nitrocellulose acetate membranes (type OE66, 110 mm diameter, Whatman) which had been placed on an agar plate containing LB medium which contained 100 μg/ml ampicillin. The membrane was incubated for 24 hours at 30° C. until colonies became visible.

During this incubation, a second membrane was prepared. An Immobilon-P membrane (Millipore) of similar size was coated at room temperature for ca. 6 hours with a total volume of 10 ml of rabbit anti-streptavidin immunoglobulin (Sigma) diluted 1:200 with PBS (4 mM KH2PO4, 16 mM Na2HPO4, 115 mM NaCl) and afterwards was blocked for ca. 2 hours in 3% w/v bovine serum albumin (BSA), 0.5% v/v Tween in PBS.

This second membrane was washed with PBS and placed on an agar plate containing LB medium which contained 100 μg/ml ampicillin and 0.2 μg/ml anhydrotetracyclin. Subsequently the nitrocellulose membrane with the colonies on the upper side was placed on the second membrane and the relative positions of the two membranes were marked. After incubation overnight at room temperature, the upper membrane with the colonies was removed and stored on a fresh LB ampicillin agar plate at 4° C. The second membrane was also removed from the agar plate and washed three times for 30 minutes while shaking in PBS/Tween (0.1% v/v Tween20 in PBS). Subsequently the membrane was admixed with 10 ml fresh PBS/Tween solution containing the purified BAP-Strep-tagII fusion protein (2 μg/ml). After incubating for one hour at room temperature, the membrane was washed again twice in PBS/Tween and twice in PBS buffer. The signal generation took place for 1 to 2 hours in the presence of 10 ml AP buffer (100 mM Tris-CI pH 8.8, 100 mM NaCl, 5 mM $MgCl_2$) with addition of 30 μl bromo-chloro-indolylphosphate (BCIP) (50 mg/ml in dimethylformamide) and 5 μl nitroblue tetrazolium (NBT) (75 mg/ml in 70% v/v dimethylformamide). The color spots which formed in this process were assigned to corresponding colonies on the first membrane. After isolation and culture of several signal generating clones, the corresponding plasmid DNA was isolated, sequenced and the deduced amino acid sequence at the randomized positions is shown in Tables 1-7 together with the relative signal intensity obtained in the filter assay described above. Signal intensities from different libraries cannot be compared as they arose from different non parallel experiments. Surprisingly, sequencing of signal positive clones from library3 unexpectedly revealed in some cases the deletion of amino acids at positions 118 and 119. These deletions can be explained by the presence of defective primers in the P4 and P5 primer preparations, each shortened at the 5' end by 3 bases.

Example 9: Production of Streptavidin Muteins on a Preparative Scale

The known expression system for recombinant minimal streptavidin (Schmidt and Skerra (1994), supra) was used to produce streptavidin muteins on a preparative scale. For this the major part of the coding region was removed from the vector pSA1 which contains the coding region of wt-streptavidin and the T7 promoter by using the singular SacII and HindIII restriction sites and replaced by the corresponding regions from the mutated pASK-IBA2-SAm1 plasmids. wt-streptavidin and the streptavidin muteins were subsequently expressed in the form of cytoplasmic inclusion bodies, solubilized, renatured and purified by fractional ammonium sulphate precipitation as described by Schmidt and Skerra (1994) supra. The purity of the obtained streptavidin muteins was checked with an Agilent 2100 Bioanalyzer. Each streptavidin mutein described in the present application was obtained at >90% purity. Disulfide formation of the cysteines at positions 45 and 52 in purified streptavidin mutein m4001 was determined to be 98.6% by probing a 234 μM solution (determined by using the theoretic molar extinction coefficient $\varepsilon_{280}$=42060 $cm^{-1}M^{-1}$ for the monomer) in comparison to a serial dilution of a reduced 1,4-dithio-D-threitol (DTT) standard with Ellman's reagent (5,5'-dithiobis-(2-nitrobenzoic acid)) and measuring absorbance at 412 nm.

Example 10: ELISA

An ELISA was carried out to determine the binding affinity of the streptavidin muteins for the peptide ligand Strep-tagII.

The wells of a 96-well microtitre plate (Costar) were coated overnight at 4° C. with 100 μl of a solution of recombinant streptavidin muteins of the invention (m400 from library 1; m4001 from library 2; m4, m23, m36, m41, m45 from library 3; m101, m111 from library5; m207, m212 from library 6; and m301, m302 from library 7) as well as streptavidin mutein "1" of U.S. Pat. No. 6,103,493 at a concentration in each case of 15 μg/ml in 10 mM $NaBO_3$, pH 8.5. Further proceeding was at room temperature (23° C.). The wells were blocked for 2 hours with each 200 μl 3% w/v BSA, 0.5% v/v Tween20 in TBS (100 mM Tris-CI pH8, 115 mM NaCl). After washing three times with TBS/Tween (TBS containing 0.05% v/v Tween20), 50 μl of the same buffer was added to each well. 50 μl 0.3 μM BAP-StrepII fusion protein in TBS/Tween (prepared by 67fold dilution with TBS/T of a 20 μM purified and dialysed BAP-StrepII stock solution in PBS) was added to the first well of each row and mixed. A dilution series was set up in the other wells of a row by pipetting 50 μl (from a total of 100 μl) out of the first well and mixing it with the contents (50 μl) of the next well in the same row etc. In this manner concentrations of the fusion protein between 150 nM in the first well of each row and 0.146484 nM in the eleventh well were obtained.

After incubating for one hour the solutions were removed and the wells were each washed twice with TBS/Tween and twice with TBS. Subsequently 100 μl of a solution of 0.5 mg/ml p-nitrophenyl phosphate in 1 mM $ZnSO_4$, 5 mM $MgCl_2$, 1 M Tris-CI pH8 was pipetted into each well. Data of each well were raised by measuring absorbance at 405 nm substracted by absorbance at 595 nm using a BioTek microplate reader el808. The activity of the bound BAP-StrepII fusion protein in each well was measured as difference value between the data obtained prior and after a 20 min incubation at 23° C. under shaking and is given in milli optical density units (mOD) for $\Delta(A_{405}-A_{595})$ in FIG. 1.

The data were evaluated assuming a single binding equilibrium between streptavidin mutein monomers (P) and the BAP-StrepII fusion protein (L) which yielded a dissociation constant $K_D$=[P]·[L]/[P·L]. Under the assumption that $[P]_{tot}$=[P]+[P·L] and that [L] is very much larger than [P·L] so that $[L]_{tot}$ is approximately the same as [L], the amount of bound fusion enzyme BAP-StrepII is determined as $[P·L]=[L]_{tot}[P]_{tot}/(K_D+[L]_{tot})$. This equation was used for fitting the measured data for [P·L](in terms of enzyme activity, $\Delta(A_{405}-A_{595})/\Delta t$) against $[L]_{tot}$ (the concentration of the applied BAP-StrepII fusion enzyme) by non-linear least squares regression, with $K_D$ and $[P]_{tot}$ (corresponding to the asymptotic activity value, $(\Delta(A_{405}-A_{595})/\Delta t)max$ as the parameters. FIG. 1 shows the graph of experimental results obtained from 2 selected streptavidin muteins of the invention in comparison to streptavidin mutein "1" of U.S. Pat. No. 6,103,493. ($\Delta(A_{405}-A_{595})$ for the control where no streptavidin (mutein) was immobilized and where the wells were blocked only was <1 for each of the BAP-StrepII concentrations during the 20 min incubation (not shown in the graph)). Table 8 gives the evaluated results for $K_D$ and $(\Delta(A_{405}-A_{595})/\Delta t)max$ for a larger selection of streptavidin muteins of the invention in comparison to streptavidin mutein "1" of U.S. Pat. No. 6,103,493. It can be seen from these data that the streptavidin muteins of the invention have a significantly higher affinity for Strep-tagII fused to BAP than streptavidin mutein "1" of U.S. Pat. No. 6,103,493 and, therefore, are more suitable for efficient immobilization of Strep-tag(II) fusion proteins to a solid phase, as shown in this ELISA.

Example 11: Affinity Chromatography

The streptavidin muteins (m400 from library 1; m4001 from library 2; m4, m23, m36, m41, m45 from library 3; m111 from library5; m207, m212 from library 6; and m301, m302 from library 7) were prepared as described in example 9 as well as streptavidin mutein "1" of U.S. Pat. No. 6,103,493 and wt-streptavidin. Then, the proteins were coupled to NHS-activated Sepharose 4 Fast Flow (GE Healthcare) according to the instructions of the manufacturer (cf. Schmidt and Skerra, 1994, supra). Sepharose gel loading with the respective streptavidin mutein was determined with a BCA assay (Pierce) according to the instructions of the manufacturer. Briefly, 50 µl of a 10% v/v Sepharose gel suspension in buffer (100 mM Tris-CI pH8) were mixed with the freshly prepared BCA reagent and incubated for 30 min at 37° C. At each measurement a reference curve was determined in parallel with standards of streptavidin mutein "1" at different concentrations dissolved in the same buffer. The determined Sepharose gel loading with the different streptavidin muteins with respect to the fitted (2nd order polynomial) reference curve is shown in Table 9 and 10 as result of the mean value of 3 independent measurements. As validity control for this BCA assay based determination method for solid phase bound streptavidin muteins, a reference Sepharose gel of known loading with streptavidin mutein "1" was measured in parallel. The resulting BCA derived value deviated by less than 1% from the reference measurement value thereby proving the BCA assay to provide reliable data for determination of Sepharose bound streptavidin muteins.

In order to examine the behaviour of the streptavidin muteins including streptavidin mutein "1" of U.S. Pat. No. 6,103,493 and wt-streptavidin immobilized in this manner in the affinity purification of Strep-tagII-carrying fusion proteins, the recombinant cytochromeb562 (Schmidt and Skerra 1994, supra) fused to the Strep-tagII (also denoted cytb562-StrepII) was expressed via the tet promoter/operator controlled plasmid pASK-IBA2-cytochromeb562 (SEQ ID NO. 2), essentially as described in Schmidt & Skerra (2007), supra. Briefly, E. coli JM83 was transformed with pASK-IBA2-cytochromeb562 and cultivated at 37° C. in LB medium containing 100 µg/ml ampicillin. Expression was induced at an $OD_{550}$=0.5 with 0.2 µg/ml anhydrotetracycline and continued for 3 h at 37° C. Cells were then harvested via centrifugation and resuspended in a hundredth volume (with respect to the culture volume) pre-chilled buffer W (100 mM Tris-CI pH8, 150 mM NaCl, 1 mM EDTA), e.g. in 10 ml when derived from a culture volume of 1 liter. Cells are lysed via sonication and cell debris were removed by centrifugation (30000 g, 15 min, 4° C.). The cleared supernatant was then subjected to Strep-Tactin affinity chromatography to purify the recombinant cytochromeb562-Strep-tagII fusion protein. After purification, desthiobiotin was removed by dialysis against buffer W and such prepared cytochromeb562-Strep-tagII fusion protein was then used for the following affinity chromatography experiments to characterize the streptavidin muteins of the invention in comparison to streptavidin mutein "1" of U.S. Pat. No. 6,103,493 and in comparison to wt streptavidin.

In a first affinity chromatography experiment, 450 µl Sepharose gel (derived from 4.5 ml of a 10% suspension) with each of the different streptavidin muteins of the invention as well as streptavidin mutein "1" of U.S. Pat. No. 6,103,493 and wt streptavidin was filled into a 2 ml column (Pierce, Cat. no. 89896) between 2 polyethylene filter discs. Then, 3 ml of 1 mg/ml purified cytochromeb562-Strep-tagII fusion protein in buffer W was applied at gravity flow to each column. In this way, each column was largely overloaded and cytochromeb562 Strep-tagII fusion protein emerges in the eluate. Then, each column was washed 2 times with 2.5 ml buffer W. Retained cytochrome was eluted with 10 mM biotin in buffer W and quantified spectrophotometrically by measuring absorbance of the eluate at 280 nm using the molar extinction coefficient $\epsilon_{280}$=8250 $M^{-1}$ $cm^{-1}$. Results are given in Table 9. All muteins of the invention retained significantly more cytochromeb562 Strep-tagII fusion protein in comparison to mutein "1" of U.S. Pat. No. 6,103,493 (up to 3 times more) and by far more in comparison to wt streptavidin (up to 28 times more). Results were normalized to the amount of immobilized streptavidin (mutein). Thus, with the muteins of the invention, affinity columns of significantly improved Strep-Tag®II fusion protein binding capacity can be prepared.

In a second affinity chromatography experiment, Sepharose gel with an aggregate of 1 mg streptavidin mutein of the invention, of 1 mg streptavidin mutein "1" of U.S. Pat. No. 6,103,493 and of 1 mg wt streptavidin (derived from the corresponding amount of a 10% suspension) was filled into a 2 ml column (Pierce, Cat. no. 89896) between 2 polyethylene filter discs. Then, 10 times 5 ml of 10 µg/ml purified cytochromeb562-Strep-Tag®II fusion protein (500 µg in total) in buffer W was applied at gravity flow to each column. The flow rate was in all cases between 0.6 and 0.8 ml per min. Each column was washed with 1 column volume (CV) buffer W. Captured cytochromeb562-Strep-tagII fusion protein was eluted by the addition of 10 mM biotin in buffer W and quantified spectrophotometrically by measuring absorbance of the eluate at 280 nm using the molar extinction coefficient $\epsilon_{280}$=8250 $M^{-1}$ $cm^{-1}$. Results are given in Table 10. All muteins of the invention captured significantly more cytochromeb562 Strep-tagII fusion protein in comparison to mutein "1" of U.S. Pat. No. 6,103,493 (up to more than 3 times more) per immobilized streptavidin (mutein). Thus, with the muteins of the invention, affinity columns can be prepared providing significantly improved yields of a Strep-Tag®II fusion protein applied in comparatively diluted form as it is, e.g., the case for recombinant proteins secreted by mammalian cells to the cell culture medium. Recoveries of up to nearly 70% of the applied Strep-Tag®II fusion protein were obtained with the muteins of the invention while using an affinity material amount providing only a theoretic 2fold excess of immobilized Strep-Tag®II binding sites over the applied Strep-Tag®II ligand at the fusion protein (cytochromeb562 in this case), thereby demonstrating the efficiency of affinity capture of Strep-Tag®II fusion proteins using streptavidin muteins of the invention immobilized to a resin.

It has further to be noted that, in contrast to streptavidin mutein "1" of U.S. Pat. No. 6,103,493, the use of desthiobiotin did not lead to efficient elution in the case of most of the streptavidin muteins of the invention. When biotin was used instead, sharp elution was also achieved in the case of the muteins.

Example 12: Affinity Increase Due to Mutations in the Region of Amino Acids 115-121 are Independent from the Context of Amino Acid Region 43-52

Mutein m4001-m9 (FIG. 4, comprising the amino acid sequence of SEQ ID NO: 58 $Glu^{117}Asn^{118}Ala^{119}Gly^{120}Tyr^{121}$ at positions 117 to 121 of the streptavidin amino acid sequence) was one of the top results of screening a library of streptavidin muteins based on streptavidin mutein m4001 carrying the amino acids Ala, Cys, Gly, Cys at positions 44, 45, 46, 52, respectively (FIG. 4), where amino acid positions 117, 120 and 121 were randomized. The selection criterion/quality determining parameter was signal intensity produced in the filter sandwich assay (Example 8). Based on these results, the identified amino acids Glu, Gly and Tyr at positions 117, 120 and 121 were transferred from the context of mutein m4001 into the context of mutein "1" to obtain streptavidin mutein m1-9 (see FIG. 4 for the complete amino acid sequence of mutein m1-9). Thus, a result (the improved binding affinity towards streptavidin binding peptides) obtained for the amino acid region 115-121 in the context of a certain amino acid sequence for the loop formed by amino acid residues 43-52, i.e. the sequence of m4001, was combined with another amino acid sequence for region 43-52, i.e. the sequence of mutein "1" in this case. Affinities were measured via Bia-Core™ for the interaction of this new combined streptavidin mutein m1-9 with 2 different Strep-tagII (mono-tag) or di-tag3 fusion proteins and compared to the affinities of the fusion proteins to the streptavidin mutein "1" (Table 11). The mutein m1-9 provides an affinity increase of a factor of around 10 for GFP-StrepII (Green Fluorescent Protein) and of around 30 for Cytb562-StrepII. This is in the same range as the affinity increases measured for a selection of streptavidin muteins of the present invention raised directly from the random libraries for their interaction with BAP-StreptagII (mono-tag) fusion protein (Table 8) and confirms the advantage that the muteins of the invention provide over the known mutein "1".

The mutein (combination product) m1-9 was also tested in similar affinity chromatography experiments as described for a selection of streptavidin muteins raised directly from the random libraries in Example 10. Also in this practical application related setting, the mutein m1-9 emerged to be significantly superior over mutein "1", in a similar degree as compared to the streptavidin muteins that were selected directly from the random libraries, These results obtained with the mutein m1-9 demonstrate that the affinity increases generated by replacing amino acids in the region of amino acid positions 115-121 for a certain amino acid sequence context in the region of amino acid positions 43-52 can be combined with another amino acid sequence context in the region of amino acid positions 43-52 while preserving the beneficial properties of these mutations. Thus, this confirms that the results obtained for the mutations in region 115-121 are context independent and may, if wanted, be combined with other beneficial amino acid sequences in other regions of streptavidin. Thus, the current invention does not only provide novel advantageous streptavidin muteins but provides the additional benefit that the mutations identified here can also improve the properties of known streptavidin muteins.

Example 13: Repeated Affinity Chromatography Cycles with Crude Lysates (E. coli)

The streptavidin mutein m1-9 was immobilized on agarose (Superflow) essentially as described in Example 11. The resulting resin had a biotin binding capacity of 233 nmol/ml (corresponding to a loading density of 3.1 mg mutein m1-9 per ml resin, assuming an activity of 100%). A column was filled with 0.5 ml of the resin and used for the repeated purification of GFP-StrepII from a crude E. coli extract under gravity flow to test its suitability for repeated purification cycles. The yield and purity of GFP-StrepII were determined after each purification cycle.

For this purpose, a cleared lysate of the total soluble content of E. coli cells after cytosolic expression of GFP-StrepII was prepared using Buffer W (100 mM Tris-Cl pH8, 150 mM NaCl, 1 mM EDTA) according to standard procedures described in the manuals of IBA GmbH (e.g. Manual (Twin) Strep-tag (version PR02-0025) available as PDF file at http://www.iba-lifesciences.com/technical-support.html). The lysate contained approximately 1.2 mg GFP-StrepII per ml. The column with 0.5 ml resin with mutein m1-9 was loaded in a first step with 0.25 ml cleared lysate. The column was washed 5 times with 1 column volume (CV) corresponding to 0.5 ml Buffer W and then eluted with 10 mM biotin in Buffer W. The column was regenerated (released from biotin) by washing it 2 times with 5 CV 10 mM NaOH. Then, a second amount of 0.25 ml cleared lysate was applied and again contained GFP-StrepII was isolated and the column was regenerated as described above. Then, in a third purification attempt on the same 0.5-ml column, the triple amount (0.75 ml) of cleared lysate was applied and the same process for purification of contained GFP-StrepII and column regeneration as described above was used. Then, in a fourth purification attempt on the same 0.5-ml column, again 0.75 ml cleared lysate were applied and the same process for purification of contained GFP-StrepII and column regeneration as described above was used. The results of this sequential purification experiment using the same column at each step are summarized in Table 12. As can be seen from Table 12, in each step the essentially same amount as applied of the Strep-Tag II fusion protein could be purified with a purity of more than 90%. Thus, this experiment demonstrates that affinity columns with streptavidin muteins of the invention can be reliably used for repeated purifications of a recombinant protein with constant high yields and high purity. Alternatively to using 10 CV 10 mM NaOH, the column can also be regenerated by washing with larger volumes of 10 mM HABA in Buffer W. This may be advisable if biotin has to be removed under milder conditions if, e.g., the resin or other support coated with a streptavidin mutein of the invention is sensitive against alkaline pH.

Example 14: Interaction of Mutein m1-9 with 2 Sequentially Arranged Streptavidin Binding Peptide Moieties (Di-Tag3)

The present invention provides streptavidin muteins with significantly increased affinities for Strep-tagII fusion proteins than known streptavidin muteins. However, limitations may remain when higher affinities are required in a given application. This may be the case in purification scenarios where at least one of the binding partners—Strep-Tag®II fusion protein or the respective streptavidin mutein—is present or applied at very low concentration. Such examples are poor expression of the Strep-Tag®II fusion protein and/or using large buffer volumes for cell lysis or secreting the Strep-Tag®II fusion protein to the cell culture medium. In all these cases a large sample volume containing the target protein at low concentration is applied to the affinity column. On the other hand, also the dilution of the streptavidin mutein reaction partner leads to suboptimal performance which is e. g., the case for batch purification in contrast to column purification. However, also other applications downstream purification may take advantage from a higher affinity. Illustrative examples are the directed, mild and stable immobilization of dedicated target proteins (or other molecules chemically fused with a Strep-tagII) to be analyzed on a solid phase coated with a streptavidin mutein for assay development. Examples for solid phases and corresponding assays are microplates for ELISA, Biosensors for e.g. ForteBio's Octet® or GE's BiaCore® family of instruments providing label-free, real-time measurements for the analysis of protein:protein, protein:peptide, and protein:small molecule interactions, chips for high throughput analysis of a multitude of analytes bound to its surface or beads, like magnetic beads or Alphascreen® beads or Luminex® beads for e.g. protein:protein interaction analysis. In all such examples, the coating of the respective solid phase with a streptavidin mutein should provide a generic platform for the simple, reproducible, mild and stable immobilization of an arbitrary protein to said solid phase. This will be extremely helpful as otherwise, a specific immobilization procedure has to be developed separately for each protein to be immobilized and analyzed.

Consequently, there may be still room for improved affinities to address these applications beyond affinity purification in a better way. Therefore, the binding characteristics of the streptavidin muteins of the invention was also tested for a tandem arrangement of two Strep-Tag®II binding sequences connected by a short linker (WSHPQFEKGGGSGGGSGGGSWSHPQFEK; SEQ ID NO: 103) that is named di-tag3 and that has been described in U.S. Pat. No. 7,981,632. U.S. Pat. No. 7,981,632 also describes for the Strep-Tag® affinity system the advantages of such a tandem arrangement—leading to simultaneous binding of both Strep-Tag®II sequences to a tetrameric streptavidin mutein thereby providing higher binding stability under maintenance of efficient competitive elution. While in the present example, the data were generated using di-tag3 fusion proteins, the benefits are, however, not limited to using this particular di-tag3 streptavidin binding mutein. Rather, the avidity effect will be also achieved with any other sequentially arranged streptavidin binding modules described in U.S. Pat. No. 7,981,632, thereby leading to other affinity characteristics being still enhanced.

Consequently, the affinity increase of the interaction between the streptavidin muteins of the present invention, exemplified by mutein m1-9, and two sequentially arranged Strep-tagII binding moieties, exemplified by di-tag3, in comparison to its binding affinity for the monovalent Strep-tagII was analyzed via real-time interaction analysis on a BiaCore™ T100 instrument and compared with the affinity increase of the same di-tag3 versus Strep-tagII in case of mutein "1" (Table 11). The di-tag3 and Strep-tagII were presented at the C-terminus of two different recombinant proteins, namely GFP and cytochrome b562. The result was very surprising. While the di-tag3 led to an affinity increase in case of mutein "1" of a factor of merely 10 in case of GFP and merely 200-400 in case of cytochrome b562, the respective increase in case of the mutein m1-9 of the present invention was 300-600 and 10,000-40,000. Thus, the mutein m1-9 of the present invention provides an avidity effect comparable to IgG antibodies (Roitt et al., third ed., Mosby, St Louis, pages 6.3-6.4 1993) which is much more pronounced (increased by a factor of 50-100) than the avidity effect provided by the state of the art mutein "1".

The off-rate ($\approx 0,000015$ s$^{-1}$) for avidic binding of di-tag3 to mutein m1-9 specifies an interaction with a half live of $T_{1/2}=\ln 2/k_{off}=46,209$ sec=770 min=>12 h. In case of a monovalent interaction such a slow off-rate cannot be efficiently disrupted by competitive elution as it would need 2 days to release approximately 95% of the bound molecules under the assumption that no rebinding can occur. Thus, such a monovalent interaction would not be suitable for affinity chromatography using competitive elution which is preferable because it can be accomplished under mild physiological conditions and as it provides high purities as non-specific binding contaminants are minimally released from the resin during elution. However, the off-rate of an avidic binding interaction resembles under competitive conditions the off-rate of the single interacting moiety with the slowest off-rate. Therefore, a di-tag3 fusion protein can still be eluted rather efficiently from affinity resins carrying (immobilized thereon) streptavidin muteins of the present invention. This ability to elute these fusion proteins is consistent with the observations made in U.S. Pat. No. 7,981,632 for the streptavidin binding peptide di-tag3 interacting with mutein "1". The elution behavior from a column having immobilised thereon the mutein m1-9 was in fact similar for GFP-StrepII and GFP-di-tag3 illustrating that the theoretical considerations made above are of practical relevance (data not shown). The off-rate of GFP-StrepII specifies a T2=161 sec so that roughly 11 min are needed to displace 95% of the bound molecules. This is no obstacle for efficient elution during affinity chromatography. To obtain the target protein as concentrated as possible, the column may be in a first step submersed with 1 column volume (CV) of elution buffer containing a competitor. Then, the flow can be stopped for 10-20 min to allow for displacement of the bound target protein prior to eluting it by re-starting flow with elution buffer again. Alternatively, the elution may be performed at very slow flow rates to provide the target protein at higher concentrations.

On the other hand, the very stable interaction between di-tag3 and the mutein m1-9 under non-competitive conditions ($T_{1/2}=>12$ h) makes this interaction very attractive to be generically used for the directed, mild and stable immobilization of any given target protein that is fused (chemically or recombinantly) to di-tag3 (or any other sequentially arranged streptavidin mutein binding moieties as, e.g., described in U.S. Pat. No. 7,981,632) on a solid phase during the development of assays in analytical settings as described above (ELISA, Alphascreen®, Luminex®, BiaCore®, Octet®, to name a few). Moreover, reversibility of the interaction in the presence of a competitor enables mild regeneration of the device or sample coated with a streptavidin mutein of the present invention to remove the bound di-tag3 fusion protein after analysis of a certain analyte and to couple another di-tag3 fusion protein for analysis of another analyte binding to the di-tag3 fusion protein. Mild regeneration conserves the device or sample and the coupled proteinaceous receptor being a streptavidin mutein of the present invention in this example.

Another illustrative example where this property can be exploited is affinity determination via a surface plasmon resonance technology such as BiaCore™. A suitable chip (e.g. CM5 in the case of BiaCore™) is coated with a streptavidin mutein of the present invention. A di-tag3 fusion protein for which the affinity for a ligand is aimed to be determined is stably bound to the chip via its fused di-tag3 stably binding to the immobilized streptavidin mutein of the present invention. Then, after determining the binding kinetics of the ligand applied at a certain concentration, the chip has to be regenerated from the ligand which has to be applied at another concentration. If this is not possible without damaging the di-tag3 fusion protein, the same chip can be regenerated from the whole complex, i.e. di-tag3 fusion protein with bound ligand, by adding a competitor, e.g. biotin, and washing off the competitor, e.g. by using another competitor of reduced affinity (e.g. HABA (=2-(4-hydroxyphenylazo)benzoic acid)), in further steps and finally washing the chip with buffer alone. Finally, the chip is regenerated for binding a new amount of the di-tag3 fusion protein for analysis of ligand binding applied at another concentration without the need of using a new chip.

The high affinity of di-tag3 fusion proteins for a mutein such as mutein m1-9 should lead to a very efficient exploitation of the binding sites of immobilized streptavidin mutein m1-9 during affinity chromatography. To test this assumption, a 0.6 ml column was packed with immobilized mutein m1-9 described above (233 nmol biotin binding capacity per ml). The column provides thus an amount of 140 nmol biotin binding sites. The column was overloaded with GFP-di-tag3 fusion protein by addition of 2.6 mg of the GFP fusion protein. The column was then washed with 5 CV buffer W and remaining GFP-di-tag3 fusion protein was eluted with 10 mM biotin in buffer W. Eluted GFP-di-tag3 was quantified to be 2.13 mg by measuring absorbance at 280 nm and using the theoretical extinction coefficient of E0.1%=1.053. This amount of 2.13 mg corresponds to 71 nmol GFP-di-tag3 fusion protein. Thus, the stochiometry is 2:1. It can be deduced from this stochiometry that each binding peptide di-tag3 occupies 2 binding sites on the mutein m1-9 and that each binding site is in complex with a Strep-tagII moiety, thereby corresponding to a capacity exploitation of near to 100%. From this result and from the strong avidity effect shown by the BiaCore™ data, irrespective whether the chip was loaded at low or at high density with mutein m1-9 (see Table 11), it can be deduced that one di-tag3 binding peptide occupies very efficiently the 2 binding sites that are located close to each other on one tetramer (in fact, each tetramer has 4 binding sites which are located pair wise in close proximity; Weber et al., 1989, Science 243, 85-88) so that there is no or only little competition by different di-tag3 sequences for such binding sites located in close proximity at the concentrations used in this experiment. This further means that it should be possible to dimerize in a well defined manner di-tag3 (or other sequentially arranged streptavidin binding epitopes as, e.g., disclosed in U.S. Pat. No. 7,981,632) fusion proteins or proteins conjugated to di-tag3 on a streptavidin mutein tetramer of the invention. Due to the very slow off-rate ($T_{1/2}$=>12 h) there is no considerable exchange of the complex forming partners within the time frame of standard analytical assays which are accomplished usually in the 1 h range. Thus, when using 2 differently labeled streptavidin mutein m1-9 preparations (the label may be a fluorescent label, a chromophoric label, an enzymatic label, a magnetic label (magnetic bead), or other beads as used in the alphascreen or luminex assay platforms, or simply an agarose bead of a certain size or any other addressable property) each labeled variant is complexed by a different di-tag3 fusion protein. In this case both complex preparations may be mixed without that significant interchange between labeled streptavidin muteins and di-tag3 fusion proteins occurs at standard assay durations being <1 h. To provide a clarifying example: Preparation 1 is composed of mutein m1-9-label1 complexed with di-tag3-fusion-protein X and preparation 2 is composed of mutein m1-9-label2 complexed with di-tag3-fusion-protein Y. Then both preparations may be mixed without formation of significant populations of mutein m1-9-label1 complexed with di-tag3-fusion-protein Y and mutein m1-9-label2 complexed with di-tag3-fusion-protein X. This property enables multiplex assays where e.g. in a sample or in a specimen (e.g. in immunocytochemistry) or on a cell or on any other entity, different targets may be simultaneously addressed by a dedicated label bound via a streptavidin mutein of the invention to a ligand specific for a certain target fused or conjugated to di-tag3 without getting artifacts from interchanged detection complexes. But as the di-tag3:streptavidin mutein complex can still be efficiently reversed by the addition of a competitor like biotin, this methodology optionally additionally allows the efficient removal of the label from the target. This may be important for re-using the sample or specimen or cell or any other biological entity, which may be a precious unique specimen, in further assays. As ligands are multimerized by this strategy (dimerized on one labelled streptavidin mutein tetramer or multimerized on labeled streptavidin mutein multimers multimerized e.g. via chemical crosslinking), also low affinity ligands may be used in this methodology for multiplexed labeling assays. In this case, also the ligand can be easily removed from the sample or specimen or cell or any other entity after monomerization by competitive disruption of the complex between di-tag3 and streptavidin mutein of the invention and subsequent washing (cf. Streptamer® technology as e.g. described in Stemberger et al., 2012, PLoSONE, Volume 7 Issue 4 e35798). This is a further advantage of the streptavidin muteins of the present invention, illustrating the superior properties of these muteins over the known streptavidin muteins used for interacting with streptavidin binding peptides.

The invention is further elucidated by the electronically filed sequence protocol, in which inter alia:

SEQ ID NO 1: shows the nucleotide sequence of the expression vector pASK75-phoA which contains a sequence coding for the PhoA signal peptide (bold) followed by the sequence coding for *E. coli* alkaline phosphatase (BAP, underlined, continuous line) followed by the sequence coding for a linker (underlined, dotted line), followed by the sequence coding for the Strep-Tag®II (underlined, dashed line). The gene is operatively linked to the tetracyclin promoter/operator (tetP/O) for transcription regulation. The vector is suitable for periplasmic expression of a BAP-Strep-Tag®II fusion protein. General use of this tet-promoter based expression system is described in U.S. Pat. No. 5,849,576.

SEQ ID NO 2: shows the nucleotide sequence of the expression vector pASK-IBA2-cytochromeb562 which contains a sequence coding for the OmpA signal peptide (bold) followed by the sequence coding for *E. coli* cytochromeb562 (Cytb562, underlined, continuous line) followed by the sequence coding for a linker (underlined, dotted line), followed by the sequence coding for the Strep- Tag®II (underlined, dashed line). The gene for the cytochromeb562 Strep-tagII fusion protein (also denoted cytb562-StrepII) is operatively linked to the tetracyclin promoter/operator (tetP/O) for transcription regulation. The vector is suitable for periplasmic expression of a cytb562-Strep-tagII fusion protein. General use of this tet-promoter based expression system is described in U.S. Pat. No. 5,849,576.

SEQ ID NO 3: shows the nucleotide sequence of the expression vector pASK-IBA2-SAm1 which contains a sequence coding for the OmpA signal peptide (bold) followed by the sequence coding for streptavidin mutein "1" disclosed by U.S. Pat. No. 6,103,493 (Ala13-Ser139, underlined, continuous line). The gene is operatively linked to the tetracyclin promoter/operator (tetP/O) for transcription regulation. The vector is suitable for periplasmic expression of streptavidin mutein "1". General use of this tet-promoter based expression system is described in U.S. Pat. No. 5,849,576.

SEQ ID NO 4: shows the nucleotide sequence of the expression vector pASK-IBA2-SAm4001 which contains a sequence coding for the OmpA signal peptide (bold) followed by the sequence coding for streptavidin mutein m4001 of the present invention (Ala13-Ser139, underlined, continuous line). The gene is operatively linked to the tetracyclin promoter/operator (tetP/O) for transcription regulation. The vector is suitable for periplasmic expression of streptavidin mutein m4001. General use of this tet-promoter based expression system is described in U.S. Pat. No. 5,849,576.

SEQ ID NO 5: shows the nucleotide sequence of the oligonucleotide primer P1,

SEQ ID NO 6: shows the nucleotide sequence of the oligonucleotide primer P2,

SEQ ID NO 7: shows the nucleotide sequence of the oligonucleotide primer P3,

SEQ ID NO 8: shows the nucleotide sequence of the oligonucleotide primer P4,

SEQ ID NO 9: shows the nucleotide sequence of the oligonucleotide primer P5,

SEQ ID NO 10: shows the nucleotide sequence of the oligonucleotide primer P6,

SEQ ID NO 11: shows the nucleotide sequence of the oligonucleotide primer P7,

SEQ ID NO 12: shows the nucleotide sequence of the oligonucleotide primer P8,

SEQ ID NO 13: shows the nucleotide sequence of the oligonucleotide primer P9,

SEQ ID NO 14: shows the nucleotide sequence of the oligonucleotide primer P10.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of certain embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied herein may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

TABLE 1

| Library 1 (SEQ ID NO: 203) | $Xaa^{44}Xaa^{45}Ala^{46}Arg^{47}Gly^{48}Asn^{49}Ala^{50}Glu^{51}Xaa^{52}$ | relative signal |
|---|---|---|
| Wt (SEQ ID NO: 15) | $Glu^{44}Ser^{45}Ala^{46}Val^{47}Gly^{48}Asn^{49}Ala^{50}Glu^{51}Ser^{52}$ | − |
| mutein "1" (SEQ ID NO: 16) | $Val^{44}Thr^{45}Ala^{46}Arg^{47}Gly^{48}Asn^{49}Ala^{50}Glu^{51}Ser^{52}$ | + |
| m400 (SEQ ID NO: 18) | Gly$^{44}$Cys$^{45}$$Ala^{46}Arg^{47}Gly^{48}Asn^{49}Ala^{50}Glu^{51}$Cys$^{52}$ | ++ |
| m402 (SEQ ID NO: 19) | Ala$^{44}$Cys$^{45}$$Ala^{46}Arg^{47}Gly^{48}Asn^{49}Ala^{50}Glu^{51}$Cys$^{52}$ | ++ |

TABLE 2

| Library 2 (SEQ ID NO: 204) | (Ala/Gly)$^{44}$Cys$^{45}$Xaa$^{46}$Xaa$^{47}$Gly$^{48}$Asn$^{49}$Ala$^{50}$Glu$^{51}$Cys$^{52}$ | relative signal |
|---|---|---|
| Wt (SEQ ID NO: 205) | Glu$^{44}$Ser$^{45}$Ala$^{46}$Val$^{47}$Gly$^{48}$Asn$^{49}$Ala$^{50}$Glu$^{51}$Ser$^{52}$ | − |
| mutein "1" (SEQ ID NO: 16) | Val$^{44}$Thr$^{45}$Ala$^{46}$Arg$^{47}$Gly$^{48}$Asn$^{49}$Ala$^{50}$Glu$^{51}$Ser$^{52}$ | + |
| m4001 (SEQ ID NO: 20) | Ala$^{44}$Cys$^{45}$Gly$^{46}$Arg$^{47}$Gly$^{48}$Asn$^{49}$Ala$^{50}$Glu$^{51}$Cys$^{52}$ | +++ |

TABLE 3

| Library 3 (SEQ ID NO: 206) | Xaa$^{117}$Asn$^{118}$Ala$^{119}$Xaa$^{120}$Xaa$^{121}$ | relative signal |
|---|---|---|
| Wt (SEQ ID NO: 207) | Ala$^{117}$Asn$^{118}$Ala$^{119}$Trp$^{120}$Lys$^{121}$ | − |
| mutein "1" | Ala$^{117}$Asn$^{118}$Ala$^{119}$Trp$^{120}$Lys$^{121}$ | − |
| m36 (SEQ ID NO: 21) | Tyr$^{117}$Asn$^{118}$Ala$^{119}$Phe$^{120}$Met$^{121}$ | |
| m23 (SEQ ID NO: 22) | Tyr$^{117}$Asn$^{118}$Ala$^{119}$Tyr$^{120}$Ala$^{121}$ | +++++ |
| m41 (SEQ ID NO: 23) | Ala$^{117}$---$^{118}$---$^{119}$Trp$^{120}$Tyr$^{121}$ | +++++ |
| m4 (SEQ ID NO: 24) | Asp$^{117}$Asn$^{118}$Ala$^{119}$Gly$^{120}$Phe$^{121}$ | +++++ |
| m12 (SEQ ID NO: 25) | Arg$^{117}$Asn$^{118}$Ala$^{119}$Gly$^{120}$Phe$^{121}$ | +++++ |
| m22 (SEQ ID NO: 26) | Gln$^{117}$Asn$^{118}$Ala$^{119}$Gly$^{120}$Phe$^{121}$ | +++++ |
| m31 (SEQ ID NO: 27) | Phe$^{117}$Asn$^{118}$Ala$^{119}$Ser$^{120}$Trp$^{121}$ | +++++ |
| m32 (SEQ ID NO: 28) | Asp$^{117}$Asn$^{118}$Ala$^{119}$Val$^{120}$Met$^{121}$ | +++++ |
| m35 (SEQ ID NO: 29) | Ala$^{117}$---$^{118}$---$^{119}$Trp$^{120}$Met$^{121}$ | +++++ |
| m38 (SEQ ID NO: 30) | Glu$^{117}$Asn$^{118}$Ala$^{119}$Gly$^{120}$Phe$^{121}$ | +++++ |
| m40 (SEQ ID NO: 31) | Tyr$^{117}$Asn$^{118}$Ala$^{119}$Tyr$^{120}$Ser$^{121}$ | +++++ |
| m42 (SEQ ID NO: 32) | Phe$^{117}$Asn$^{118}$Ala$^{119}$Tyr$^{120}$Gly$^{121}$ | +++++ |
| m45 (SEQ ID NO: 33) | Tyr$^{117}$Asn$^{118}$Ala$^{119}$Gly$^{120}$Phe$^{121}$ | +++++ |
| m46 (SEQ ID NO: 34) | Arg$^{117}$Asn$^{118}$Ala$^{119}$Tyr$^{120}$Ala$^{121}$ | +++++ |
| m47 (SEQ ID NO: 35) | Trp$^{117}$Asn$^{118}$Ala$^{119}$Tyr$^{120}$Gly$^{121}$ | +++++ |
| m7 (SEQ ID NO: 36) | Leu$^{117}$Asn$^{118}$Ala$^{119}$Gly$^{120}$Phe$^{121}$ | ++++ |
| m10 (SEQ ID NO: 37) | His$^{117}$Asn$^{118}$Ala$^{119}$Gly$^{120}$Tyr$^{121}$ | ++++ |
| m17 (SEQ ID NO: 38) | Met$^{117}$Asn$^{118}$Ala$^{119}$Gly$^{120}$Phe$^{121}$ | ++++ |
| m21 (SEQ ID NO: 39) | Arg$^{117}$Asn$^{118}$Ala$^{119}$Gly$^{120}$Tyr$^{121}$ | ++++ |
| m24 (SEQ ID NO: 40) | Glu$^{117}$Asn$^{118}$Ala$^{119}$Gly$^{120}$Trp$^{121}$ | ++++ |
| m27 (SEQ ID NO: 41) | His$^{117}$Asn$^{118}$Ala$^{119}$Gly$^{120}$Phe$^{121}$ | ++++ |
| m28 (SEQ ID NO: 42) | Ser$^{117}$Asn$^{118}$Ala$^{119}$Gly$^{120}$Phe$^{121}$ | ++++ |
| m30 (SEQ ID NO: 43) | Thr$^{117}$Asn$^{118}$Ala$^{119}$Gly$^{120}$Phe$^{121}$ | ++++ |
| m33 (SEQ ID NO: 44) | Asn$^{117}$Asn$^{118}$Ala$^{119}$Gly$^{120}$Phe$^{121}$ | ++++ |
| m1 (SEQ ID NO: 45) | Glu$^{117}$Asn$^{118}$Ala$^{119}$Gly$^{120}$Met$^{121}$ | +++ |
| m3 (SEQ ID NO: 46) | Trp$^{117}$Asn$^{118}$Ala$^{119}$Cys$^{120}$Cys$^{121}$ | +++ |
| m8 (SEQ ID NO: 47) | Met$^{117}$Asn$^{118}$Ala$^{119}$Phe$^{120}$Val$^{121}$ | +++ |
| m15 (SEQ ID NO: 48) | Ala$^{117}$Asn$^{118}$Ala$^{129}$Asp$^{120}$Trp$^{121}$ | +++ |

TABLE 3-continued

| Library 3 (SEQ ID NO: 206) | Xaa$^{117}$Asn$^{118}$Ala$^{119}$Xaa$^{120}$Xaa$^{121}$ | relative signal |
|---|---|---|
| m6 (SEQ ID NO: 49) | Ser$^{117}$Asn$^{118}$Ala$^{119}$Met$^{120}$Met$^{121}$ | ++ |
| m9 (SEQ ID NO: 50) | Arg$^{117}$Asn$^{118}$Ala$^{119}$Val$^{120}$Val$^{121}$ | ++ |
| m20 (SEQ ID NO: 51) | Ser$^{117}$Asn$^{118}$Ala$^{119}$Ser$^{120}$Phe$^{121}$ | ++ |
| m34 (SEQ ID NO: 52) | Ala$^{117}$---$^{118}$---$^{119}$Trp$^{120}$Asp$^{121}$ | ++ |
| m14 (SEQ ID NO: 53) | Arg$^{117}$Asn$^{118}$Ala$^{119}$Arg$^{120}$Ala$^{121}$ | + |
| m18 (SEQ ID NO: 54) | Ser$^{117}$Asn$^{118}$Ala$^{119}$Ala$^{120}$Phe$^{121}$ | + |
| m19 (SEQ ID NO: 55) | Gly$^{117}$Asn$^{118}$Ala$^{119}$Met$^{120}$Met$^{121}$ | + |

TABLE 4

| Library 4 (SEQ ID NO: 208) | Xaa$^{117}$Asn$^{118}$Ala$^{119}$Xaa$^{120}$Xaa$^{121}$ | relative signal |
|---|---|---|
| Wt | Ala$^{117}$Asn$^{118}$Ala$^{119}$Trp$^{120}$Lys$^{121}$ | − |
| m4001 | Ala$^{117}$Asn$^{118}$Ala$^{119}$Trp$^{120}$Lys$^{121}$ | − |
| m8 (SEQ ID NO: 56) | Glu$^{117}$Asn$^{118}$Ala$^{119}$Gly$^{120}$Phe$^{121}$ | +++++ |
| m21 (SEQ ID NO: 57) | Asp$^{117}$Asn$^{118}$Ala$^{119}$Gly$^{120}$Tyr$^{121}$ | +++++ |
| m9 (SEQ ID NO: 58) | Glu$^{117}$Asn$^{118}$Ala$^{119}$Gly$^{120}$Tyr$^{121}$ | +++++ |
| m1 (SEQ ID NO: 59) | Arg$^{117}$Asn$^{118}$Ala$^{119}$Met$^{120}$Met$^{121}$ | ++++ |
| m2 (SEQ ID NO: 60) | Arg$^{117}$Asn$^{118}$Ala$^{119}$Gly$^{120}$Phe$^{121}$ | ++++ |
| m3 (SEQ ID NO: 61) | Ala$^{117}$Asn$^{118}$Ala$^{119}$Pro$^{120}$Ala$^{121}$ | ++++ |
| m5 (SEQ ID NO: 62) | Ala$^{117}$Asn$^{118}$Ala$^{119}$Met$^{120}$Val$^{121}$ | ++++ |
| m13 (SEQ ID NO: 63) | Gln$^{117}$Asn$^{118}$Ala$^{119}$Ser$^{120}$Ala$^{121}$ | ++++ |
| m14 (SEQ ID NO: 64) | Ala$^{117}$Asn$^{118}$Ala$^{119}$Gly$^{120}$Phe$^{121}$ | ++++ |
| m24 (SEQ ID NO: 65) | Gln$^{117}$Asn$^{118}$Ala$^{119}$Met$^{120}$Val$^{121}$ | ++++ |
| m4 (SEQ ID NO: 66) | Asn$^{117}$Asn$^{118}$Ala$^{119}$Gly$^{120}$Tyr$^{121}$ | +++ |
| m6 (SEQ ID NO: 67) | Ala$^{117}$Asn$^{118}$Ala$^{119}$Ala$^{120}$Val$^{121}$ | +++ |
| m7 (SEQ ID NO: 68) | Ser$^{117}$Asn$^{118}$Ala$^{119}$Met$^{120}$Ile$^{121}$ | +++ |
| m10 (SEQ ID NO: 69) | His$^{117}$Asn$^{118}$Ala$^{119}$Gly$^{120}$Tyr$^{121}$ | +++ |
| m15 (SEQ ID NO: 70) | Ser$^{117}$Asn$^{118}$Ala$^{119}$Met$^{120}$Ala$^{121}$ | +++ |
| m23 (SEQ ID NO: 71) | Gln$^{117}$Asn$^{118}$Ala$^{119}$Val$^{120}$Ala$^{121}$ | +++ |
| m17 (SEQ ID NO: 72) | Tyr$^{117}$Asn$^{118}$Ala$^{119}$Tyr$^{120}$Met$^{121}$ | ++ |
| m12 (SEQ ID NO: 73) | Leu$^{117}$Asn$^{118}$Ala$^{119}$Trp$^{120}$Gly$^{121}$ | + |
| m20 (SEQ ID NO: 74) | His$^{117}$Asn$^{118}$Ala$^{119}$Ser$^{120}$Met$^{121}$ | + |

TABLE 5

| Library 5 (SEQ ID NO: 209) | (Phe/Tyr)$^{117}$Asn$^{118}$Ala$^{119}$Xaa$^{120}$Xaa$^{121}$ | relative signal |
|---|---|---|
| Wt | Ala$^{117}$Asn$^{118}$Ala$^{119}$Trp$^{120}$Lys$^{121}$ | − |
| mutein "1" | Ala$^{117}$Asn$^{118}$Ala$^{119}$Trp$^{120}$Lys$^{121}$ | − |
| m101 (SEQ ID NO: 75) | Tyr$^{117}$Asn$^{118}$Ala$^{119}$Phe$^{120}$Leu$^{121}$ | +++++ |

TABLE 5-continued

| Library 5 (SEQ ID NO: 209) | (Phe/Tyr)$^{117}$Asn$^{118}$Ala$^{119}$Xaa$^{120}$Xaa$^{121}$ | relative signal |
|---|---|---|
| m106 (SEQ ID NO: 76) | Phe$^{117}$Asn$^{118}$Ala$^{119}$Phe$^{120}$Leu$^{121}$ | +++++ |
| m111 (SEQ ID NO: 77) | Tyr$^{117}$Asn$^{118}$Ala$^{119}$Leu$^{120}$Trp$^{121}$ | +++++ |
| m100 (SEQ ID NO: 78) | Phe$^{117}$Asn$^{118}$Ala$^{119}$Tyr$^{120}$Ile$^{121}$ | +++++ |
| m110 (SEQ ID NO: 79) | Tyr$^{117}$Asn$^{118}$Ala$^{119}$Tyr$^{120}$Leu$^{121}$ | +++++ |
| m104 (SEQ ID NO: 80) | Tyr$^{117}$Asn$^{118}$Ala$^{119}$Tyr$^{120}$Gln$^{121}$ | ++++ |
| m108 (SEQ ID NO: 81) | Phe$^{117}$Asn$^{118}$Ala$^{119}$Ile$^{120}$Trp$^{121}$ | ++++ |

TABLE 6

| Library 6 (SEQ ID NO: 210) | Xaa$^{117}$---$^{118}$---$^{119}$Xaa$^{120}$Xaa$^{121}$ | relative signal |
|---|---|---|
| Wt | Ala$^{117}$Asn$^{118}$Ala$^{119}$Trp$^{120}$Lys$^{121}$ | − |
| mutein "1" | Ala$^{117}$Asn$^{118}$Ala$^{119}$Trp$^{120}$Lys$^{121}$ | − |
| m207 (SEQ ID NO: 82) | Thr$^{117}$---$^{118}$---$^{119}$Trp$^{120}$Leu$^{121}$ | +++++ |
| m212 (SEQ ID NO: 83) | His$^{117}$---$^{118}$---$^{119}$Trp$^{120}$Leu$^{121}$ | +++++ |
| m202 (SEQ ID NO: 84) | Ile$^{117}$---$^{118}$---$^{119}$Trp$^{120}$Arg$^{121}$ | +++++ |
| m204 (SEQ ID NO: 85) | His$^{117}$---$^{118}$---$^{119}$Trp$^{120}$Thr$^{121}$ | +++++ |
| m206 (SEQ ID NO: 86) | Thr$^{117}$---$^{118}$---$^{119}$Trp$^{120}$Arg$^{121}$ | +++++ |
| m208 (SEQ ID NO: 87) | Ala$^{117}$---$^{118}$---$^{119}$Trp$^{120}$Arg$^{121}$ | +++++ |
| m203 (SEQ ID NO: 88) | Arg$^{117}$---$^{118}$---$^{119}$Trp$^{120}$Ser$^{121}$ | ++++ |
| m209 (SEQ ID NO: 89) | Asn$^{117}$---$^{118}$---$^{119}$Trp$^{120}$Arg$^{121}$ | ++++ |
| m200 (SEQ ID NO: 90) | Lys$^{117}$---$^{118}$---$^{119}$Trp$^{120}$Ser$^{121}$ | +++ |
| m201 (SEQ ID NO: 91) | Ser$^{117}$---$^{118}$---$^{119}$Val$^{120}$Phe$^{121}$ | +++ |
| m211 (SEQ ID NO: 92) | Lys$^{117}$---$^{118}$---$^{119}$Trp$^{120}$Thr$^{121}$ | +++ |

TABLE 7

| Library 7 (SEQ ID NO: 209) | Xaa$^{117}$---$^{118}$---$^{119}$Trp$^{120}$Xaa$^{121}$ | relative signal |
|---|---|---|
| Wt | Ala$^{117}$Asn$^{118}$Ala$^{119}$Trp$^{120}$Lys$^{121}$ | − |
| mutein "1" | Ala$^{117}$Asn$^{118}$Ala$^{119}$Trp$^{120}$Lys$^{121}$ | − |
| m300 (SEQ ID NO: 93) | Ala$^{117}$---$^{118}$---$^{119}$Trp$^{120}$Tyr$^{121}$ | ++++++ |
| m301 (SEQ ID NO: 94) | His$^{117}$---$^{118}$---$^{119}$Trp$^{120}$Met$^{121}$ | ++++++ |
| m302 (SEQ ID NO: 95) | His$^{117}$---$^{118}$---$^{119}$Trp$^{120}$Tyr$^{121}$ | ++++++ |
| m303 (SEQ ID NO: 96) | Glu$^{117}$---$^{118}$---$^{119}$Trp$^{120}$Tyr$^{121}$ | ++++++ |
| m304 (SEQ ID NO: 97) | Gln$^{117}$---$^{118}$---$^{119}$Trp$^{120}$Tyr$^{121}$ | ++++++ |

TABLE 8

| Mutein | $K_D$ [nM] | $K_D$(mutein"1")/ $K_D$mutein | $(\Delta(A_{405}-A_{595})/\Delta t)_{max}$ |
|---|---|---|---|
| mutein „1" (SEQ ID NO: 16) | 110 | 1.0 | 703 |
| m4 (SEQ ID NO: 24) | 9 | 12.2 | 716 |
| m23 (SEQ ID NO: 22) | 12 | 9.2 | 968 |
| m36 (SEQ ID NO: 21) | 12 | 9.2 | 945 |
| m41 (SEQ ID NO: 23) | 13 | 8.5 | 613 |

TABLE 8-continued

| Mutein | $K_D$ [nM] | $K_D$(mutein"1")/ $K_D$mutein | $(\Delta(A_{405}-A_{595})/\Delta t)_{max}$ |
|---|---|---|---|
| m45 (SEQ ID NO: 33) | 18 | 6.1 | 566 |
| m101 (SEQ ID NO: 75) | 14 | 7.9 | 589 |
| m111 (SEQ ID NO: 77) | 13 | 8.5 | 492 |
| m207 (SEQ ID NO: 82) | 27 | 4.1 | 493 |
| m212 (SEQ ID NO: 83) | 17 | 6.5 | 607 |
| m301 (SEQ ID NO: 94) | 10 | 11.0 | 725 |
| m302 (SEQ ID NO: 95) | 5 | 22.0 | 726 |
| m402 (SEQ ID NO: 19) | 92 | 1.2 | 880 |
| m4001 (SEQ ID NO: 20) | 20 | 5.5 | 986 |
| m1-9 (SEQ ID NO: 194) | 25 | | 1696 |
| m4001 (SEQ ID NO: 20) | 27 | | 1049 |
| m4 (SEQ ID NO: 24) | 12 | | 518 |
| m23 (SEQ ID NO: 22) | 13 | | 644 |

TABLE 9

| Variant | Sepharose gel loading (100% gel suspension) [µg/ml] | immobilization degree relative to mutein "1" [%] | Retained Cytb$_{562}$-StrepII [µg] | Retained Cytb$_{562}$-StrepII per immobilized mutein [µg/µg] | Retained Cytb$_{562}$-StrepII per immobilized mutein relative to mutein "1" [%] |
|---|---|---|---|---|---|
| mutein „1" | 2747 | 100 | 156 | 0.13 | 100 |
| streptavidin wt | 2034 | 74 | 12 | 0.01 | 11 |
| m4 | 3557 | 129 | 564 | 0.35 | 280 |
| m23 | 3452 | 126 | 479 | 0.31 | 245 |
| m36 | 2985 | 109 | 429 | 0.32 | 254 |
| m41 | 3284 | 120 | 289 | 0.20 | 155 |
| m45 | 2711 | 99 | 472 | 0.39 | 308 |
| m111 | 2277 | 83 | 318 | 0.31 | 246 |
| m207 | 2767 | 101 | 358 | 0.29 | 229 |
| m212 | 3489 | 127 | 390 | 0.25 | 197 |
| m301 | 3149 | 115 | 400 | 0.28 | 225 |
| m302 | 2804 | 102 | 350 | 0.28 | 221 |
| m402 | 1776 | 51 | 111 | 0.14 | 111 |
| m4001 | 2429 | 65 | 175 | 0.16 | 127 |

Streptavidin Muteins Correspond to Those Listed in Table 8

TABLE 10

| Variant | Sepharose gel loading (100% gel suspension) [µg/ml] | column size for 1 mg immobilized mutein [µl] | captured Cytb$_{562}$-StrepII [µg] | captured Cytb$_{562}$-StrepII per immobilized mutein relative to mutein "1" [%] | yield of Cytb$_{562}$-StrepII applied [%] |
|---|---|---|---|---|---|
| mutein „1" | 2747 | 364 | 98 | 100 | 20 |
| streptavidin wt | 2034 | 492 | 4 | 4 | 1 |
| m4 | 3557 | 281 | 321 | 327 | 64 |
| m23 | 3452 | 290 | 301 | 308 | 60 |
| m36 | 2985 | 335 | 307 | 314 | 61 |
| m41 | 3284 | 305 | 235 | 240 | 47 |
| m45 | 2711 | 369 | 335 | 342 | 67 |
| m111 | 2277 | 439 | 337 | 344 | 67 |
| m207 | 2767 | 361 | 274 | 279 | 55 |
| m212 | 3489 | 287 | 233 | 238 | 47 |
| m301 | 3149 | 318 | 285 | 291 | 57 |
| m302 | 2804 | 357 | 313 | 320 | 63 |
| m402 | 1776 | 563 | 153 | 156 | 31 |
| m4001 | 2429 | 412 | 168 | 171 | 34 |

Streptavidin Muteins Correspond to Those Listed in Table 8

TABLE 11

| Fusion protein | Streptavidin mutein | Relative streptavidin mutein density on chip [RU] | $K_{on} \times 10^5$ [M$^{-1}$s$^{-1}$] | $k_{off} \times 10^{-4}$ [s$^{-1}$] | $K_D$ [pM] |
|---|---|---|---|---|---|
| GFP-StrepII | mutein "1" | 325 | 1.00 | 300.00 | 300000 |
| | | 5567 | 1.90 | 250.00 | 130000 |

TABLE 11-continued

| Fusion protein | Streptavidin mutein | Relative streptavidin mutein density on chip [RU] | $K_{on} \times 10^5$ [$M^{-1}s^{-1}$] | $k_{off} \times 10^{-4}$ [$s^{-1}$] | $K_D$ [pM] |
|---|---|---|---|---|---|
| | m1-9 | 170 | 1.50 | 47.00 | 32000 |
| | | 4350 | 1.70 | 38.00 | 23000 |
| GFP-di-tag3 | mutein "1" | 325 | 0.80 | 43.00 | 57000 |
| | | 5567 | 1.50 | 17.00 | 11000 |
| | m1-9 | 170 | 2.80 | 0.15 | 53 |
| | | 4350 | 2.20 | 0.17 | 79 |
| Cytb$_{562}$-StrepII | mutein "1" | 325 | 0.17 | 2900.00 | 16700000 |
| | | 5567 | 0.14 | 2400.00 | 16700000 |
| | m1-9 | 170 | 0.70 | 410.00 | 586000 |
| | | 4350 | 0.52 | 250.00 | 485000 |
| Cytb$_{562}$-di-tag3 | mutein "1" | 325 | 0.60 | 58.00 | 97000 |
| | | 5567 | 1.20 | 53.00 | 44000 |
| | m1-9 | 170 | 10.00 | 0.15 | 14 |
| | | 4350 | 4.40 | 0.19 | 43 |

TABLE 12

| | 0.5 ml column with 3.1 mg/ml streptavidin mutein m1-9 | | | |
|---|---|---|---|---|
| | Purification 1 | Purification 2 | Purification 3 | Purification 4 |
| Applied volume of cleared lysate [ml] | 0.25 | 0.25 | 0.75 | 0.75 |
| Yield of GFP-StrepII [mg] | 0.57 | 0.54 | 1.80 | 1.82 |
| Purity [%] | 91.6 | 93.5 | 98.7 | 94.5 |

TABLE 13

| SEQ ID NO | Name | Sequence |
|---|---|---|
| SEQ ID NO. 1 | E. coli alkaline phosphatase Strep-tag II fusion protein (BAP-StrepII) - expressed by pASK75-phoA | |
| SEQ ID NO. 2 | plasmid pASK-IBA2-cytochromeb562 | |
| SEQ ID NO 3 | nucleotide sequence of the expression vector pASK-IBA2-SAm1 which contains a sequence coding for the OmpA signal peptide followed by the sequence coding for streptavidin mutein "1" disclosed by U.S. Pat. No. 6,103,493 | |
| SEQ ID NO 4 | nucleotide sequence of the expression vector pASK-IBA2-SAm4001 which contains a sequence coding for the OmpA signal peptide followed by the sequence coding for streptavidin mutein m4001 of the present invention | |
| SEQ ID NO. 5 | Primer 1 (P1) | 5'-TCG TGA CCG CGG GTG CAG ACG GAG CTC TGA CCG GTA CCT ACN N(C/G)N N(G/T)G CGC GTG GCA ACG CCG AGN N(C/G)C GCT ACG TCC TGA CCG GTC GTT Is: TCG TGA CCG CGG GTG CAG ACG GAG CTC TGA CCG GTA CCT ACN NSN NKG CGC GTG GCA ACG CCG AGN NSC GCT ACG TCC TGA CCG GTC GTT |
| SEQ ID NO. 6 | Primer 2 (P2) | 5'-AGT AGC GGT AAA CGG CAG A |
| SEQ ID NO. 7 | Primer 3 (P3) | 5'-CTG ACC GGT ACC TAC G(G/C)T TGC NN(G/C) NN(G/T) GGC AAC GCC GAG TGC CGC TAC GTC CTG A Is: CTG ACC GGT ACC TAC GST TGC NNS NNK GGC AAC GCC GAG TGC CGC TAC GTC CTG A |
| SEQ ID NO. 8 | Primer 4 (P4) | 5'-GCC NN(G/C) NN(G/T) TCC ACG CTG GTC GGC CA Is: GCC NNS NNK TCC ACG CTG GTC GGC CA |
| SEQ ID NO. 9 | Primer 5 (P5) | 5'-GTT (A/C)NN CTC GGT GGT GCC GGA GGT Is: GTT MNN CTC GGT GGT GCC GGA GGT |

TABLE 13-continued

| SEQ ID NO | Name | Sequence |
|---|---|---|
| SEQ ID NO. 10 | Primer 6 (P6) | 5'-GTT A(A/T)A CTC GGT GGT GCC GGA GGT<br>Is:<br>GTT AMA CTC GGT GGT GCC GGA GGT |
| SEQ ID NO. 11 | Primer 7 (P7) | 5'-N(G/C)N N(G/T)T CCA CGC TGG TCG GCC AC<br>Is:<br>NSN NKT CCA CGC TGG TCG GCC AC |
| EQ ID NO. 12 | Primer 8 (P8) | 5'-N(A/C)N NCT CGG TGG TGC CGG AGG T<br>Is:<br>NMN NCT CGG TGG TGC CGG AGG T |
| SEQ ID NO. 13 | Primer 9 (P9) | 5'-GGN N(G/T)T CCA CGC TGG TCG GCC AC<br>Is:<br>GGN NKT CCA CGC TGG TCG GCC AC |
| SEQ ID NO. 14 | Primer 10 (P10) | 5'-A(C/A)N NCT CGG TGG TGC CGG AGG T<br>Is:<br>AMN NCT CGG TGG TGC CGG AGG T |
| SEQ ID NO: 15 | wild type streptavidin | Glu$^{44}$Ser$^{45}$Ala$^{46}$Val$^{47}$Gly$^{48}$Asn$^{49}$Ala$^{50}$Glu$^{51}$Ser$^{52}$<br>is:<br>ESAVGNAES |
| SEQ ID NO: 16 | mutein 1 | Val$^{44}$Thr$^{45}$Ala$^{46}$Arg$^{47}$Gly$^{48}$Asn$^{49}$Ala$^{50}$Glu$^{51}$Ser$^{52}$<br>is: VTARGNAES |
| SEQ ID NO: 17 | mutein 2 (44-47) | IGAR |
| SEQ ID NO: 18 | m400 | Gly$^{44}$Cys$^{45}$Ala$^{46}$Arg$^{47}$Gly$^{48}$Asn$^{49}$Ala$^{50}$Glu$^{51}$Cys$^{52}$<br>is: GCARGNAEC |
| SEQ ID NO: 19 | m402 | Ala$^{44}$Cys$^{45}$Ala$^{46}$Arg$^{47}$Gly$^{48}$Asn$^{49}$Ala$^{50}$Glu$^{51}$Cys$^{52}$<br>is: ACARGNAEC |
| SEQ ID NO: 20 | m4001 | Ala$^{44}$Cys$^{45}$Gly$^{46}$Arg$^{47}$Gly$^{48}$Asn$^{49}$Ala$^{50}$Glu$^{51}$Cys$^{52}$<br>is: ACGRGNAEC |
| SEQ ID NO: 21 | m36 | Tyr$^{117}$Asn$^{118}$Ala$^{119}$Phe$^{120}$Met$^{121}$<br>is: YNAFM |
| SEQ ID NO: 22 | m23 | Tyr$^{117}$Asn$^{118}$Ala$^{119}$Tyr$^{120}$Ala$^{121}$<br>is: YNAYA |
| SEQ ID NO: 23 | m41 | Ala$^{117}$---$^{118}$---$^{119}$Trp$^{120}$Tyr$^{121}$<br>is: AXXWY |
| SEQ ID NO: 24 | m4 | Asp$^{117}$Asn$^{118}$Ala$^{119}$Gly$^{120}$Phe$^{121}$<br>is: DNAGF |
| SEQ ID NO: 25 | m12 | Arg$^{117}$Asn$^{118}$Ala$^{119}$Gly$^{120}$Phe$^{121}$<br>is: RNAGF |
| SEQ ID NO: 26 | m22 | Gln$^{117}$Asn$^{118}$Ala$^{119}$Gly$^{120}$Phe$^{121}$<br>is: QNAGF |
| SEQ ID NO: 27 | m31 | Phe$^{117}$Asn$^{118}$Ala$^{119}$Ser$^{120}$Trp$^{121}$<br>is: FNASW |
| SEQ ID NO: 28 | m32 | Asp$^{117}$Asn$^{118}$Ala$^{119}$Val$^{120}$Met$^{121}$<br>is: DNAVM |
| SEQ ID NO: 29 | m35 | Ala$^{117}$---$^{118}$---$^{119}$Trp$^{120}$Met$^{121}$<br>is: AXXWM |
| SEQ ID NO: 30 | m38 | Glu$^{117}$Asn$^{118}$Ala$^{119}$Gly$^{120}$Phe$^{121}$<br>is: ENAGF |
| SEQ ID NO: 31 | m40 | Tyr$^{117}$Asn$^{118}$Ala$^{119}$Tyr$^{120}$Ser$^{121}$<br>is: YNAYS |
| SEQ ID NO: 32 | m42 | Phe$^{117}$Asn$^{118}$Ala$^{119}$Tyr$^{120}$Gly$^{121}$<br>is: FNAYG |
| SEQ ID NO: 33 | m45 | Tyr$^{117}$Asn$^{118}$Ala$^{119}$Gly$^{120}$Phe$^{121}$<br>is: YNAGF |

TABLE 13-continued

| SEQ ID NO | Name | Sequence |
|---|---|---|
| SEQ ID NO: 34 | m46 | Arg$^{117}$Asn$^{118}$Ala$^{119}$Tyr$^{120}$Ala$^{121}$<br>is: RNAYA |
| SEQ ID NO: 35 | m47 | Trp$^{117}$Asn$^{118}$Ala$^{119}$Tyr$^{120}$Gly$^{121}$<br>is: WNAYG |
| SEQ ID NO: 36 | m7 | Leu$^{117}$Asn$^{118}$Ala$^{119}$Gly$^{120}$Phe$^{121}$<br>is: LNAGF |
| SEQ ID NO: 37 | m10 | His$^{117}$Asn$^{118}$Ala$^{119}$Gly$^{120}$Tyr$^{121}$<br>is: HNAGY |
| SEQ ID NO: 38 | m17 | Met$^{117}$Asn$^{118}$Ala$^{119}$Gly$^{120}$Phe$^{121}$<br>is: MNAGF |
| SEQ ID NO: 39 | m21 | Arg$^{117}$Asn$^{118}$Ala$^{119}$Gly$^{120}$Tyr$^{121}$<br>is: RNAGY |
| SEQ ID NO: 40 | m24 | Glu$^{117}$Asn$^{118}$Ala$^{119}$Gly$^{120}$Trp$^{121}$<br>is: ENAGW |
| SEQ ID NO: 41 | m27 | His$^{117}$Asn$^{118}$Ala$^{119}$Gly$^{120}$Phe$^{121}$<br>is: HNAGF |
| SEQ ID NO: 42 | m28 | Ser$^{117}$Asn$^{118}$Ala$^{119}$Gly$^{120}$Phe$^{121}$<br>is: SNAGF |
| SEQ ID NO: 43 | m30 | Thr$^{117}$Asn$^{118}$Ala$^{119}$Gly$^{120}$Phe$^{121}$<br>is: TNAGF |
| SEQ ID NO: 44 | m33 | Asn$^{117}$Asn$^{118}$Ala$^{119}$Gly$^{120}$Phe$^{121}$<br>is: NNAGF |
| SEQ ID NO: 45 | m1 | Glu$^{117}$Asn$^{118}$Ala$^{119}$Gly$^{120}$Met$^{121}$<br>is: ENAGM |
| SEQ ID NO: 46 | m3 | Trp$^{117}$Asn$^{118}$Ala$^{119}$Cys$^{120}$Cys$^{121}$<br>is: WNACC |
| SEQ ID NO: 47 | m8 | Met$^{117}$Asn$^{118}$Ala$^{119}$Phe$^{120}$Val$^{121}$<br>is: MNAFV |
| SEQ ID NO: 48 | m15 | Ala$^{117}$Asn$^{118}$Ala$^{119}$Asp$^{120}$Trp$^{121}$<br>is: ANADW |
| SEQ ID NO: 49 | m6 | Ser$^{117}$Asn$^{118}$Ala$^{119}$Met$^{120}$Met$^{121}$<br>is: SNAMM |
| SEQ ID NO: 50 | m9 | Arg$^{117}$Asn$^{118}$Ala$^{119}$Val$^{120}$Val$^{121}$<br>is: RNAVV |
| SEQ ID NO: 51 | m20 | Ser$^{117}$Asn$^{118}$Ala$^{119}$Ser$^{120}$Phe$^{121}$<br>is: SNASF |
| SEQ ID NO: 52 | m34 | Ala$^{117}$---$^{118}$---$^{119}$Trp$^{120}$Asp$^{121}$<br>is: AXXWD |
| SEQ ID NO: 53 | m14 | Arg$^{117}$Asn$^{118}$Ala$^{119}$Arg$^{120}$Ala$^{121}$<br>is: RNARA |
| SEQ ID NO: 54 | m18 | Ser$^{117}$Asn$^{118}$Ala$^{119}$Ala$^{120}$Phe$^{121}$<br>is: SNAAF |
| SEQ ID NO: 55 | m19 | Gly$^{117}$Asn$^{118}$Ala$^{11}$9Met$^{120}$Met$^{121}$<br>is: GNAMM |
| SEQ ID NO: 56 | m8 | Glu$^{117}$Asn$^{118}$Ala$^{119}$Gly$^{120}$Phe$^{121}$<br>is: ENAGF |
| SEQ ID NO: 57 | m21 | Asp$^{117}$Asn$^{118}$Ala$^{119}$Gly$^{120}$Tyr$^{121}$<br>is: DNAGY |
| SEQ ID NO: 58 | m9 | Glu$^{117}$Asn$^{118}$Ala$^{119}$Gly$^{120}$Tyr$^{121}$<br>is: ENAGY |
| SEQ ID NO: 59 | m1 | Arg$^{117}$Asn$^{118}$Ala$^{119}$Met$^{120}$Met$^{121}$<br>is: RNAMM |

TABLE 13-continued

| SEQ ID NO | Name | Sequence |
|---|---|---|
| SEQ ID NO: 60 | m2 | $Arg^{117}Asn^{118}Ala^{119}Gly^{120}Phe^{121}$ is: RNAGF |
| SEQ ID NO: 61 | m3 | $Ala^{117}Asn^{118}Ala^{119}Pro^{120}Ala^{121}$ is: ANAPA |
| SEQ ID NO: 62 | m5 | $Ala^{117}Asn^{118}Ala^{119}Met^{120}Val^{121}$ is: ANAMV |
| SEQ ID NO: 63 | m13 | $Gln^{117}Asn^{118}Ala^{119}Ser^{120}Ala^{121}$ is: QNASA |
| SEQ ID NO: 64 | m14 | $Ala^{117}Asn^{118}Ala^{119}Gly^{120}Phe^{121}$ is: ANAGF |
| SEQ ID NO: 65 | m24 | $Gln^{117}Asn^{118}Ala^{119}Met^{120}Val^{121}$ is: QNAMV |
| SEQ ID NO: 66 | m4 | $Asn^{117}Asn^{118}Ala^{119}Gly^{120}Tyr^{121}$ is: NNAGY |
| SEQ ID NO: 67 | m6 | $Ala^{117}Asn^{118}Ala^{119}Ala^{120}Val^{121}$ is: ANAAV |
| SEQ ID NO: 68 | m7 | $Ser^{117}Asn^{118}Ala^{119}Met^{120}Ile^{121}$ is: SNAMI |
| SEQ ID NO: 69 | m10 | $His^{117}Asn^{118}Ala^{119}Gly^{120}Tyr^{121}$ is: HNAGY |
| SEQ ID NO: 70 | m15 | $Ser^{117}Asn^{118}Ala^{119}Met^{120}Ala^{121}$ is: SNAMA |
| SEQ ID NO: 71 | m23 | $Gln^{117}Asn^{118}Ala^{119}Val^{120}Ala^{121}$ is: QNAVA |
| SEQ ID NO: 72 | m17 | $Tyr^{117}Asn^{118}Ala^{119}Tyr^{120}Met^{121}$ is: YNAYM |
| SEQ ID NO: 73 | m12 | $Leu^{117}Asn^{118}Ala^{119}Trp^{120}Gly^{121}$ is: LNAWG |
| SEQ ID NO: 74 | m20 | $His^{117}Asn^{118}Ala^{119}Ser^{120}Met^{121}$ is: HNASM |
| SEQ ID NO: 75 | m101 | $Tyr^{117}Asn^{118}Ala^{119}Phe^{120}Leu^{121}$ is: YNAFL |
| SEQ ID NO: 76 | m106 | $Phe^{117}Asn^{118}Ala^{119}Phe^{120}Leu^{121}$ is: FNAFL |
| SEQ ID NO: 77 | m111 | $Tyr^{117}Asn^{118}Ala^{119}Leu^{120}Trp^{121}$ is: YNALW |
| SEQ ID NO: 78 | m100 | $Phe^{117}Asn^{118}Ala^{119}Tyr^{120}Ile^{121}$ is: FNAYI |
| SEQ ID NO: 79 | m110 | $Tyr^{117}Asn^{118}Ala^{119}Tyr^{120}Leu^{121}$ is: YNAYL |
| SEQ ID NO: 80 | m104 | $Tyr^{117}Asn^{118}Ala^{119}Tyr^{120}Gln^{121}$ is: YNAYQ |
| SEQ ID NO: 81 | m108 | $Phe^{117}Asn^{118}Ala^{119}Ile^{120}Trp^{121}$ is: FNAIW |
| SEQ ID NO: 82 | m207 | $Thr^{117}---^{118}---^{119}Trp^{120}Leu^{121}$ is: TXXWL |
| SEQ ID NO: 83 | m212 | $His^{117}---^{118}---^{119}Trp^{120}Leu^{121}$ is: HXXWL |
| SEQ ID NO: 84 | m202 | $Ile^{117}---^{118}---^{119}Trp^{120}Arg^{121}$ is: IXXWR |
| SEQ ID NO: 85 | m204 | $His^{117}---^{118}---^{119}Trp^{120}Thr^{121}$ is: HXXWT |

TABLE 13-continued

| SEQ ID NO | Name | Sequence |
|---|---|---|
| SEQ ID NO: 86 | m206 | Thr$^{117}$---$^{118}$---$^{119}$Trp$^{120}$Arg$^{121}$<br>is: TXXWR |
| SEQ ID NO: 87 | m208 | Ala$^{117}$---$^{118}$---$^{119}$Trp$^{120}$Arg$^{121}$<br>is: AXXWR |
| SEQ ID NO: 88 | m203 | Arg$^{117}$---$^{118}$---$^{119}$Trp$^{120}$Ser$^{121}$<br>is: RXXWS |
| SEQ ID NO: 89 | m209 | Asn$^{117}$---$^{118}$---$^{119}$Trp$^{120}$Arg$^{121}$<br>is: NXXWR |
| SEQ ID NO: 90 | m200 | Lys$^{117}$---$^{118}$---$^{119}$Trp$^{120}$Ser$^{121}$<br>is: KXXWS |
| SEQ ID NO: 91 | m201 | Ser$^{117}$---$^{118}$---$^{119}$Val$^{120}$Phe$^{121}$<br>is: SXXVF |
| SEQ ID NO: 92 | m211 | Lys$^{117}$---$^{118}$---$^{119}$Trp$^{120}$Thr$^{121}$<br>is: KXXWT |
| SEQ ID NO: 93 | m300 | Ala$^{117}$---$^{118}$---$^{119}$Trp$^{120}$Tyr$^{121}$<br>is: AXXWY |
| SEQ ID NO: 94 | m301 | His$^{117}$---$^{118}$---$^{119}$Trp$^{120}$Met$^{121}$<br>is: HXXWM |
| SEQ ID NO: 95 | m302 | His$^{117}$---$^{118}$---$^{119}$Trp$^{120}$Tyr$^{121}$<br>is: HXXWY |
| SEQ ID NO: 96 | m303 | Glu$^{117}$---$^{118}$---$^{119}$Trp$^{120}$Tyr$^{121}$<br>is: EXXWY |
| SEQ ID NO: 97 | m304 | Gln$^{117}$---$^{118}$---$^{119}$Trp$^{120}$Tyr$^{121}$<br>is: QXXWY |
| SEQ ID NO: 98 | streptavidin mutein<br>(44-47 = VTAR) | Val$^{44}$-Thr$^{45}$-Ala$^{46}$-Arg$^{47}$<br>is: VTAR |
| SEQ ID NO: 99 | streptavidin mutein | Ile$^{44}$-Gly$^{45}$-Ala$^{46}$-Arg$^{47}$<br>is: IGAR |
| SEQ ID NO: 100 | Strep-tag II affinity peptide ligand | Trp-Ser-His-Pro-Gln-Phe-Glu-Lys<br>is: WSHPQFEK |
| SEQ ID NO: 101 | peptide sequence | Trp-Xaa-His-Pro-Gln-Phe-Yaa-Zaa<br>in which Xaa represents an arbitrary amino acid and<br>Yaa and Zaa either both denote Gly or Yaa denotes<br>Glu and Zaa denotes Arg or Lys<br>is WXHPQFXX |
| SEQ ID NO: 102 | Strep-tag streptavidin binding peptide | Trp-Arg-His-Pro-Gln-Phe-Gly-Gly (WRHPQFGG) |
| SEQ ID NO: 103 | Peptide sequence | Trp-Ser-His-Pro-Gln-Phe-Glu-Lys-(GlyGlyGlySer)$_3$-Trp-<br>Ser-His-Pro-Gln-Phe-Glu-Lys<br>Is WSHPQFEKGGGSGGGSGGGSWSHPQFEK |
| SEQ ID NO: 104 | GFP-StrepII | |
| SEQ ID NO: 105 | GFP-di-tag3 | |
| SEQ ID NO: 106 | Cytb562-StrepII | |
| SEQ ID NO: 107 | Cytb562-di-tag3 | |
| SEQ ID NO: 108 | peptide sequence | Oaa-Xaa-His-Pro-Gln-Phe-Yaa-Zaa<br>where Oaa is Trp, Lys or Arg, Xaa is any amino acid<br>and where either Yaa and Zaa are both Gly or Yaa is<br>Glu and Zaa is Lys or Arg is XXHPQFXX |
| SEQ ID NO: 109 | di-tag2 | Trp-Ser-His-Pro-Gln-Phe-Glu-Lys-(GlyGlyGlySer)$_2$-Trp-<br>Ser-His-Pro-Gln-Phe-Glu-Lys<br>Is WSHPQFEKGGGSGGGSWSHPQFEK |
| SEQ ID NO: 110 | Peptide sequence | WSHPQFEKGGGSGGGSGGSAWSHPQFEK |
| SEQ ID NO: 111 | Wildtype | FIG. 4 |

TABLE 13-continued

| SEQ ID NO | Name | Sequence |
|---|---|---|
| SEQ ID NO: 112 | mutein"1 | FIG. 4 |
| SEQ ID NO: 113 | mutein"2 | FIG. 4 |
| SEQ ID NO: 114 | m400 | FIG. 4 |
| SEQ ID NO: 115 | m402 | FIG. 4 |
| SEQ ID NO: 116 | m4001 | FIG. 4 |
| SEQ ID NO: 117 | mutein"1"-m36 | FIG. 4 |
| SEQ ID NO: 118 | mutein"1"-m23 | FIG. 4 |
| SEQ ID NO: 119 | mutein"1"-m41 | FIG. 4 |
| SEQ ID NO: 120 | mutein"1"-m4 | FIG. 4 |
| SEQ ID NO: 121 | mutein"1"-m12 | FIG. 4 |
| SEQ ID NO: 122 | mutein"1"-m22 | FIG. 4 |
| SEQ ID NO: 123 | mutein"1"-m31 | FIG. 4 |
| SEQ ID NO: 124 | mutein"1"-m32 | FIG. 4 |
| SEQ ID NO: 125 | mutein"1"-m35 | FIG. 4 |
| SEQ ID NO: 126 | mutein"1"-m38 | FIG. 4 |
| SEQ ID NO: 127 | mutein"1"-m40 | FIG. 4 |
| SEQ ID NO: 128 | mutein"1"-m42 | FIG. 4 |
| SEQ ID NO: 129 | mutein"1"-m45 | FIG. 4 |
| SEQ ID NO: 130 | mutein"1"-m46 | FIG. 4 |
| SEQ ID NO: 131 | mutein"1"-m47 | FIG. 4 |
| SEQ ID NO: 132 | mutein"1"-m7 | FIG. 4 |
| SEQ ID NO: 133 | mutein"1"-m10 | FIG. 4 |
| SEQ ID NO: 134 | mutein"1"-m17 | FIG. 4 |
| SEQ ID NO: 135 | mutein"1"-m21 | FIG. 4 |
| SEQ ID NO: 136 | mutein"1"-m24 | FIG. 4 |
| SEQ ID NO: 137 | mutein"1"-m27 | FIG. 4 |
| SEQ ID NO: 138 | mutein"1"-m28 | FIG. 4 |
| SEQ ID NO: 139 | mutein"1"-m30 | FIG. 4 |
| SEQ ID NO: 140 | mutein"1"-m33 | FIG. 4 |
| SEQ ID NO: 141 | mutein"1"-m1 | FIG. 4 |
| SEQ ID NO: 142 | mutein"1"-m3 | FIG. 4 |
| SEQ ID NO: 143 | mutein"1"-m8 | FIG. 4 |
| SEQ ID NO: 144 | mutein"1"-m15 | FIG. 4 |
| SEQ ID NO: 145 | mutein"1"-m6 | FIG. 4 |
| SEQ ID NO: 146 | mutein"1"-m9 | FIG. 4 |
| SEQ ID NO: 147 | mutein"1"-m20 | FIG. 4 |
| SEQ ID NO: 148 | mutein"1"-m34 | FIG. 4 |
| SEQ ID NO: 149 | mutein"1"-m14 | FIG. 4 |
| SEQ ID NO: 150 | mutein"1"-m18 | FIG. 4 |

TABLE 13-continued

| SEQ ID NO | Name | Sequence |
|---|---|---|
| SEQ ID NO: 151 | mutein"1"-m19 | FIG. 4 |
| SEQ ID NO: 152 | m4001-m8 | FIG. 4 |
| SEQ ID NO: 153 | m4001-m21 | FIG. 4 |
| SEQ ID NO: 154 | m4001-m9 | FIG. 4 |
| SEQ ID NO: 155 | m4001-m1 | FIG. 4 |
| SEQ ID NO: 156 | m4001-m2 | FIG. 4 |
| SEQ ID NO: 157 | m4001-m3 | FIG. 4 |
| SEQ ID NO: 158 | m4001-m5 | FIG. 4 |
| SEQ ID NO: 159 | m4001-m13 | FIG. 4 |
| SEQ ID NO: 160 | m4001-m14 | FIG. 4 |
| SEQ ID NO: 161 | m4001-m24 | FIG. 4 |
| SEQ ID NO: 162 | m4001-m4 | FIG. 4 |
| SEQ ID NO: 163 | m4001-m6 | FIG. 4 |
| SEQ ID NO: 164 | m4001-m7 | FIG. 4 |
| SEQ ID NO: 165 | m4001-m10 | FIG. 4 |
| SEQ ID NO: 166 | m4001-m15 | FIG. 4 |
| SEQ ID NO: 167 | m4001-m23 | FIG. 4 |
| SEQ ID NO: 168 | m4001-m17 | FIG. 4 |
| SEQ ID NO: 169 | m4001-m12 | FIG. 4 |
| SEQ ID NO: 170 | m4001-m20 | FIG. 4 |
| SEQ ID NO: 171 | mutein"1"-m101 | FIG. 4 |
| SEQ ID NO: 172 | mutein"1"-m106 | FIG. 4 |
| SEQ ID NO: 173 | mutein"1"-m111 | FIG. 4 |
| SEQ ID NO: 174 | mutein"1"-m100 | FIG. 4 |
| SEQ ID NO: 175 | mutein"1"-m110 | FIG. 4 |
| SEQ ID NO: 176 | mutein"1"-m104 | FIG. 4 |
| SEQ ID NO: 177 | mutein"1"-m108 | FIG. 4 |
| SEQ ID NO: 178 | mutein"1"-m207 | FIG. 4 |
| SEQ ID NO: 179 | mutein"1"-m212 | FIG. 4 |
| SEQ ID NO: 180 | mutein"1"-m202 | FIG. 4 |
| SEQ ID NO: 181 | mutein"1"-m204 | FIG. 4 |
| SEQ ID NO: 182 | mutein"1"-m206 | FIG. 4 |
| SEQ ID NO: 183 | mutein"1"-m208 | FIG. 4 |
| SEQ ID NO: 184 | mutein"1"-m203 | FIG. 4 |
| SEQ ID NO: 185 | mutein"1"-m209 | FIG. 4 |
| SEQ ID NO: 186 | mutein"1"-m200 | FIG. 4 |
| SEQ ID NO: 187 | mutein"1"-m201 | FIG. 4 |
| SEQ ID NO: 188 | mutein"1"-m211 | FIG. 4 |
| SEQ ID NO: 189 | mutein"1"-m300 | FIG. 4 |

TABLE 13-continued

| SEQ ID NO | Name | Sequence |
|---|---|---|
| SEQ ID NO: 190 | mutein"1"-m301 | FIG. 4 |
| SEQ ID NO: 191 | mutein"1"-m302 | FIG. 4 |
| SEQ ID NO: 192 | mutein"1"-m303 | FIG. 4 |
| SEQ ID NO: 193 | mutein"1"-m304 | FIG. 4 |
| SEQ ID NO: 194 | Mutein m1-9 | FIG. 4 |
| SEQ ID NO: 195 | loop of the amino acids 114 to 121 of streptavidin | TTEANAWK |
| SEQ ID NO: 196 | loop region of amino acids 115 to 121 of streptavidin | TEANAWK |
| SEQ ID NO: 197 | mutein | HPYFYAPELLFFAK |
| SEQ ID NO: 198 | mutein motif1 consensus sequence1 | EGGKETLTPSELRDLV $Xaa^{117}Gly^{120}Yaa^{121}$, wherein Xaa may be any amino acid and Yaa may be Phe or Tyr or Met is XGX- so not more than 4 amino acids |
| SEQ ID NO: 199 | motif1 (FIG. 2B) motif2 consensus sequence2 | Xaa Asn Ala Gly Zaa, Xaa is Glu, Asp, Arg, His, Asn, Gln, Thr, Ser, Leu, Met and Zaa is Phe, Tyr, Met is XNAGX $Aaa^{112}Baa^{120}Caa^{121}$, wherein Aaa may be Tyr, Phe, Arg, Trp or Gln, Baa may be Tyr, Phe, Leu, Ile or Met and Caa may be any amino acid, wherein Caa121 is preferably a Leu, an Ile, a Met, a Gly, a Trp, a Ser, an Ala or a Val residue |
| SEQ ID NO: 200 | Motif2 (FIG. 2B) | Xaa-Asn-Ala-Yaa-Zaa, wherein Xaa is Tyr, Phe, Arg, Trp, Gln; Yaa is Tyr, Phe, Leu, Ile, Met and Zaa is Leu, Ile, Met, Gln, Gly, Trp, Ser, Ala, Val Is XNAXX |
| SEQ ID NO: 201 | motif3 consensus sequence3 | $Daa^{117}Eaa^{118}Faa^{119}Gaa^{120}Haa^{121}$, wherein Daa and Haa may be any amino acid and Eaa and Faa are both deleted and Gaa may be Trp or Val, wherein $Daa^{117}$ is preferably a His, a Glu, a Gln, a Thr, an Ala or an Ile residue and wherein $Haa^{121}$ is preferably a Tyr, a Leu, a Met, or an Arg residue is XXXXX |
| SEQ ID NO: 202 | Motif2 (FIG. 2B) | Xaa --- --- Yaa Zaa, wherein Xaa is His, Glu, Gln, Thr, Ala, Ile, Arg, Asn, Lys, Ser; Yaa is Trp, Val and Zaa is Tyr, Leu, Met, Arg, Thr, Ser, Phe Is XXXXX |
| SEQ ID NO: 203 | Library 1 | Xaa$^{44}$Xaa$^{45}$Ala$^{46}$Arg$^{47}$Gly$^{48}$Asn$^{49}$Ala$^{50}$Glu$^{51}$Xaa$^{52}$ is XXARGNAEX |
| SEQ ID NO: 204 | Library 2 | (Ala/Gly)44Cys45Xaa46Xaa47Gly48Asn49Ala50Glu51 Cys52 is XCXXGNAEC |
| SEQ ID NO: 205 | Wt (Library 2) | Glu$^{44}$Ser$^{45}$Ala$^{46}$Val$^{47}$Gly$^{48}$Asn$^{49}$Ala$^{50}$Glu$^{51}$Ser$^{52}$ is ESAVGNAES |
| SEQ ID NO: 206 | Library 3 | $Xaa^{117}Asn^{118}Ala^{119}\textbf{Xaa}^{120}\textbf{Xaa}^{121}$ Is XNAXX |
| SEQ ID NO: 207 | Wt (Library 2) mutein "1" (Library 2) Wt (Library 4) m4001 (Library 4) Wt (Library 5) mutein "1" (Library 5) Wt (Library 6) mutein "1" (Library 6) Wt (Library 7) mutein "1" (Library 7) | $Ala^{171}Asn^{118}Ala^{119}Trp^{120}Lys^{121}$ Is ANAWK |
| SEQ ID NO: 208 | Library 4 | Xaa$^{117}$Asn$^{118}$Ala$^{119}$Xaa$^{120}$Xaa$^{121}$ is XNAXX |

TABLE 13-continued

| SEQ ID NO | Name | Sequence |
|---|---|---|
| SEQ ID NO: 209 | Library 5 | (Phe/Tyr)$^{117}$Asn$^{118}$Ala$^{119}$Xaa$^{120}$Xaa$^{121}$ is XNAXX |
| SEQ ID NO: 210 | Library 6 | Xaa$^{117}$---$^{118}$---$^{119}$Xaa$^{120}$Xaa$^{121}$ is XXXXX |
| SEQ ID NO: 211 | Library 7 | Xaa$^{117}$---$^{118}$---$^{119}$Trp$^{120}$Xaa$^{121}$ is XXXWX |
| SEQ ID NO: 212 | Wt streptavidin amino acid sequence (residues 14 to 139) | EAGITGTWYNQLGSTFIVTAGADGALTGTYESAVGNAESRYVLTGRYDSAPATDGSGTALGWTVAWKNNYRNAHSATTWSGQYVGGAEARINTQWLLTSGTTEANAWKSTLVGHDTFTKVKPSAAS |

---

What is claimed is:

1. A mutein, selected from muteins of streptavidin, wherein the mutein
   (a) contains at least two cysteine residues in the region of the amino acid positions 44 to 53 with reference to the amino acid sequence of wild type streptavidin as set forth at SEQ ID NO: 212 and
   (b) has a higher binding affinity than
   (i) a streptavidin mutein "1" (SEQ ID NO: 112) that comprises the amino acid sequence Val$^{44}$-Thr$^{45}$-Ala$^{46}$-Arg$^{47}$ (SEQ ID NO: 98), or
   (ii) wild type-streptavidin of which amino acid residues 14 to 139 are shown as SEQ ID NO: 212 for peptide ligands comprising the amino acid sequence Trp-Ser-His-Pro-Gln-Phe-Glu-Lys (SEQ ID NO: 100).

2. A mutein according to claim 1, wherein the two cysteine residues are present at opposing positions in the loop formed by the residues of amino acid positions 44 to 53.

3. A mutein according to claim 1, wherein the two cysteine residues are present at amino acid positions 45 and 52 of wild type streptavidin.

4. A mutein according to claim 1, wherein the two cysteine residues are present at positions 44 and 53 of wild type streptavidin.

5. A mutein according to claim 1, wherein the two cysteine residues are present at positions 46 and 51 of wild type streptavidin.

6. A mutein according to claim 1, wherein the two cysteine residues are present at positions 47 and 50 of wild type streptavidin.

7. A mutein according to claim 1, wherein the two cysteine residues are present at positions 48 and 49 of wild type streptavidin.

8. A mutein according to claim 1, wherein a Gly or an Ala residue is present at amino acid position 44 of wild type streptavidin.

9. A mutein according to claim 1, wherein the amino acid residue at sequence position 46 is glycine.

10. A mutein according to claim 9, wherein the amino acid residue at sequence position 46 is glycine and the amino acid residue at sequence position 47 is arginine.

11. A mutein according to claim 1, wherein the mutein comprises an amino acid sequence at sequence positions 44 to 52 with reference to the amino acid sequence of wild type streptavidin as set forth at SEQ ID NO: 212 selected from the group consisting of (SEQ ID NO: 18)
Gly$^{44}$Cys$^{45}$Ala$^{46}$Arg$^{47}$Gly$^{48}$Asn$^{49}$Ala$^{50}$Glu$^{51}$Cys$^{52}$ (SEQ ID NO: 19)
Ala$^{44}$Cys$^{45}$Ala$^{46}$Arg$^{47}$Gly$^{48}$Asn$^{49}$Ala$^{50}$Glu$^{51}$Cys$^{52}$,
and (SEQ ID NO: 20)
Ala$^{44}$Cys$^{45}$Gly$^{46}$Arg$^{47}$Gly$^{48}$Asn$^{49}$Ala$^{50}$Glu$^{51}$Cys$^{52}$.

12. A mutein according to claim 1, wherein the mutein comprises the sequence of a mutein selected from the group consisting of mutein m400 (SEQ ID NO: 114), mutein m402 (SEQ ID NO: 115) and mutein m4001 (SEQ ID NO: 116).

13. A streptavidin mutein according to claim 1, wherein the mutein contains at least one mutation in the region of the amino acid positions 117 to 121 with reference to the amino acid sequence of wild type streptavidin of which amino acid residues 14 to 139 are as set forth at SEQ ID NO: 212.

14. A mutein according to claim 13, wherein the mutein contains two or more mutations in the region of the amino acid positions 117 to 121 with reference to the amino acid sequence of wild type streptavidin of which amino acid residues 14 to 139 are as set forth at SEQ ID NO: 212,
   wherein the mutein carries as mutated residue at sequence position 117 an amino acid residue selected from the group consisting of Glu, Asp, His, Gln and Arg or,
   wherein the mutein carries either the wild-type Trp at sequence position 120 or carries as mutated residue at sequence position 120 an amino acid residue selected from the group consisting of Ser, Gly, Met, and Pro, or
   wherein the mutein carries as mutated residue at sequence position 121 an amino acid residue selected from the group consisting of Leu, Tyr, Phe, and Met.

15. A mutein according to claim 1, wherein the mutein is a mutein of a minimal streptavidin which begins N-terminally in the region of the amino acids 10 to 16 of wild type streptavidin and terminates C-terminally in the region of the amino acids 133-142 of wild type streptavidin.

16. A mutein according to claim 1, wherein the binding affinity for the peptide ligand is such that a competitive elution can take place by streptavidin ligands selected from the group consisting of biotin, thiobiotin, iminobiotin, lipoic acid, desthiobiotin, diaminobiotin, HABA and dimethyl-HABA.

17. A nucleic acid molecule, comprising a nucleic acid sequence coding for a streptavidin mutein according to claim 1.

18. A method of producing of a streptavidin mutein according to claim 1, comprising:
   (a) transforming a suitable host cell with a vector which contains a nucleic acid coding for the streptavidin mutein,
   (b) culturing the host cell under conditions in which an expression of the streptavidin mutein takes place,
   (c) isolating the mutein.

19. A method of isolating, purifying or determining a protein that is fused with a) a peptide sequence of the formula Trp-Xaa-His-Pro-Gln-Phe-Yaa-Zaa (SEQ ID NO: 101) in which Xaa represents an arbitrary amino acid and Yaa and Zaa either both denote Gly or Yaa denotes Glu and Zaa denotes Arg or Lys, or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa-(SEQ ID NO: 108) where Oaa is Trp, Lys or Arg, Xaa is any amino acid and where either Yaa and Zaa are both Gly or Yaa is Glu and Zaa is Lys or Arg, comprising contacting a sample containing the protein with a streptavidin mutein of claim 1, under suitable conditions to bind the peptide sequence to the streptavidin mutein, and separating resulting complex from said sample.

* * * * *

SEQUENCE LISTING

<160> NUMBER OF SEQ ID NOS: 212

<210> SEQ ID NO 1
<211> LENGTH: 4568
<212> TYPE: DNA
<213> ORGANISM: Artificial Sequence
<220> FEATURE:
<223> OTHER INFORMATION: E. coli alkaline phosphatase Strep-tag II
      fusion protein (BAP-StrepII) - expressed by pASK75-phoA

<400> SEQUENCE: 1

```
ccatcgaatg gccagatgat taattcctaa tttttgttga cactctatca ttgatagagt      60
tattttacca ctccctatca gtgatagaga aagtgaaat gaatagttcg acaaaaatct      120
agaacatgga gaaataaag tgaaacaaag cactattgca ctggcactct taccgttact      180
gtttacccct gtgacaaaag cccggacacc agaaatgcct gttctggaaa accgggctgc      240
tcagggcgat attactgcac ccggcggtgc tcgccgttta acgggtgatc agactgccgc      300
tctgcgtgat tctcttagcg ataaacctgc aaaaaatatt attttgctga ttggcgatgg      360 gatggggac tcgaaatta ctgccgcacg taattatgcc gaaggtgcgg gcggttttt      420 taaaggtata gatgccttac cgcttaccgg gcaatacact cactatgcgc tgaataaaaa      480
aaccggcaaa ccggactacg tcaccgactc ggctgcatca gcaaccgcct ggtcaaccgg      540
tgtcaaaacc tataacggcg cgctgggcgt cgatattcac gaaaaagatc acccaacgat      600
tctgaaaatg gcaaaagccg caggtctggc gaccggtaac gtttctaccg cagagttgca      660
ggatgccacg cccgctgcgc tggtggcaca tgtgacctcg cgcaaatgct acggtccgag      720
cgcgaccagt gaaaaatgtc cgggtaacgc tctggaaaaa ggcggaaaag atcgattac      780 cgaacagctg cttaacgctc gtgccgacgt tacgcttggc ggcggcgcaa aaacctttgc      840
tgaaacggca accgctggtg aatggcaggg aaaaacgctg cgtgaacagg cacaggcgcg      900
tggttatcag ttggtgagcg atgctgcctc actgaattcg gtgacggaag cgaatcagca      960 aaaaccctg cttggcctgt tgctgacgg caatatgcca gtgcgctggc taggaccgaa      1020
agcaacgtac catggcaata tcgataagcc cgcagtcacc tgtacgccaa atccgcaacg      1080
taatgacagt gtaccaaccc tggcgcagat gaccgacaaa gccattgaat tgttgagtaa      1140
aaatgagaaa ggctttttcc tgcaagttga aggtgcgtca atcgataaac aggatcatgc      1200
tgcgaatcct tgtgggcaaa ttggcgagac ggtcgatctc gatgaagccg tacaacgggc      1260
gctggaattc gctaaaaagg agggtaacac gctggtcata gtcaccgctg atcacgccca      1320
```

-continued

```
cgccagccag attgttgcgc cggataccaa agctccgggc ctcacccagg cgctaaatac      1380
caaagatggc gcagtgatgg tgatgagtta cgggaactcc gaagaggatt cacaagaaca      1440
taccggcagt cagttgcgta ttgcggcgta tggcccgcat gccgccaatg ttgttggact      1500
gaccgaccag accgatctct tctacaccat gaaagccgct ctggggctga aaccgcctag      1560
cgcttggtct cacccgcagt tcgaaaaata ataagcttga cctgtgaagt gaaaatggc      1620 gcacattgtg cgacattttt tttgtctgcc gtttaccgct actgcgtcac ggatctccac      1680
gcgccctgta gcggcgcatt aagcgcggcg ggtgtggtgg ttacgcgcag cgtgaccgct      1740
acacttgcca gcgccctagc gcccgctcct ttcgctttct tcccttcctt tctcgccacg      1800
ttcgccggct ttccccgtca gctctaaat cgggggctcc ctttagggtt ccgatttagt      1860
gctttacggc acctcgaccc caaaaaactt gattagggtg atggttcacg tagtgggcca      1920
tcgccctgat agacggtttt tcgccctttg acgttggagt ccacgttctt taatagtgga      1980
ctcttgttcc aaactggaac aacactcaac cctatctcgg tctattcttt tgatttataa      2040
gggattttgc cgatttcggc ctattggtta aaaaatgagc tgatttaaca aaaatttaac      2100
gcgaatttta acaaaatatt aacgcttaca atttcaggtg gcacttttcg gggaaatgtg      2160
cgcggaaccc ctatttgttt attttttctaa atacattcaa atatgtatcc gctcatgaga      2220
caataaccct gataaatgct tcaataatat tgaaaaagga agagtatgag tattcaacat      2280
ttccgtgtcg cccttattcc cttttttgcg gcattttgcc ttcctgtttt tgctcaccca      2340
gaaacgctgg tgaaagtaaa agatgctgaa gatcagttgg gtgcacgagt gggttacatc      2400
gaactggatc tcaacagcgg taagatcctt gagagttttc gccccgaaga acgttttcca      2460
atgatgagca cttttaaagt tctgctatgt ggcgcggtat tatcccgtat tgacgccggg      2520
caagagcaac tcggtcgccg catacactat tctcagaatg acttggttga gtactcacca      2580
gtcacagaaa agcatcttac ggatggcatg acagtaagag aattatgcag tgctgccata      2640
accatgagtg ataacactgc ggccaactta cttctgacaa cgatcggagg accgaaggag      2700
ctaaccgctt ttttgcacaa catgggggat catgtaactc gccttgatcg ttgggaaccg      2760
gagctgaatg aagccatacc aaacgacgag cgtgacacca cgatgcctgt agcaatggca      2820
acaacgttgc gcaaactatt aactggcgaa ctacttactc tagcttcccg gcaacaattg      2880
atagactgga tggaggcgga taaagttgca ggaccacttc tgcgctcggc ccttccggct      2940
ggctggttta ttgctgataa atctggagcc ggtgagcgtg gctctcgcgg tatcattgca      3000
gcactggggc cagatggtaa gccctcccgt atcgtagtta tctacacgac ggggagtcag      3060
gcaactatgg atgaacgaaa tagacagatc gctgagatag gtgcctcact gattaagcat      3120
tggtaggaat taatgatgtc tcgtttagat aaaagtaaag tgattaacag cgcattagag      3180
ctgcttaatg aggtcggaat cgaaggttta acaacccgta aactcgccca agcctaggt     3240 gtagagcagc ctacattgta ttggcatgta aaaaataagc gggctttgct cgacgcctta      3300
gccattgaga tgttagatag gcaccatact cacttttgcc ctttagaagg ggaaagctgg      3360
caagattttt tacgtaataa cgctaaaagt tttagatgtg ctttactaag tcatcgcgat      3420
ggagcaaaag tacatttagg tacacggcct acagaaaaac agtatgaaac tctcgaaaat      3480
caattagcct ttttatgcca acaaggtttt tcactagaga atgcattata tgcactcagc      3540
gcagtggggc attttacttt aggttgcgta ttggaagatc aagagcatca agtcgctaaa      3600
gaagaaaggg aaacacctac tactgatagt atgccgccat tattacgaca agctatcgaa      3660
ttatttgatc accaaggtgc agagccagcc ttcttattcg gccttgaatt gatcatatgc      3720
```

```
ggattagaaa acaaacttaa atgtgaaagt gggtcttaaa agcagcataa ccttttttccg    3780 tgatggtaac ttcactagtt taaaaggatc taggtgaaga tccttttttga taatctcatg    3840 accaaaatcc cttaacgtga gttttcgttc cactgagcgt cagacccccgt agaaaagatc    3900 aaaggatctt cttgagatcc ttttttttctg cgcgtaatct gctgcttgca acaaaaaaaa    3960
ccaccgctac cagcggtggt ttgtttgccg gatcaagagc taccaactct ttttccgaag    4020
gtaactggct tcagcagagc gcagatacca aatactgtcc ttctagtgta gccgtagtta    4080
ggccaccact tcaagaactc tgtagcaccg cctacatacc tcgctctgct aatcctgtta    4140
ccagtggctg ctgccagtgg cgataagtcg tgtcttaccg ggttggactc aagacgatag    4200
ttaccggata aggcgcagcg gtcgggctga acggggggtt cgtgcacaca gcccagcttg    4260
gagcgaacga cctacaccga actgagatac ctacagcgtg agctatgaga aagcgccacg    4320
cttcccgaag ggagaaaggc ggacaggtat ccggtaagcg gcagggtcgg aacaggagag    4380
cgcacgaggg agcttccagg gggaaacgcc tggtatcttt atagtcctgt cgggtttcgc    4440
cacctctgac ttgagcgtcg atttttgtga tgctcgtcag ggggggcggag cctatggaaa    4500 aacgccagca acgcggcctt tttacggttc ctggccttttt gctggccttt tgctcacatg    4560
acccgaca                                                              4568

<210> SEQ ID NO 2
<211> LENGTH: 3535
<212> TYPE: DNA
<213> ORGANISM: Artificial Sequence
<220> FEATURE:
<223> OTHER INFORMATION: plasmid pASK-IBA2-cytochromeb562

<400> SEQUENCE: 2
ccatcgaatg gccagatgat taattcctaa ttttttgttga cactctatca ttgatagagt      60
tattttacca ctccctatca gtgatagaga aagtgaaat gaatagttcg acaaaaatct      120
agataacgag ggcaaaaaat gaaaaagaca gctatcgcga ttgcagtggc actggctggt     180
ttcgctaccg tagcgcaggc cgctgatctt gaagacaata tggaaaccct caacgacaat     240
ttaaaagtga tcgaaaaagc ggataacgcg gcgcaagtca aagacgcgtt aacgaagatg     300
cgcgccgcag ccctggatgc gcaaaaagca acgccgccga agctcgaaga taaatcaccg     360
gacagcccgg aaatgaaaga tttccgccac ggtttcgaca ttctggtcgg tcagattgac    420
gacgcgctga gctggcaaa tgaaggtaaa gtaaagaag cgcaggctgc tgcagagcaa     480
ctgaaaacga cccgcaacgc ctatcaccag aagtatcgtc cgccgagcgc ttggagccac    540
ccgcagttcg aaaaataata agcttgacct gtgaagtgaa aaatggcgca cattgtgcga    600 cattttttt gtctgccgtt taccgctact gcgtcacgga tctccacgcg ccctgtagcg    660
gcgcattaag cgcggcgggt gtggtggtta cgcgcagcgt gaccgctaca cttgccagcg    720
ccctagcgcc cgctcctttc gctttcttcc cttcctttct cgccacgttc gccggctttc    780
cccgtcaagc tctaaatcgg gggctccctt tagggttccg atttagtgct ttacggcacc    840
tcgaccccaa aaaacttgat tagggtgatg gttcacgtag tgggccatcg ccctgataga    900 cggttttttcg ccctttgacg ttggagtcca cgttctttaa tagtggactc ttgttccaaa    960
ctggaacaac actcaaccct atctcggtct attctttttga tttataaggg attttgccga    1020
tttcggccta ttggttaaaa aatgagctga tttaacaaaa atttaacgcg aattttaaca    1080
aaatattaac gcttacaatt tcaggtggca cttttcgggg aaatgtgcgc ggaacccta    1140
```

```
tttgtttatt tttctaaata cattcaaata tgtatccgct catgagacaa taaccctgat    1200
aaatgcttca ataatattga aaaggaaga gtatgagtat tcaacatttc cgtgtcgccc    1260 ttattcccctt ttttgcggca ttttgccttc ctgttttttgc tcacccagaa acgctggtga  1320
aagtaaaaga tgctgaagat cagttgggtg cacgagtggg ttacatcgaa ctggatctca    1380
acagcggtaa gatccttgag agttttcgcc ccgaagaacg ttttccaatg atgagcactt    1440
ttaaagttct gctatgtggc gcggtattat cccgtattga cgccgggcaa gagcaactcg    1500
gtcgccgcat acactattct cagaatgact tggttgagta ctcaccagtc acagaaaagc    1560
atcttacgga tggcatgaca gtaagagaat tatgcagtgc tgccataacc atgagtgata    1620
acactgcggc caacttactt ctgacaacga tcggaggacc gaaggagcta accgcttttt    1680
tgcacaacat gggggatcat gtaactcgcc ttgatcgttg ggaaccggag ctgaatgaag    1740
ccataccaaa cgacgagcgt gacaccacga tgcctgtagc aatggcaaca acgttgcgca    1800
aactattaac tggcgaacta cttactctag cttcccggca acaattgata gactggatgg    1860
aggcggataa agttgcagga ccacttctgc gctcggccct tccggctggc tggtttattg    1920
ctgataaatc tggagccggt gagcgtggct ctcgcggtat cattgcagca ctggggccag    1980
atggtaagcc ctcccgtatc gtagttatct acacgacggg gagtcaggca actatggatg    2040
aacgaaatag acagatcgct gagataggtg cctcactgat taagcattgg taggaattaa    2100
tgatgtctcg tttagataaa agtaaagtga ttaacagcgc attagagctg cttaatgagg    2160
tcggaatcga aggtttaaca acccgtaaac tcgcccagaa gctaggtgta gagcagccta    2220
cattgtattg gcatgtaaaa aataagcggg ctttgctcga cgccttagcc attgagatgt    2280
tagataggca ccatactcac ttttgccctt agaaggggga agctggcaa gattttttac     2340 gtaataacgc taaaagttttt agatgtgctt tactaagtca tcgcgatgga gcaaaagtac   2400
atttaggtac acggcctaca gaaaaacagt atgaaactct cgaaaatcaa ttagccttttt   2460 tatgccaaca aggttttttca ctagagaatg cattatatgc actcagcgca gtggggcatt   2520
ttactttagg ttgcgtattg aagatcaag agcatcaagt cgctaaagaa gaaagggaaa    2580
cacctactac tgatagtatg ccgccattat tacgacaagc tatcgaatta tttgatcacc    2640
aaggtgcaga gccagccttc ttattcggcc ttgaattgat catatgcgga ttagaaaaac    2700
aacttaaatg tgaaagtggg tcttaaaagc agcataacct ttttccgtga tggtaacttc    2760
actagtttaa aaggatctag gtgaagatcc ttttttgataa tctcatgacc aaaatccctt    2820
aacgtgagtt tcgttccac tgagcgtcag accccgtaga aaagatcaaa ggatcttctt     2880
gagatccttt ttttctgcgc gtaatctgct gcttgcaaac aaaaaaacca ccgctaccag    2940
cggtggtttg tttgccggat caagagctac caactctttt tccgaaggta actggcttca    3000
gcagagcgca gataccaaat actgtccttc tagtgtagcc gtagttaggc caccacttca    3060
agaactctgt agcaccgcct acatacctcg ctctgctaat cctgttacca gtggctgctg    3120
ccagtggcga taagtcgtgt cttaccgggt tggactcaag acgatagtta ccggataagg    3180
cgcagcggtc gggctgaacg gggggttcgt gcacacagcc cagcttggag cgaacgacct    3240
acaccgaact gagatacccta cagcgtgagc tatgagaaag cgccacgctt cccgaaggga    3300
gaaaggcgga caggtatccg gtaagcggca gggtcggaac aggagagcgc acgagggagc    3360
ttccaggggg aaacgcctgg tatctttata gtcctgtcgg gtttcgccac ctctgacttg    3420
agcgtcgatt tttgtgatgc tcgtcagggg ggcggagcct atggaaaaac gccagcaacg    3480
cggccttttt acggttcctg gccttttgct ggccttttgc tcacatgacc cgaca          3535
```

<210> SEQ ID NO 3
<211> LENGTH: 3562
<212> TYPE: DNA
<213> ORGANISM: Artificial sequence
<220> FEATURE:
<223> OTHER INFORMATION: nucleotide sequence of the expression vector pASK-IBA2-SAm1 which contains a sequence coding for the OmpA signal peptide followed by the sequence coding for streptavidin mutein "1" disclosed by US 6,103,493

<400> SEQUENCE: 3

```
ccatcgaatg gccagatgat taattcctaa ttttgttga cactctatca ttgatagagt      60
tattttacca ctccctatca gtgatagaga aagtgaaat gaatagttcg acaaaaatct     120
agataacgag ggcaaaaaat gaaaagaca gctatcgcga ttgcagtggc actggctggt     180
ttcgctaccg tagcgcaggc tgcagaagca ggtatcaccg gcacctggta caaccagctc    240
ggctcgacct tcatcgtgac cgcgggtgca gacggagctc tgaccggtac ctacgtcacg    300
gcgcgtggca acgccgagag ccgctacgtc ctgaccggtc gttacgacag cgccccggcc    360
accgacggca gcggcaccgc cctcggttgg acggtggcct ggaagaataa ctaccgcaac    420
gcccactccg cgaccacgtg gagcggccag tacgtcggcg gcgccgaggc gaggatcaac    480
acccagtggc tgctgacctc cggcaccacc gaggccaacg cctggaagtc cacgctggtc    540
ggccacgaca ccttcaccaa ggtgaagccg tccgccgcct cctaataagc ttgacctgtg    600
aagtgaaaaa tggcgcacat tgtgcgacat ttttttgtc tgccgtttac cgctactgcg    660
tcacggatct ccacgcgccc tgtagcgcg cattaagcgc ggcgggtgtg gtggttacgc    720
gcagcgtgac cgctacactt gccagcgccc tagcgcccgc tcctttcgct ttcttccctt    780
cctttctcgc cacgttcgcc ggctttcccc gtcaagctct aaatcggggg ctccctttag    840
ggttccgatt tagtgcttta cggcacctcg accccaaaaa acttgattag ggtgatggtt    900
cacgtagtgg gccatcgccc tgatagacgg ttttccgccc tttgacgttg gagtccacgt    960
tctttaatag tggactcttg ttccaaactg gaacaacact caaccctatc tcggtctatt   1020
cttttgattt ataagggatt tgccgattt cggcctattg gttaaaaaat gagctgattt    1080
aacaaaaatt taacgcgaat tttaacaaaa tattaacgct tacaatttca ggtggcactt   1140
ttcggggaaa tgtgcgcgga accctattt gtttattttt ctaaatacat tcaaatatgt    1200
atccgctcat gagacaataa ccctgataaa tgcttcaata atattgaaaa aggaagagta   1260
tgagtattca acatttccgt gtcgccctta ttccctttt tgcggcattt tgccttcctg    1320
ttttgctca cccagaaacg ctggtgaaag taaaagatgc tgaagatcag ttgggtgcac    1380
gagtgggtta catcgaactg gatctcaaca gcggtaagat ccttgagagt tttcgccccg   1440
aagaacgttt tccaatgatg agcacttta aagttctgct atgtggcgcg gtattatccc   1500
gtattgacgc cgggcaagag caactcggtc gccgcataca ctattctcag aatgacttgg   1560
ttgagtactc accagtcaca gaaaagcatc ttacggatgg catgacagta agagaattat    1620
gcagtgctgc cataaccatg agtgataaca ctgcggccaa cttacttctg acaacgatcg    1680
gaggaccgaa ggagctaacc gcttttttgc acaacatggg gatcatgta actcgccttg    1740
atcgttggga accggagctg aatgaagcca taccaaacga cgagcgtgac accacgatgc    1800
ctgtagcaat ggcaacaacg ttgcgcaaac tattaactgg cgaactactt actctagctt   1860
cccggcaaca attgatagac tggatggagg cggataaagt tgcaggacca cttctgcgct   1920
cggcccttcc ggctggctgg tttattgctg ataaatctgg agccggtgag cgtggctctc   1980
```

```
gcggtatcat tgcagcactg gggccagatg gtaagccctc ccgtatcgta gttatctaca    2040
cgacggggag tcaggcaact atggatgaac gaaatagaca gatcgctgag ataggtgcct    2100
cactgattaa gcattggtag gaattaatga tgtctcgttt agataaaagt aaagtgatta    2160
acagcgcatt agagctgctt aatgaggtcg gaatcgaagg tttaacaacc cgtaaactcg    2220
cccagaagct aggtgtagag cagcctacat tgtattggca tgtaaaaaat aagcgggctt    2280
tgctcgacgc cttagccatt gagatgttag ataggcacca tactcacttt tgcccttttag   2340 aaggggaaag ctggcaagat tttttacgta ataacgctaa aagttttaga tgtgctttac    2400
taagtcatcg cgatggagca aaagtacatt taggtacacg gcctacagaa aaacagtatg    2460
aaactctcga aaatcaatta gccttttttat gccaacaagg ttttttcacta gagaatgcat   2520 tatatgcact cagcgcagtg gggcattttta ctttaggttg cgtattggaa gatcaagagc   2580
atcaagtcgc taaagaagaa agggaaacac ctactactga tagtatgccg ccattattac    2640
gacaagctat cgaattattt gatcaccaag gtgcagagcc agccttctta ttcggccttg    2700
aattgatcat atgcggatta gaaaaacaac ttaaatgtga aagtgggtct taaaagcagc    2760
ataacctttt tccgtgatgg taacttcact agtttaaaag gatctaggtg aagatccttt    2820
ttgataatct catgaccaaa atcccttaac gtgagttttc gttccactga gcgtcagacc    2880
ccgtagaaaa gatcaaagga tcttcttgag atccttttttt tctgcgcgta atctgctgct    2940
tgcaaacaaa aaaaccaccg ctaccagcgg tggtttgttt gccggatcaa gagctaccaa    3000
ctctttttcc gaaggtaact ggcttcagca gagcgcagat accaaatact gtccttctag    3060
tgtagccgta gttaggccac cacttcaaga actctgtagc accgcctaca tacctcgctc    3120
tgctaatcct gttaccagtg gctgctgcca gtggcgataa gtcgtgtctt accgggttgg    3180
actcaagacg atagttaccg gataaggcgc agcggtcggg ctgaacgggg ggttcgtgca    3240
cacagcccag cttggagcga acgacctaca ccgaactgag atacctacag cgtgagctat    3300
gagaaagcgc cacgcttccc gaagggagaa aggcggacag gtatccggta agcggcaggg    3360
tcggaacagg agagcgcacg agggagcttc caggggggaaa cgcctggtat ctttatagtc    3420
ctgtcgggtt tcgccacctc tgacttgagc gtcgatttttt gtgatgctcg tcagggggc    3480 ggagcctatg gaaaaacgcc agcaacgcgg cctttttacg gttcctggcc ttttgctggc    3540
cttttgctca catgacccga ca                                              3562

<210> SEQ ID NO 4
<211> LENGTH: 3562
<212> TYPE: DNA
<213> ORGANISM: Artificial Sequence
<220> FEATURE:
<223> OTHER INFORMATION: nucleotide sequence of the expression vector
      pASK-IBA2-SAm4001 which contains a sequence coding for the OmpA
      signal peptide followed by the sequence coding for streptavidin
      mutein m4001

<400> SEQUENCE: 4
ccatcgaatg gccagatgat taattcctaa ttttttgttga cactctatca ttgatagagt       60
tattttacca ctccctatca gtgatagaga aaagtgaaat gaatagttcg acaaaaatct      120
agataacgag ggcaaaaaat gaaaaagaca gctatcgcga ttgcagtggc actggctggt      180
ttcgctaccg tagcgcaggc tgcagaagca ggtatcaccg gcacctggta caaccagctc      240
ggctcgacct tcatcgtgac cgcgggtgca gacggagctc tgaccggtac ctacgcttgc      300
ggccggggca acgccgagtg ccgctacgtc ctgaccggtc gttacgacag cgccccggcc      360
```

```
accgacggca gcggcaccgc cctcggttgg acggtggcct ggaagaataa ctaccgcaac      420
gcccactccg cgaccacgtg gagcggccag tacgtcggcg gcgccgaggc gaggatcaac      480
acccagtggc tgctgacctc cggcaccacc gaggccaacg cctggaagtc cacgctggtc      540
ggccacgaca ccttcaccaa ggtgaagccg tccgccgcct cctaataagc ttgacctgtg      600
aagtgaaaaa tggcgcacat tgtgcgacat tttttttgtc tgccgtttac cgctactgcg      660
tcacggatct ccacgcgccc tgtagcggcg cattaagcgc ggcgggtgtg gtggttacgc      720
gcagcgtgac cgctacactt gccagcgccc tagcgcccgc tcctttcgct ttcttccctt      780
cctttctcgc cacgttcgcc ggctttcccc gtcaagctct aaatcggggg ctccctttag      840
ggttccgatt tagtgcttta cggcacctcg accccaaaaa acttgattag ggtgatggtt      900
cacgtagtgg gccatcgccc tgatagacgg ttttcgccc tttgacgttg gagtccacgt      960
tctttaatag tggactcttg ttccaaactg gaacaacact caaccctatc tcggtctatt     1020
cttttgattt ataagggatt tgccgatttc ggcctattg gttaaaaaat gagctgattt     1080
aacaaaaatt taacgcgaat tttaacaaaa tattaacgct tacaatttca ggtggcactt     1140
ttcggggaaa tgtgcgcgga acccctattt gtttattttt ctaaatacat tcaaatatgt     1200
atccgctcat gagacaataa ccctgataaa tgcttcaata atattgaaaa aggaagagta     1260
tgagtattca acatttccgt gtcgccctta ttccctttt tgcggcattt tgccttcctg     1320
tttttgctca cccagaaacg ctggtgaaag taaaagatgc tgaagatcag ttgggtgcac     1380
gagtgggtta catcgaactg gatctcaaca gcggtaagat ccttgagagt tttcgccccg     1440
aagaacgttt tccaatgatg agcacttta aagttctgct atgtggcgcg gtattatccc     1500
gtattgacgc cgggcaagag caactcggtc gccgcataca ctattctcag aatgacttgg     1560
ttgagtactc accagtcaca gaaaagcatc ttacggatgg catgacagta agagaattat     1620
gcagtgctgc cataaccatg agtgataaca ctgcggccaa cttacttctg acaacgatcg     1680
gaggaccgaa ggagctaacc gcttttttgc acaacatggg ggatcatgta actcgccttg     1740
atcgttggga accggagctg aatgaagcca taccaaacga cgagcgtgac accacgatgc     1800
ctgtagcaat ggcaacaacg ttgcgcaaac tattaactgg cgaactactt actctagctt     1860
cccggcaaca attgatagac tggatggagg cggataaagt tgcaggacca cttctgcgct     1920
cggcccttcc ggctggctgg tttattgctg ataaatctgg agccggtgag cgtggctctc     1980
gcggtatcat tgcagcactg gggccagatg gtaagccctc ccgtatcgta gttatctaca     2040
cgacggggag tcaggcaact atggatgaac gaaatagaca gatcgctgag ataggtgcct     2100
cactgattaa gcattggtag gaattaatga tgtctcgttt agataaaagt aaagtgatta     2160
acagcgcatt agagctgctt aatgaggtcg gaatcgaagg tttaacaacc cgtaaactcg     2220
cccagaagct aggtgtagag cagcctacat tgtattggca tgtaaaaaat aagcgggctt     2280
tgctcgacgc cttagccatt gagatgttag ataggcacca tactcacttt tgccctttag     2340
aaggggaaag ctggcaagat tttttacgta ataacgctaa aagttttaga tgtgctttac     2400
taagtcatcg cgatggagca aaagtacatt taggtacacg gcctacagaa aaacagtatg     2460
aaactctcga aaatcaatta gccttttat gccaacaagg ttttcacta gagaatgcat     2520 tatatgcact cagcgcagtg gggcatttta ctttaggttg cgtattggaa gatcaagagc     2580
atcaagtcgc taaagaagaa agggaaacac ctactactga tagtatgccg ccattattac     2640
gacaagctat cgaattattt gatcaccaag gtgcagagcc agccttctta ttcggccttg     2700
```

-continued

```
aattgatcat atgcggatta gaaaaacaac ttaaatgtga aagtgggtct taaaagcagc   2760
ataacctttt tccgtgatgg taacttcact agtttaaaag gatctaggtg aagatccttt   2820
ttgataatct catgaccaaa atcccttaac gtgagttttc gttccactga gcgtcagacc   2880
ccgtagaaaa gatcaaagga tcttcttgag atcctttttt tctgcgcgta atctgctgct   2940
tgcaaacaaa aaaaccaccg ctaccagcgg tggtttgttt gccggatcaa gagctaccaa   3000 ctcttttcc gaaggtaact ggcttcagca gagcgcagat accaaatact gtccttctag    3060
tgtagccgta gttaggccac cacttcaaga actctgtagc accgcctaca tacctcgctc    3120
tgctaatcct gttaccagtg gctgctgcca gtggcgataa gtcgtgtctt accgggttgg    3180
actcaagacg atagttaccg gataaggcgc agcggtcggg ctgaacgggg ggttcgtgca    3240
cacagcccag cttggagcga acgacctaca ccgaactgag atacctacag cgtgagctat    3300
gagaaagcgc cacgcttccc gaagggagaa aggcggacag gtatccggta agcggcaggg    3360
tcggaacagg agagcgcacg agggagcttc caggggaaa cgcctggtat ctttatagtc     3420
ctgtcgggtt tcgccacctc tgacttgagc gtcgattttt gtgatgctcg tcagggggc     3480 ggagcctatg gaaaaacgcc agcaacgcgg ccttttacg gttcctggcc ttttgctggc     3540
cttttgctca catgacccga ca                                             3562
```

<210> SEQ ID NO 5
<211> LENGTH: 90
<212> TYPE: DNA
<213> ORGANISM: Artificial Sequence
<220> FEATURE:
<223> OTHER INFORMATION: Primer 1
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (44)..(44)
<223> OTHER INFORMATION: s is g or c
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (68)..(68)
<223> OTHER INFORMATION: s is g or c

<400> SEQUENCE: 5

```
tcgtgaccgc gggtgcagac ggagctctga ccggtaccta cnnsnnkgcg cgtggcaacg   60
ccgagnnscg ctacgtcctg accggtcgtt                                     90
```

<210> SEQ ID NO 6
<211> LENGTH: 19
<212> TYPE: DNA
<213> ORGANISM: Artificial Sequence
<220> FEATURE:
<223> OTHER INFORMATION: Primer 2

<400> SEQUENCE: 6

```
agtagcggta aacggcaga                                                 19
```

<210> SEQ ID NO 7
<211> LENGTH: 55
<212> TYPE: DNA
<213> ORGANISM: Artificial Sequence
<220> FEATURE:
<223> OTHER INFORMATION: Primer 3
<220> FEATURE:
<221> NAME/KEY: misc_feature
<222> LOCATION: (17)..(17)
<223> OTHER INFORMATION: s is g or c
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: s is g or c
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t

<400> SEQUENCE: 7
ctgaccggta cctacgsttg cnnsnnkggc aacgccgagt gccgctacgt cctga        55

<210> SEQ ID NO 8
<211> LENGTH: 26
<212> TYPE: DNA
<213> ORGANISM: Artificial Sequence
<220> FEATURE:
<223> OTHER INFORMATION: Primer 4
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: k is g or t

<400> SEQUENCE: 8
gccnnsnnkt ccacgctggt cggcca        26

<210> SEQ ID NO 9
<211> LENGTH: 24
<212> TYPE: DNA
<213> ORGANISM: Artificial Sequence
<220> FEATURE:
<223> OTHER INFORMATION: Primer 5
<220> FEATURE:
<221> NAME/KEY: misc_feature
<222> LOCATION: (5)..(5)
<223> OTHER INFORMATION: m is a or c
<220> FEATURE:
<221> NAME/KEY: misc_feature
<222> LOCATION: (6)..(6)
<223> OTHER INFORMATION: n is a, c, g, or t

<400> SEQUENCE: 9
gttmnnctcg gtggtgccgg aggt                                              24

<210> SEQ ID NO 10
<211> LENGTH: 24
<212> TYPE: DNA
<213> ORGANISM: Artificial Sequence
<220> FEATURE:
<223> OTHER INFORMATION: Primer 6
<220> FEATURE:
<221> NAME/KEY: misc_feature
<222> LOCATION: (5)..(5)
<223> OTHER INFORMATION: m is a or c

<400> SEQUENCE: 10
gttamactcg gtggtgccgg aggt                                              24

<210> SEQ ID NO 11
<211> LENGTH: 23
<212> TYPE: DNA
<213> ORGANISM: Artificial Sequence
<220> FEATURE:
<223> OTHER INFORMATION: Primer 7
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
<223> OTHER INFORMATION: s is g or c
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: k is g or t

<400> SEQUENCE: 11
nsnnktccac gctggtcggc cac                                               23

<210> SEQ ID NO 12
<211> LENGTH: 22
<212> TYPE: DNA
<213> ORGANISM: Artificial Sequence
<220> FEATURE:
<223> OTHER INFORMATION: Primer 8
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
<223> OTHER INFORMATION: m is a or c
<220> FEATURE:
<221> NAME/KEY: misc_feature
<222> LOCATION: (3)..(4)
<223> OTHER INFORMATION: n is a, c, g, or t

<400> SEQUENCE: 12
nmnnctcggt ggtgccggag gt                                                22

<210> SEQ ID NO 13
<211> LENGTH: 23
<212> TYPE: DNA
<213> ORGANISM: Artificial Sequence
<220> FEATURE:
<223> OTHER INFORMATION: Primer 9
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (5)..(5)
<223> OTHER INFORMATION: k is g or t

<400> SEQUENCE: 13
ggnnktccac gctggtcggc cac    23

<210> SEQ ID NO 14
<211> LENGTH: 22
<212> TYPE: DNA
<213> ORGANISM: Artificial Sequence
<220> FEATURE:
<223> OTHER INFORMATION: Primer 10
<220> FEATURE:
<221> NAME/KEY: misc_feature
<222> LOCATION: (2)..(2)
<223> OTHER INFORMATION: m is a or c
<220> FEATURE:
<221> NAME/KEY: misc_feature
<222> LOCATION: (3)..(4)
<223> OTHER INFORMATION: n is a, c, g, or t

<400> SEQUENCE: 14
amnnctcggt ggtgccggag gt    22

<210> SEQ ID NO 15
<211> LENGTH: 9
<212> TYPE: PRT
<213> ORGANISM: Artificial Sequence
<220> FEATURE:
<223> OTHER INFORMATION: Streptavidin wildtype

<400> SEQUENCE: 15

Glu Ser Ala Val Gly Asn Ala Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: mutein 1

<400> SEQUENCE: 16

Val Thr Ala Arg Gly Asn Ala Glu Ser
1               5

<210> SEQ ID NO 17
<211> LENGTH: 4
<212> TYPE: PRT
<213> ORGANISM: Artificial Sequence
<220> FEATURE:
<223> OTHER INFORMATION: mutein 2

<400> SEQUENCE: 17

Ile Gly Ala Arg
1

<210> SEQ ID NO 18
<211> LENGTH: 9
<212> TYPE: PRT
<213> ORGANISM: Artificial Sequence
<220> FEATURE:
<223> OTHER INFORMATION: m400 fragment

<400> SEQUENCE: 18

```
Gly Cys Ala Arg Gly Asn Ala Glu Cys
1               5

<210> SEQ ID NO 19
<211> LENGTH: 9
<212> TYPE: PRT
<213> ORGANISM: Artificial Sequence
<220> FEATURE:
<223> OTHER INFORMATION: m402 fragment

<400> SEQUENCE: 19

Ala Cys Ala Arg Gly Asn Ala Glu Cys
1               5

<210> SEQ ID NO 20
<211> LENGTH: 9
<212> TYPE: PRT
<213> ORGANISM: Artificial Sequence
<220> FEATURE:
<223> OTHER INFORMATION: m4001 fragment

<400> SEQUENCE: 20

Ala Cys Gly Arg Gly Asn Ala Glu Cys
1               5

<210> SEQ ID NO 21
<211> LENGTH: 5
<212> TYPE: PRT
<213> ORGANISM: Artificial Sequence
<220> FEATURE:
<223> OTHER INFORMATION: m36 fragment

<400> SEQUENCE: 21

Tyr Asn Ala Phe Met
1               5

<210> SEQ ID NO 22
<211> LENGTH: 5
<212> TYPE: PRT
<213> ORGANISM: Artificial Sequence
<220> FEATURE:
<223> OTHER INFORMATION: m23 fragment

<400> SEQUENCE: 22

Tyr Asn Ala Tyr Ala
1               5

<210> SEQ ID NO 23
<211> LENGTH: 5
<212> TYPE: PRT
<213> ORGANISM: Artificial Sequence
<220> FEATURE:
<223> OTHER INFORMATION: m41 fragment
<220> FEATURE:
<221> NAME/KEY: MISC_FEATURE
<222> LOCATION: (2)..(3)
<223> OTHER INFORMATION: amino acid deletion

<400> SEQUENCE: 23

Ala Xaa Xaa Trp Tyr
1               5

<210> SEQ ID NO 24
<211> LENGTH: 5
<212> TYPE: PRT
<213> ORGANISM: Artificial Sequence
<220> FEATURE:
```

```
<223> OTHER INFORMATION: m4 fragment

<400> SEQUENCE: 24

Asp Asn Ala Gly Phe
1               5

<210> SEQ ID NO 25
<211> LENGTH: 5
<212> TYPE: PRT
<213> ORGANISM: Artificial Sequence
<220> FEATURE:
<223> OTHER INFORMATION: m12 fragment

<400> SEQUENCE: 25

Arg Asn Ala Gly Phe
1               5

<210> SEQ ID NO 26
<211> LENGTH: 5
<212> TYPE: PRT
<213> ORGANISM: Artificial Sequence
<220> FEATURE:
<223> OTHER INFORMATION: m22 fragment

<400> SEQUENCE: 26

Gln Asn Ala Gly Phe
1               5

<210> SEQ ID NO 27
<211> LENGTH: 5
<212> TYPE: PRT
<213> ORGANISM: Artificial Sequence
<220> FEATURE:
<223> OTHER INFORMATION: m31 fragment

<400> SEQUENCE: 27

Phe Asn Ala Ser Trp
1               5

<210> SEQ ID NO 28
<211> LENGTH: 5
<212> TYPE: PRT
<213> ORGANISM: Artificial Sequence
<220> FEATURE:
<223> OTHER INFORMATION: m32 fragment

<400> SEQUENCE: 28

Asp Asn Ala Val Met
1               5

<210> SEQ ID NO 29
<211> LENGTH: 5
<212> TYPE: PRT
<213> ORGANISM: Artificial Sequence
<220> FEATURE:
<223> OTHER INFORMATION: m35 fragment
<220> FEATURE:
<221> NAME/KEY: MISC_FEATURE
<222> LOCATION: (2)..(3)
<223> OTHER INFORMATION: amino acid deletion

<400> SEQUENCE: 29

Ala Xaa Xaa Trp Met
1               5

<210> SEQ ID NO 30
<211> LENGTH: 5
```

```
<212> TYPE: PRT
<213> ORGANISM: Artificial Sequence
<220> FEATURE:
<223> OTHER INFORMATION: m38 fragment

<400> SEQUENCE: 30

Glu Asn Ala Gly Phe
1               5

<210> SEQ ID NO 31
<211> LENGTH: 5
<212> TYPE: PRT
<213> ORGANISM: Artificial Sequence
<220> FEATURE:
<223> OTHER INFORMATION: m40 fragment

<400> SEQUENCE: 31

Tyr Asn Ala Tyr Ser
1               5

<210> SEQ ID NO 32
<211> LENGTH: 5
<212> TYPE: PRT
<213> ORGANISM: Artificial Sequence
<220> FEATURE:
<223> OTHER INFORMATION: m 42 fragment

<400> SEQUENCE: 32

Phe Asn Ala Tyr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: m45 fragment

<400> SEQUENCE: 33

Tyr Asn Ala Gly Phe
1               5

<210> SEQ ID NO 34
<211> LENGTH: 5
<212> TYPE: PRT
<213> ORGANISM: Artificial Sequence
<220> FEATURE:
<223> OTHER INFORMATION: m46 fragment

<400> SEQUENCE: 34

Arg Asn Ala Tyr Ala
1               5

<210> SEQ ID NO 35
<211> LENGTH: 5
<212> TYPE: PRT
<213> ORGANISM: Artificial Sequence
<220> FEATURE:
<223> OTHER INFORMATION: m47 fragment

<400> SEQUENCE: 35

Trp Asn Ala Tyr Gly
1               5

<210> SEQ ID NO 36
<211> LENGTH: 5
<212> TYPE: PRT
```

```
<213> ORGANISM: Artificial Sequence
<220> FEATURE:
<223> OTHER INFORMATION: m7 fragment

<400> SEQUENCE: 36

Leu Asn Ala Gly Phe
1               5

<210> SEQ ID NO 37
<211> LENGTH: 5
<212> TYPE: PRT
<213> ORGANISM: Artificial Sequence
<220> FEATURE:
<223> OTHER INFORMATION: m10 fragment

<400> SEQUENCE: 37

His Asn Ala Gly Tyr
1               5

<210> SEQ ID NO 38
<211> LENGTH: 5
<212> TYPE: PRT
<213> ORGANISM: Artificial Sequence
<220> FEATURE:
<223> OTHER INFORMATION: m17 fragment

<400> SEQUENCE: 38

Met Asn Ala Gly Phe
1               5

<210> SEQ ID NO 39
<211> LENGTH: 5
<212> TYPE: PRT
<213> ORGANISM: Artificial Sequence
<220> FEATURE:
<223> OTHER INFORMATION: m21 fragment

<400> SEQUENCE: 39

Arg Asn Ala Gly Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: m24 fragment

<400> SEQUENCE: 40

Glu Asn Ala Gly Trp
1               5

<210> SEQ ID NO 41
<211> LENGTH: 5
<212> TYPE: PRT
<213> ORGANISM: Artificial Sequence
<220> FEATURE:
<223> OTHER INFORMATION: m27 fragment

<400> SEQUENCE: 41

His Asn Ala Gly Phe
1               5

<210> SEQ ID NO 42
<211> LENGTH: 5
<212> TYPE: PRT
<213> ORGANISM: Artificial Sequence
```

```
<220> FEATURE:
<223> OTHER INFORMATION: m28 fragment

<400> SEQUENCE: 42

Ser Asn Ala Gly Phe
1               5

<210> SEQ ID NO 43
<211> LENGTH: 5
<212> TYPE: PRT
<213> ORGANISM: Artificial Sequence
<220> FEATURE:
<223> OTHER INFORMATION: m30 fragment

<400> SEQUENCE: 43

Thr Asn Ala Gly Phe
1               5

<210> SEQ ID NO 44
<211> LENGTH: 5
<212> TYPE: PRT
<213> ORGANISM: Artificial Sequence
<220> FEATURE:
<223> OTHER INFORMATION: m33 fragment

<400> SEQUENCE: 44

Asn Asn Ala Gly Phe
1               5

<210> SEQ ID NO 45
<211> LENGTH: 5
<212> TYPE: PRT
<213> ORGANISM: Artificial Sequence
<220> FEATURE:
<223> OTHER INFORMATION: m1 frag,ent

<400> SEQUENCE: 45

Glu Asn Ala Gly Met
1               5

<210> SEQ ID NO 46
<211> LENGTH: 5
<212> TYPE: PRT
<213> ORGANISM: Artificial Sequence
<220> FEATURE:
<223> OTHER INFORMATION: m3 fragment

<400> SEQUENCE: 46

Trp Asn Ala Cys Cys
1               5

<210> SEQ ID NO 47
<211> LENGTH: 5
<212> TYPE: PRT
<213> ORGANISM: Artificial Sequence
<220> FEATURE:
<223> OTHER INFORMATION: m8 fragment

<400> SEQUENCE: 47

Met Asn Ala Phe Val
1               5

<210> SEQ ID NO 48
<211> LENGTH: 5
<212> TYPE: PRT
<213> ORGANISM: Artificial Sequence
<220> FEATURE:
```

<223> OTHER INFORMATION: m15 fragment

<400> SEQUENCE: 48

Ala Asn Ala Asp Trp
1               5

<210> SEQ ID NO 49
<211> LENGTH: 5
<212> TYPE: PRT
<213> ORGANISM: Artificial Sequence
<220> FEATURE:
<223> OTHER INFORMATION: m6 fragment

<400> SEQUENCE: 49

Ser Asn Ala Met Met
1               5

<210> SEQ ID NO 50
<211> LENGTH: 5
<212> TYPE: PRT
<213> ORGANISM: Artificial Sequence
<220> FEATURE:
<223> OTHER INFORMATION: m9 fragment

<400> SEQUENCE: 50

Arg Asn Ala Val Val
1               5

<210> SEQ ID NO 51
<211> LENGTH: 5
<212> TYPE: PRT
<213> ORGANISM: Artificial Sequence
<220> FEATURE:
<223> OTHER INFORMATION: m20 fragment

<400> SEQUENCE: 51

Ser Asn Ala Ser Phe
1               5

<210> SEQ ID NO 52
<211> LENGTH: 5
<212> TYPE: PRT
<213> ORGANISM: Artificial Sequence
<220> FEATURE:
<223> OTHER INFORMATION: m34 fragment
<220> FEATURE:
<221> NAME/KEY: MISC_FEATURE
<222> LOCATION: (2)..(3)
<223> OTHER INFORMATION: amino acid deletion

<400> SEQUENCE: 52

Ala Xaa Xaa Trp Asp
1               5

<210> SEQ ID NO 53
<211> LENGTH: 5
<212> TYPE: PRT
<213> ORGANISM: Artificial Sequence
<220> FEATURE:
<223> OTHER INFORMATION: m14 fragment

<400> SEQUENCE: 53

Arg Asn Ala Arg Ala
1               5

<210> SEQ ID NO 54
<211> LENGTH: 5

```
<212> TYPE: PRT
<213> ORGANISM: Artificial Sequence
<220> FEATURE:
<223> OTHER INFORMATION: m18 fragment

<400> SEQUENCE: 54

Ser Asn Ala Ala Phe
1               5

<210> SEQ ID NO 55
<211> LENGTH: 5
<212> TYPE: PRT
<213> ORGANISM: Artificial Sequence
<220> FEATURE:
<223> OTHER INFORMATION: m19 fragment

<400> SEQUENCE: 55

Gly Asn Ala Met Met
1               5

<210> SEQ ID NO 56
<211> LENGTH: 5
<212> TYPE: PRT
<213> ORGANISM: Artificial Sequence
<220> FEATURE:
<223> OTHER INFORMATION: m8 fragment

<400> SEQUENCE: 56

Glu Asn Ala Gly Phe
1               5

<210> SEQ ID NO 57
<211> LENGTH: 5
<212> TYPE: PRT
<213> ORGANISM: Artificial Sequence
<220> FEATURE:
<223> OTHER INFORMATION: m21 fragment

<400> SEQUENCE: 57

Asp Asn Ala Gly Tyr
1               5

<210> SEQ ID NO 58
<211> LENGTH: 5
<212> TYPE: PRT
<213> ORGANISM: Artificial Sequence
<220> FEATURE:
<223> OTHER INFORMATION: m9 fragment

<400> SEQUENCE: 58

Glu Asn Ala Gly Tyr
1               5

<210> SEQ ID NO 59
<211> LENGTH: 5
<212> TYPE: PRT
<213> ORGANISM: Artificial Sequence
<220> FEATURE:
<223> OTHER INFORMATION: m1 fragment

<400> SEQUENCE: 59

Arg Asn Ala Met Met
1               5

<210> SEQ ID NO 60
<211> LENGTH: 5
<212> TYPE: PRT
```

```
<213> ORGANISM: Artificial Sequence
<220> FEATURE:
<223> OTHER INFORMATION: m2 fragment

<400> SEQUENCE: 60

Arg Asn Ala Gly Phe
1               5

<210> SEQ ID NO 61
<211> LENGTH: 5
<212> TYPE: PRT
<213> ORGANISM: Artificial Sequence
<220> FEATURE:
<223> OTHER INFORMATION: m3 fragment

<400> SEQUENCE: 61

Ala Asn Ala Pro Ala
1               5

<210> SEQ ID NO 62
<211> LENGTH: 5
<212> TYPE: PRT
<213> ORGANISM: Artificial Sequence
<220> FEATURE:
<223> OTHER INFORMATION: m5 fragment

<400> SEQUENCE: 62

Ala Asn Ala Met Val
1               5

<210> SEQ ID NO 63
<211> LENGTH: 5
<212> TYPE: PRT
<213> ORGANISM: Artificial Sequence
<220> FEATURE:
<223> OTHER INFORMATION: m13 fragment

<400> SEQUENCE: 63

Gln Asn Ala Ser Ala
1               5

<210> SEQ ID NO 64
<211> LENGTH: 5
<212> TYPE: PRT
<213> ORGANISM: Artificial Sequence
<220> FEATURE:
<223> OTHER INFORMATION: m14 fragment

<400> SEQUENCE: 64

Ala Asn Ala Gly Phe
1               5

<210> SEQ ID NO 65
<211> LENGTH: 5
<212> TYPE: PRT
<213> ORGANISM: Artificial Sequence
<220> FEATURE:
<223> OTHER INFORMATION: m24 fragemnt

<400> SEQUENCE: 65

Gln Asn Ala Met Val
1               5

<210> SEQ ID NO 66
<211> LENGTH: 5
<212> TYPE: PRT
<213> ORGANISM: Artificial Sequence
```

```
<220> FEATURE:
<223> OTHER INFORMATION: m4 fragment

<400> SEQUENCE: 66

Asn Asn Ala Gly Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: m6 fragment

<400> SEQUENCE: 67

Ala Asn Ala Ala Val
1               5

<210> SEQ ID NO 68
<211> LENGTH: 5
<212> TYPE: PRT
<213> ORGANISM: Artificial Sequence
<220> FEATURE:
<223> OTHER INFORMATION: m7 fragment

<400> SEQUENCE: 68

Ser Asn Ala Met Ile
1               5

<210> SEQ ID NO 69
<211> LENGTH: 5
<212> TYPE: PRT
<213> ORGANISM: Artificial Sequence
<220> FEATURE:
<223> OTHER INFORMATION: m10 fragment

<400> SEQUENCE: 69

His Asn Ala Gly Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: m15 fragment

<400> SEQUENCE: 70

Ser Asn Ala Met Ala
1               5

<210> SEQ ID NO 71
<211> LENGTH: 5
<212> TYPE: PRT
<213> ORGANISM: Artificial Sequence
<220> FEATURE:
<223> OTHER INFORMATION: m23 fragment

<400> SEQUENCE: 71

Gln Asn Ala Val Ala
1               5

<210> SEQ ID NO 72
<211> LENGTH: 5
<212> TYPE: PRT
<213> ORGANISM: Artificial Sequence
<220> FEATURE:
```

<223> OTHER INFORMATION: m17 fragment

<400> SEQUENCE: 72

Tyr Asn Ala Tyr Met
1               5

<210> SEQ ID NO 73
<211> LENGTH: 5
<212> TYPE: PRT
<213> ORGANISM: Artificial Sequence
<220> FEATURE:
<223> OTHER INFORMATION: m12 fragment

<400> SEQUENCE: 73

Leu Asn Ala Trp Gly
1               5

<210> SEQ ID NO 74
<211> LENGTH: 5
<212> TYPE: PRT
<213> ORGANISM: Artificial Sequence
<220> FEATURE:
<223> OTHER INFORMATION: m20 fragment

<400> SEQUENCE: 74

His Asn Ala Ser Met
1               5

<210> SEQ ID NO 75
<211> LENGTH: 5
<212> TYPE: PRT
<213> ORGANISM: Artificial Sequence
<220> FEATURE:
<223> OTHER INFORMATION: m101 fragment

<400> SEQUENCE: 75

Tyr Asn Ala Phe Leu
1               5

<210> SEQ ID NO 76
<211> LENGTH: 5
<212> TYPE: PRT
<213> ORGANISM: Artificial Sequence
<220> FEATURE:
<223> OTHER INFORMATION: m106 fragment

<400> SEQUENCE: 76

Phe Asn Ala Phe Leu
1               5

<210> SEQ ID NO 77
<211> LENGTH: 5
<212> TYPE: PRT
<213> ORGANISM: Artificial Sequence
<220> FEATURE:
<223> OTHER INFORMATION: m111 fragment

<400> SEQUENCE: 77

Tyr Asn Ala Leu Trp
1               5

<210> SEQ ID NO 78
<211> LENGTH: 5
<212> TYPE: PRT
<213> ORGANISM: Artificial Sequence
<220> FEATURE:
<223> OTHER INFORMATION: m100 fragment

```
<400> SEQUENCE: 78

Phe Asn Ala Tyr Ile
1               5

<210> SEQ ID NO 79
<211> LENGTH: 5
<212> TYPE: PRT
<213> ORGANISM: Artificial Sequence
<220> FEATURE:
<223> OTHER INFORMATION: m110 fragment

<400> SEQUENCE: 79

Tyr Asn Ala Tyr Leu
1               5

<210> SEQ ID NO 80
<211> LENGTH: 5
<212> TYPE: PRT
<213> ORGANISM: Artificial Sequence
<220> FEATURE:
<223> OTHER INFORMATION: m104 fragment

<400> SEQUENCE: 80

Tyr Asn Ala Tyr Gln
1               5

<210> SEQ ID NO 81
<211> LENGTH: 5
<212> TYPE: PRT
<213> ORGANISM: Artificial Sequence
<220> FEATURE:
<223> OTHER INFORMATION: m108 fragment

<400> SEQUENCE: 81

Phe Asn Ala Ile Trp
1               5

<210> SEQ ID NO 82
<211> LENGTH: 5
<212> TYPE: PRT
<213> ORGANISM: Artificial Sequence
<220> FEATURE:
<223> OTHER INFORMATION: m207 fragment
<220> FEATURE:
<221> NAME/KEY: MISC_FEATURE
<222> LOCATION: (2)..(3)
<223> OTHER INFORMATION: amino acid deletion

<400> SEQUENCE: 82

Thr Xaa Xaa Trp Leu
1               5

<210> SEQ ID NO 83
<211> LENGTH: 5
<212> TYPE: PRT
<213> ORGANISM: Artificial Sequence
<220> FEATURE:
<223> OTHER INFORMATION: m212 fragment
<220> FEATURE:
<221> NAME/KEY: MISC_FEATURE
<222> LOCATION: (2)..(3)
<223> OTHER INFORMATION: amino acid deletion

<400> SEQUENCE: 83

His Xaa Xaa Trp Leu
1               5
```

```
<210> SEQ ID NO 84
<211> LENGTH: 5
<212> TYPE: PRT
<213> ORGANISM: Artificial Sequence
<220> FEATURE:
<223> OTHER INFORMATION: m202 fragment
<220> FEATURE:
<221> NAME/KEY: MISC_FEATURE
<222> LOCATION: (2)..(3)
<223> OTHER INFORMATION: amino acid deletion

<400> SEQUENCE: 84

Ile Xaa Xaa Trp Arg
1               5

<210> SEQ ID NO 85
<211> LENGTH: 5
<212> TYPE: PRT
<213> ORGANISM: Artificial Sequence
<220> FEATURE:
<223> OTHER INFORMATION: m204 fragment
<220> FEATURE:
<221> NAME/KEY: MISC_FEATURE
<222> LOCATION: (2)..(3)
<223> OTHER INFORMATION: amino acid deletion

<400> SEQUENCE: 85

His Xaa Xaa Trp Thr
1               5

<210> SEQ ID NO 86
<211> LENGTH: 5
<212> TYPE: PRT
<213> ORGANISM: Artificial Sequence
<220> FEATURE:
<223> OTHER INFORMATION: m206 fragment
<220> FEATURE:
<221> NAME/KEY: MISC_FEATURE
<222> LOCATION: (2)..(3)
<223> OTHER INFORMATION: amino acid deletion

<400> SEQUENCE: 86

Thr Xaa Xaa Trp Arg
1               5

<210> SEQ ID NO 87
<211> LENGTH: 5
<212> TYPE: PRT
<213> ORGANISM: Artificial Sequence
<220> FEATURE:
<223> OTHER INFORMATION: m208 fragment
<220> FEATURE:
<221> NAME/KEY: MISC_FEATURE
<222> LOCATION: (2)..(3)
<223> OTHER INFORMATION: amino acid deletion

<400> SEQUENCE: 87

Ala Xaa Xaa Trp Arg
1               5

<210> SEQ ID NO 88
<211> LENGTH: 5
<212> TYPE: PRT
<213> ORGANISM: Artificial Sequence
<220> FEATURE:
<223> OTHER INFORMATION: m203 fragment
<220> FEATURE:
<221> NAME/KEY: MISC_FEATURE
<222> LOCATION: (2)..(3)
<223> OTHER INFORMATION: amino acid deletion
```

```
<400> SEQUENCE: 88

Arg Xaa Xaa Trp Ser
1               5

<210> SEQ ID NO 89
<211> LENGTH: 5
<212> TYPE: PRT
<213> ORGANISM: Artificial Sequence
<220> FEATURE:
<223> OTHER INFORMATION: m209 fragment
<220> FEATURE:
<221> NAME/KEY: MISC_FEATURE
<222> LOCATION: (2)..(3)
<223> OTHER INFORMATION: amino acid deletion

<400> SEQUENCE: 89

Asn Xaa Xaa Trp Arg
1               5

<210> SEQ ID NO 90
<211> LENGTH: 5
<212> TYPE: PRT
<213> ORGANISM: Artificial Sequence
<220> FEATURE:
<223> OTHER INFORMATION: m200 fragment
<220> FEATURE:
<221> NAME/KEY: MISC_FEATURE
<222> LOCATION: (2)..(3)
<223> OTHER INFORMATION: amino acid deletion

<400> SEQUENCE: 90

Lys Xaa Xaa Trp Ser
1               5

<210> SEQ ID NO 91
<211> LENGTH: 5
<212> TYPE: PRT
<213> ORGANISM: Artificial Sequence
<220> FEATURE:
<223> OTHER INFORMATION: m201 fragment
<220> FEATURE:
<221> NAME/KEY: MISC_FEATURE
<222> LOCATION: (2)..(3)
<223> OTHER INFORMATION: amino acid deletion

<400> SEQUENCE: 91

Ser Xaa Xaa Val Phe
1               5

<210> SEQ ID NO 92
<211> LENGTH: 5
<212> TYPE: PRT
<213> ORGANISM: Artificial Sequence
<220> FEATURE:
<223> OTHER INFORMATION: m211 fragment
<220> FEATURE:
<221> NAME/KEY: MISC_FEATURE
<222> LOCATION: (2)..(3)
<223> OTHER INFORMATION: amino acid deletion

<400> SEQUENCE: 92

Lys Xaa Xaa Trp Thr
1               5

<210> SEQ ID NO 93
<211> LENGTH: 5
<212> TYPE: PRT
<213> ORGANISM: Artificial Sequence
```

```
<220> FEATURE:
<223> OTHER INFORMATION: m300 fragment
<220> FEATURE:
<221> NAME/KEY: MISC_FEATURE
<222> LOCATION: (2)..(3)
<223> OTHER INFORMATION: amino acid deletion

<400> SEQUENCE: 93

Ala Xaa Xaa Trp Tyr
1               5

<210> SEQ ID NO 94
<211> LENGTH: 5
<212> TYPE: PRT
<213> ORGANISM: Artificial Sequence
<220> FEATURE:
<223> OTHER INFORMATION: m301 fragment
<220> FEATURE:
<221> NAME/KEY: MISC_FEATURE
<222> LOCATION: (2)..(3)
<223> OTHER INFORMATION: amino acid deletion

<400> SEQUENCE: 94

His Xaa Xaa Trp Met
1               5

<210> SEQ ID NO 95
<211> LENGTH: 5
<212> TYPE: PRT
<213> ORGANISM: Artificial Sequence
<220> FEATURE:
<223> OTHER INFORMATION: m302 fragment
<220> FEATURE:
<221> NAME/KEY: MISC_FEATURE
<222> LOCATION: (2)..(3)
<223> OTHER INFORMATION: amino acid deletion

<400> SEQUENCE: 95

His Xaa Xaa Trp Tyr
1               5

<210> SEQ ID NO 96
<211> LENGTH: 5
<212> TYPE: PRT
<213> ORGANISM: Artificial Sequence
<220> FEATURE:
<223> OTHER INFORMATION: m303 fragment
<220> FEATURE:
<221> NAME/KEY: MISC_FEATURE
<222> LOCATION: (2)..(3)
<223> OTHER INFORMATION: amino acid deletion

<400> SEQUENCE: 96

Glu Xaa Xaa Trp Tyr
1               5

<210> SEQ ID NO 97
<211> LENGTH: 5
<212> TYPE: PRT
<213> ORGANISM: Artificial Sequence
<220> FEATURE:
<223> OTHER INFORMATION: m304 fragment
<220> FEATURE:
<221> NAME/KEY: MISC_FEATURE
<222> LOCATION: (2)..(3)
<223> OTHER INFORMATION: amino acid deletion

<400> SEQUENCE: 97

Gln Xaa Xaa Trp Tyr
1               5
```

```
<210> SEQ ID NO 98
<211> LENGTH: 4
<212> TYPE: PRT
<213> ORGANISM: Artificial Sequence
<220> FEATURE:
<223> OTHER INFORMATION: streptavidin mutein

<400> SEQUENCE: 98

Val Thr Ala Arg
1

<210> SEQ ID NO 99
<211> LENGTH: 4
<212> TYPE: PRT
<213> ORGANISM: Artificial Sequence
<220> FEATURE:
<223> OTHER INFORMATION: streptavidin mutein

<400> SEQUENCE: 99

Ile Gly Ala Arg
1

<210> SEQ ID NO 100
<211> LENGTH: 8
<212> TYPE: PRT
<213> ORGANISM: Artificial Sequence
<220> FEATURE:
<223> OTHER INFORMATION: Strep-tagII affinity peptide ligand

<400> SEQUENCE: 100

Trp Ser His Pro Gln Phe Glu Lys
1               5

<210> SEQ ID NO 101
<211> LENGTH: 8
<212> TYPE: PRT
<213> ORGANISM: Artificial Sequence
<220> FEATURE:
<223> OTHER INFORMATION: peptide sequence
<220> FEATURE:
<221> NAME/KEY: MISC_FEATURE
<222> LOCATION: (2)..(2)
<223> OTHER INFORMATION: Xaa is an arbitrary amino acid
<220> FEATURE:
<221> NAME/KEY: MISC_FEATURE
<222> LOCATION: (7)..(8)
<223> OTHER INFORMATION: Xaa is Gly
<220> FEATURE:
<221> NAME/KEY: MISC_FEATURE
<222> LOCATION: (7)..(7)
<223> OTHER INFORMATION: Xaa is Glu
<220> FEATURE:
<221> NAME/KEY: MISC_FEATURE
<222> LOCATION: (8)..(8)
<223> OTHER INFORMATION: Xaa is Arg or Lys

<400> SEQUENCE: 101

Trp Xaa His Pro Gln Phe Xaa Xaa
1               5

<210> SEQ ID NO 102
<211> LENGTH: 8
<212> TYPE: PRT
<213> ORGANISM: Artificial Sequence
<220> FEATURE:
<223> OTHER INFORMATION: Strep-tag streptavidin binding peptide

<400> SEQUENCE: 102
```

Trp Arg His Pro Gln Phe Gly Gly
1               5

<210> SEQ ID NO 103
<211> LENGTH: 28
<212> TYPE: PRT
<213> ORGANISM: Artificial Sequence
<220> FEATURE:
<223> OTHER INFORMATION: peptide sequence

<400> SEQUENCE: 103

Trp Ser His Pro Gln Phe Glu Lys Gly Gly Ser Gly Gly Ser
1               5                   10                  15

Gly Gly Gly Ser Trp Ser His Pro Gln Phe Glu Lys
            20                  25

<210> SEQ ID NO 104
<211> LENGTH: 248
<212> TYPE: PRT
<213> ORGANISM: Artificial Sequence
<220> FEATURE:
<223> OTHER INFORMATION: GFP-StrepII

<400> SEQUENCE: 104

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Gln Ser Ala
225                 230                 235                 240

Trp Ser His Pro Gln Phe Glu Lys
                245

<210> SEQ ID NO 105

```
<211> LENGTH: 268
<212> TYPE: PRT
<213> ORGANISM: Artificial Sequence
<220> FEATURE:
<223> OTHER INFORMATION: GFP-di-tag3

<400> SEQUENCE: 105
```

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Gln Ser Ala
225                 230                 235                 240

Trp Ser His Pro Gln Phe Glu Lys Gly Gly Gly Ser Gly Gly Gly Ser
                245                 250                 255

Gly Gly Gly Ser Trp Ser His Pro Gln Phe Glu Lys
            260                 265

```
<210> SEQ ID NO 106
<211> LENGTH: 118
<212> TYPE: PRT
<213> ORGANISM: Artificial Sequence
<220> FEATURE:
<223> OTHER INFORMATION: Cytb562-StrepII

<400> SEQUENCE: 106
```

Ala Asp Leu Glu Asp Asn Met Glu Thr Leu Asn Asp Asn Leu Lys Val
1               5                   10                  15

Ile Glu Lys Ala Asp Asn Ala Ala Gln Val Lys Asp Ala Leu Thr Lys
            20                  25                  30

Met Arg Ala Ala Ala Leu Asp Ala Gln Lys Ala Thr Pro Pro Lys Leu
        35                  40                  45

Glu Asp Lys Ser Pro Asp Ser Pro Glu Met Lys Asp Phe Arg His Gly

```
                50                  55                  60
Phe Asp Ile Leu Val Gly Gln Ile Asp Asp Ala Leu Lys Leu Ala Asn
 65                  70                  75                  80

Glu Gly Lys Val Lys Glu Ala Gln Ala Ala Glu Gln Leu Lys Thr
                 85                  90                  95

Thr Arg Asn Ala Tyr His Gln Lys Tyr Arg Pro Pro Ser Ala Trp Ser
                100                 105                 110

His Pro Gln Phe Glu Lys
        115

<210> SEQ ID NO 107
<211> LENGTH: 139
<212> TYPE: PRT
<213> ORGANISM: Artificial Sequence
<220> FEATURE:
<223> OTHER INFORMATION: Cytb562-di-tag3

<400> SEQUENCE: 107

Ala Asp Leu Glu Asp Asn Met Glu Thr Leu Asn Asp Asn Leu Lys Val
 1               5                  10                  15

Ile Glu Lys Ala Asp Asn Ala Ala Gln Val Lys Asp Ala Leu Thr Lys
                20                  25                  30

Met Arg Ala Ala Ala Leu Asp Ala Gln Lys Ala Thr Pro Pro Lys Leu
                35                  40                  45

Glu Asp Lys Ser Pro Asp Ser Pro Glu Met Lys Asp Phe Arg His Gly
 50                  55                  60

Phe Asp Ile Leu Val Gly Gln Ile Asp Asp Ala Leu Lys Leu Ala Asn
 65                  70                  75                  80

Glu Gly Lys Val Lys Glu Ala Gln Ala Ala Glu Gln Leu Lys Thr
                 85                  90                  95

Thr Arg Asn Ala Tyr His Gln Lys Tyr Arg Pro Pro Ser Ala Trp Ser
                100                 105                 110

His Pro Gln Phe Glu Lys Gly Gly Gly Ser Gly Gly Ser Gly
        115                 120                 125

Gly Gly Ser Trp Ser His Pro Gln Phe Glu Lys
        130                 135

<210> SEQ ID NO 108
<211> LENGTH: 8
<212> TYPE: PRT
<213> ORGANISM: Artificial Sequence
<220> FEATURE:
<223> OTHER INFORMATION: peptide sequence
<220> FEATURE:
<221> NAME/KEY: MISC_FEATURE
<222> LOCATION: (1)..(1)
<223> OTHER INFORMATION: Xaa is Trp, Lys or Arg
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (7)..(8)
<223> OTHER INFORMATION: Xaa is Gly
<220> FEATURE:
<221> NAME/KEY: MISC_FEATURE
<222> LOCATION: (7)..(7)
<223> OTHER INFORMATION: Xaa is Glu
<220> FEATURE:
<221> NAME/KEY: MISC_FEATURE
<222> LOCATION: (8)..(8)
<223> OTHER INFORMATION: Xaa is Lys or Arg
```

<400> SEQUENCE: 108

Xaa Xaa His Pro Gln Phe Xaa Xaa
1               5

<210> SEQ ID NO 109
<211> LENGTH: 24
<212> TYPE: PRT
<213> ORGANISM: Artificial Sequence
<220> FEATURE:
<223> OTHER INFORMATION: di-tag2

<400> SEQUENCE: 109

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 110
<211> LENGTH: 28
<212> TYPE: PRT
<213> ORGANISM: Artificial Sequence
<220> FEATURE:
<223> OTHER INFORMATION: peptide sequence

<400> SEQUENCE: 110

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 111
<211> LENGTH: 126
<212> TYPE: PRT
<213> ORGANISM: Artificial Sequence
<220> FEATURE:
<223> OTHER INFORMATION: wild type

<400> SEQUENCE: 111

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 112
<211> LENGTH: 126
<212> TYPE: PRT
<213> ORGANISM: Artificial Sequence
<220> FEATURE:
<223> OTHER INFORMATION: mutein 1

<400> SEQUENCE: 112

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 113
<211> LENGTH: 126
<212> TYPE: PRT
<213> ORGANISM: Artificial Sequence
<220> FEATURE:
<223> OTHER INFORMATION: mutein 2

<400> SEQUENCE: 113

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 114
<211> LENGTH: 126
<212> TYPE: PRT
<213> ORGANISM: Artificial Sequence
<220> FEATURE:
<223> OTHER INFORMATION: mutein m400

<400> SEQUENCE: 114

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Gly Cys
            20                  25                  30

Ala Arg Gly Asn Ala Glu Cys Arg Tyr Val Leu Thr Gly Arg Tyr Asp
        35                  40                  45

```
Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
                100                 105                 110

Gly His Asp Thr Phe Thr Lys Val Lys Pro Ser Ala Ala Ser
                115                 120                 125
```

<210> SEQ ID NO 115
<211> LENGTH: 126
<212> TYPE: PRT
<213> ORGANISM: Artificial Sequence
<220> FEATURE:
<223> OTHER INFORMATION: mutein m402

<400> SEQUENCE: 115

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
                20                  25                  30

Ala Arg Gly Asn Ala Glu Cys Arg Tyr Val Leu Thr Gly Arg Tyr Asp
                35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
                100                 105                 110

Gly His Asp Thr Phe Thr Lys Val Lys Pro Ser Ala Ala Ser
                115                 120                 125
```

<210> SEQ ID NO 116
<211> LENGTH: 126
<212> TYPE: PRT
<213> ORGANISM: Artificial Sequence
<220> FEATURE:
<223> OTHER INFORMATION: mutein m4001

<400> SEQUENCE: 116

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
                20                  25                  30

Gly Arg Gly Asn Ala Glu Cys Arg Tyr Val Leu Thr Gly Arg Tyr Asp
                35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
                100                 105                 110
```

```
Gly His Asp Thr Phe Thr Lys Val Lys Pro Ser Ala Ala Ser
        115                 120                 125
```

<210> SEQ ID NO 117
<211> LENGTH: 126
<212> TYPE: PRT
<213> ORGANISM: Artificial Sequence
<220> FEATURE:
<223> OTHER INFORMATION: mutein m36

<400> SEQUENCE: 117

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Phe Met Ser Thr Leu Val
            100                 105                 110

Gly His Asp Thr Phe Thr Lys Val Lys Pro Ser Ala Ala Ser
        115                 120                 125
```

<210> SEQ ID NO 118
<211> LENGTH: 126
<212> TYPE: PRT
<213> ORGANISM: Artificial Sequence
<220> FEATURE:
<223> OTHER INFORMATION: mutein m23

<400> SEQUENCE: 118

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Tyr Ala Ser Thr Leu Val
            100                 105                 110

Gly His Asp Thr Phe Thr Lys Val Lys Pro Ser Ala Ala Ser
        115                 120                 125
```

<210> SEQ ID NO 119
<211> LENGTH: 124
<212> TYPE: PRT
<213> ORGANISM: Artificial Sequence
<220> FEATURE:
<223> OTHER INFORMATION: mutein m41

```
<400> SEQUENCE: 119

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Trp Tyr Ser Thr Leu Val Gly His
            100                 105                 110

Asp Thr Phe Thr Lys Val Lys Pro Ser Ala Ala Ser
        115                 120

<210> SEQ ID NO 120
<211> LENGTH: 126
<212> TYPE: PRT
<213> ORGANISM: Artificial Sequence
<220> FEATURE:
<223> OTHER INFORMATION: mutein m4

<400> SEQUENCE: 120

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Asp Asn Ala Gly Phe Ser Thr Leu Val
            100                 105                 110

Gly His Asp Thr Phe Thr Lys Val Lys Pro Ser Ala Ala Ser
        115                 120                 125

<210> SEQ ID NO 121
<211> LENGTH: 126
<212> TYPE: PRT
<213> ORGANISM: Artificial Sequence
<220> FEATURE:
<223> OTHER INFORMATION: mutein 1 m12

<400> SEQUENCE: 121

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45
```

```
Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Arg Asn Ala Gly Phe Ser Thr Leu Val
                100                 105                 110

Gly His Asp Thr Phe Thr Lys Val Lys Pro Ser Ala Ala Ser
                115                 120                 125

<210> SEQ ID NO 122
<211> LENGTH: 126
<212> TYPE: PRT
<213> ORGANISM: Artificial Sequence
<220> FEATURE:
<223> OTHER INFORMATION: mutein 1 m22

<400> SEQUENCE: 122

Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
                 35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Gln Asn Ala Gly Phe Ser Thr Leu Val
                100                 105                 110

Gly His Asp Thr Phe Thr Lys Val Lys Pro Ser Ala Ala Ser
                115                 120                 125

<210> SEQ ID NO 123
<211> LENGTH: 126
<212> TYPE: PRT
<213> ORGANISM: Artificial Sequence
<220> FEATURE:
<223> OTHER INFORMATION: mutein 1 m31

<400> SEQUENCE: 123

Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
                 35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Phe Asn Ala Ser Trp Ser Thr Leu Val
```

100                 105                 110

Gly His Asp Thr Phe Thr Lys Val Lys Pro Ser Ala Ala Ser
            115                 120                 125

<210> SEQ ID NO 124
<211> LENGTH: 126
<212> TYPE: PRT
<213> ORGANISM: Artificial Sequence
<220> FEATURE:
<223> OTHER INFORMATION: mutein 1 m

<400> SEQUENCE: 124

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Asp Asn Ala Val Met Ser Thr Leu Val
            100                 105                 110

Gly His Asp Thr Phe Thr Lys Val Lys Pro Ser Ala Ala Ser
        115                 120                 125

<210> SEQ ID NO 125
<211> LENGTH: 124
<212> TYPE: PRT
<213> ORGANISM: Artificial Sequence
<220> FEATURE:
<223> OTHER INFORMATION: mutein 1 m35

<400> SEQUENCE: 125

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Trp Met Ser Thr Leu Val Gly His
            100                 105                 110

Asp Thr Phe Thr Lys Val Lys Pro Ser Ala Ala Ser
        115                 120

<210> SEQ ID NO 126
<211> LENGTH: 126
<212> TYPE: PRT
<213> ORGANISM: Artificial Sequence
<220> FEATURE:

<223> OTHER INFORMATION: mutein 1 m38

<400> SEQUENCE: 126

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Phe Ser Thr Leu Val
            100                 105                 110

Gly His Asp Thr Phe Thr Lys Val Lys Pro Ser Ala Ala Ser
        115                 120                 125

<210> SEQ ID NO 127
<211> LENGTH: 126
<212> TYPE: PRT
<213> ORGANISM: Artificial Sequence
<220> FEATURE:
<223> OTHER INFORMATION: mutein 1 m40

<400> SEQUENCE: 127

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Tyr Ser Ser Thr Leu Val
            100                 105                 110

Gly His Asp Thr Phe Thr Lys Val Lys Pro Ser Ala Ala Ser
        115                 120                 125

<210> SEQ ID NO 128
<211> LENGTH: 126
<212> TYPE: PRT
<213> ORGANISM: Artificial Sequence
<220> FEATURE:
<223> OTHER INFORMATION: mutein 1 m42

<400> SEQUENCE: 128

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp

```
                35                  40                  45
Ser Ala Pro Ala Thr Asp Gly Ser Gly Thr Ala Leu Gly Trp Thr Val
 50                  55                  60
Ala Trp Lys Asn Asn Tyr Arg Asn Ala His Ser Ala Thr Thr Trp Ser
 65                  70                  75                  80
Gly Gln Tyr Val Gly Gly Ala Glu Ala Arg Ile Asn Thr Gln Trp Leu
                 85                  90                  95
Leu Thr Ser Gly Thr Thr Glu Phe Asn Ala Tyr Gly Ser Thr Leu Val
                100                 105                 110
Gly His Asp Thr Phe Thr Lys Val Lys Pro Ser Ala Ala Ser
                115                 120                 125

<210> SEQ ID NO 129
<211> LENGTH: 126
<212> TYPE: PRT
<213> ORGANISM: Artificial Sequence
<220> FEATURE:
<223> OTHER INFORMATION: mutein 1 m45

<400> SEQUENCE: 129

Glu Ala Gly Ile Thr Gly Thr Trp Tyr Asn Gln Leu Gly Ser Thr Phe
 1                   5                  10                  15
Ile Val Thr Ala Gly Ala Asp Gly Ala Leu Thr Gly Thr Tyr Val Thr
                 20                  25                  30
Ala Arg Gly Asn Ala Glu Ser Arg Tyr Val Leu Thr Gly Arg Tyr Asp
                 35                  40                  45
Ser Ala Pro Ala Thr Asp Gly Ser Gly Thr Ala Leu Gly Trp Thr Val
 50                  55                  60
Ala Trp Lys Asn Asn Tyr Arg Asn Ala His Ser Ala Thr Thr Trp Ser
 65                  70                  75                  80
Gly Gln Tyr Val Gly Gly Ala Glu Ala Arg Ile Asn Thr Gln Trp Leu
                 85                  90                  95
Leu Thr Ser Gly Thr Thr Glu Tyr Asn Ala Gly Phe Ser Thr Leu Val
                100                 105                 110
Gly His Asp Thr Phe Thr Lys Val Lys Pro Ser Ala Ala Ser
                115                 120                 125

<210> SEQ ID NO 130
<211> LENGTH: 126
<212> TYPE: PRT
<213> ORGANISM: Artificial Sequence
<220> FEATURE:
<223> OTHER INFORMATION: mutein 1 m46

<400> SEQUENCE: 130

Glu Ala Gly Ile Thr Gly Thr Trp Tyr Asn Gln Leu Gly Ser Thr Phe
 1                   5                  10                  15
Ile Val Thr Ala Gly Ala Asp Gly Ala Leu Thr Gly Thr Tyr Val Thr
                 20                  25                  30
Ala Arg Gly Asn Ala Glu Ser Arg Tyr Val Leu Thr Gly Arg Tyr Asp
                 35                  40                  45
Ser Ala Pro Ala Thr Asp Gly Ser Gly Thr Ala Leu Gly Trp Thr Val
 50                  55                  60
Ala Trp Lys Asn Asn Tyr Arg Asn Ala His Ser Ala Thr Thr Trp Ser
 65                  70                  75                  80
Gly Gln Tyr Val Gly Gly Ala Glu Ala Arg Ile Asn Thr Gln Trp Leu
                 85                  90                  95
```

Leu Thr Ser Gly Thr Thr Glu Arg Asn Ala Tyr Ala Ser Thr Leu Val
            100                 105                 110

Gly His Asp Thr Phe Thr Lys Val Lys Pro Ser Ala Ala Ser
            115                 120                 125

<210> SEQ ID NO 131
<211> LENGTH: 126
<212> TYPE: PRT
<213> ORGANISM: Artificial Sequence
<220> FEATURE:
<223> OTHER INFORMATION: mutein 1 m47

<400> SEQUENCE: 131

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
            50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Trp Asn Ala Tyr Gly Ser Thr Leu Val
            100                 105                 110

Gly His Asp Thr Phe Thr Lys Val Lys Pro Ser Ala Ala Ser
            115                 120                 125

<210> SEQ ID NO 132
<211> LENGTH: 126
<212> TYPE: PRT
<213> ORGANISM: Artificial Sequence
<220> FEATURE:
<223> OTHER INFORMATION: mutein 1 m7

<400> SEQUENCE: 132

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
            50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Leu Asn Ala Gly Phe Ser Thr Leu Val
            100                 105                 110

Gly His Asp Thr Phe Thr Lys Val Lys Pro Ser Ala Ala Ser
            115                 120                 125

<210> SEQ ID NO 133
<211> LENGTH: 126
<212> TYPE: PRT
<213> ORGANISM: Artificial Sequence
<220> FEATURE:
<223> OTHER INFORMATION: mutein 1 m10

<400> SEQUENCE: 133

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Asn Ala Gly Tyr Ser Thr Leu Val
            100                 105                 110

Gly His Asp Thr Phe Thr Lys Val Lys Pro Ser Ala Ala Ser
        115                 120                 125

<210> SEQ ID NO 134
<211> LENGTH: 126
<212> TYPE: PRT
<213> ORGANISM: Artificial Sequence
<220> FEATURE:
<223> OTHER INFORMATION: mutein 1 m17

<400> SEQUENCE: 134

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Met Asn Ala Gly Phe Ser Thr Leu Val
            100                 105                 110

Gly His Asp Thr Phe Thr Lys Val Lys Pro Ser Ala Ala Ser
        115                 120                 125

<210> SEQ ID NO 135
<211> LENGTH: 126
<212> TYPE: PRT
<213> ORGANISM: Artificial Sequence
<220> FEATURE:
<223> OTHER INFORMATION: mutein 1 m21

<400> SEQUENCE: 135

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

```
Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Arg Asn Ala Gly Tyr Ser Thr Leu Val
            100                 105                 110

Gly His Asp Thr Phe Thr Lys Val Lys Pro Ser Ala Ala Ser
            115                 120                 125
```

<210> SEQ ID NO 136
<211> LENGTH: 126
<212> TYPE: PRT
<213> ORGANISM: Artificial Sequence
<220> FEATURE:
<223> OTHER INFORMATION: mutein 1 m24

<400> SEQUENCE: 136

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Trp Ser Thr Leu Val
            100                 105                 110

Gly His Asp Thr Phe Thr Lys Val Lys Pro Ser Ala Ala Ser
            115                 120                 125
```

<210> SEQ ID NO 137
<211> LENGTH: 126
<212> TYPE: PRT
<213> ORGANISM: Artificial Sequence
<220> FEATURE:
<223> OTHER INFORMATION: mutein 1 m27

<400> SEQUENCE: 137

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                85                  90                  95
```

```
Leu Thr Ser Gly Thr Thr Glu His Asn Ala Gly Phe Ser Thr Leu Val
            100                 105                 110

Gly His Asp Thr Phe Thr Lys Val Lys Pro Ser Ala Ala Ser
            115                 120                 125

<210> SEQ ID NO 138
<211> LENGTH: 126
<212> TYPE: PRT
<213> ORGANISM: Artificial Sequence
<220> FEATURE:
<223> OTHER INFORMATION: mutein 1 m28

<400> SEQUENCE: 138

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ser Asn Ala Gly Phe Ser Thr Leu Val
            100                 105                 110

Gly His Asp Thr Phe Thr Lys Val Lys Pro Ser Ala Ala Ser
            115                 120                 125

<210> SEQ ID NO 139
<211> LENGTH: 126
<212> TYPE: PRT
<213> ORGANISM: Artificial Sequence
<220> FEATURE:
<223> OTHER INFORMATION: mutein 1 m30

<400> SEQUENCE: 139

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Thr Asn Ala Gly Phe Ser Thr Leu Val
            100                 105                 110

Gly His Asp Thr Phe Thr Lys Val Lys Pro Ser Ala Ala Ser
            115                 120                 125

<210> SEQ ID NO 140
<211> LENGTH: 126
<212> TYPE: PRT
```

<210> SEQ ID NO 140
<211> LENGTH: 126
<212> TYPE: PRT
<213> ORGANISM: Artificial Sequence
<220> FEATURE:
<223> OTHER INFORMATION: mutein 1 m33

<400> SEQUENCE: 140

```
Glu Ala Gly Ile Thr Gly Thr Trp Tyr Asn Gln Leu Gly Ser Thr Phe
1               5                   10                  15
Ile Val Thr Ala Gly Ala Asp Gly Ala Leu Thr Gly Thr Tyr Val Thr
            20                  25                  30
Ala Arg Gly Asn Ala Glu Ser Arg Tyr Val Leu Thr Gly Arg Tyr Asp
        35                  40                  45
Ser Ala Pro Ala Thr Asp Gly Ser Gly Thr Ala Leu Gly Trp Thr Val
    50                  55                  60
Ala Trp Lys Asn Asn Tyr Arg Asn Ala His Ser Ala Thr Thr Trp Ser
65                  70                  75                  80
Gly Gln Tyr Val Gly Gly Ala Glu Ala Arg Ile Asn Thr Gln Trp Leu
                85                  90                  95
Leu Thr Ser Gly Thr Thr Glu Asn Ala Gly Phe Ser Thr Leu Val
            100                 105                 110
Gly His Asp Thr Phe Thr Lys Val Lys Pro Ser Ala Ala Ser
        115                 120                 125
```

<210> SEQ ID NO 141
<211> LENGTH: 126
<212> TYPE: PRT
<213> ORGANISM: Artificial Sequence
<220> FEATURE:
<223> OTHER INFORMATION: mutein 1 m1

<400> SEQUENCE: 141

```
Glu Ala Gly Ile Thr Gly Thr Trp Tyr Asn Gln Leu Gly Ser Thr Phe
1               5                   10                  15
Ile Val Thr Ala Gly Ala Asp Gly Ala Leu Thr Gly Thr Tyr Val Thr
            20                  25                  30
Ala Arg Gly Asn Ala Glu Ser Arg Tyr Val Leu Thr Gly Arg Tyr Asp
        35                  40                  45
Ser Ala Pro Ala Thr Asp Gly Ser Gly Thr Ala Leu Gly Trp Thr Val
    50                  55                  60
Ala Trp Lys Asn Asn Tyr Arg Asn Ala His Ser Ala Thr Thr Trp Ser
65                  70                  75                  80
Gly Gln Tyr Val Gly Gly Ala Glu Ala Arg Ile Asn Thr Gln Trp Leu
                85                  90                  95
Leu Thr Ser Gly Thr Thr Glu Asn Ala Gly Met Ser Thr Leu Val
            100                 105                 110
Gly His Asp Thr Phe Thr Lys Val Lys Pro Ser Ala Ala Ser
        115                 120                 125
```

<210> SEQ ID NO 142
<211> LENGTH: 126
<212> TYPE: PRT
<213> ORGANISM: Artificial Sequence
<220> FEATURE:
<223> OTHER INFORMATION: mutein 1 m3

<400> SEQUENCE: 142

```
Glu Ala Gly Ile Thr Gly Thr Trp Tyr Asn Gln Leu Gly Ser Thr Phe
1               5                   10                  15
Ile Val Thr Ala Gly Ala Asp Gly Ala Leu Thr Gly Thr Tyr Val Thr
            20                  25                  30
```

```
Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Trp Asn Ala Cys Cys Ser Thr Leu Val
            100                 105                 110

Gly His Asp Thr Phe Thr Lys Val Lys Pro Ser Ala Ala Ser
        115                 120                 125

<210> SEQ ID NO 143
<211> LENGTH: 126
<212> TYPE: PRT
<213> ORGANISM: Artificial Sequence
<220> FEATURE:
<223> OTHER INFORMATION: mutein 1 m8

<400> SEQUENCE: 143

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Met Asn Ala Phe Val Ser Thr Leu Val
            100                 105                 110

Gly His Asp Thr Phe Thr Lys Val Lys Pro Ser Ala Ala Ser
        115                 120                 125

<210> SEQ ID NO 144
<211> LENGTH: 126
<212> TYPE: PRT
<213> ORGANISM: Artificial Sequence
<220> FEATURE:
<223> OTHER INFORMATION: mutein 1 m15

<400> SEQUENCE: 144

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
```

```
                85                  90                  95
Leu Thr Ser Gly Thr Thr Glu Ala Asn Ala Asp Trp Ser Thr Leu Val
                100                 105                 110

Gly His Asp Thr Phe Thr Lys Val Lys Pro Ser Ala Ala Ser
            115                 120                 125

<210> SEQ ID NO 145
<211> LENGTH: 126
<212> TYPE: PRT
<213> ORGANISM: Artificial Sequence
<220> FEATURE:
<223> OTHER INFORMATION: mutein 1 m6

<400> SEQUENCE: 145

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ser Asn Ala Met Met Ser Thr Leu Val
                100                 105                 110

Gly His Asp Thr Phe Thr Lys Val Lys Pro Ser Ala Ala Ser
            115                 120                 125

<210> SEQ ID NO 146
<211> LENGTH: 126
<212> TYPE: PRT
<213> ORGANISM: Artificial Sequence
<220> FEATURE:
<223> OTHER INFORMATION: mutein 1 m9

<400> SEQUENCE: 146

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Arg Asn Ala Val Val Ser Thr Leu Val
                100                 105                 110

Gly His Asp Thr Phe Thr Lys Val Lys Pro Ser Ala Ala Ser
            115                 120                 125

<210> SEQ ID NO 147
<211> LENGTH: 126
```

-continued

```
<212> TYPE: PRT
<213> ORGANISM: Artificial Sequence
<220> FEATURE:
<223> OTHER INFORMATION: mutein 1 m20

<400> SEQUENCE: 147

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ser Asn Ala Ser Phe Ser Thr Leu Val
                100                 105                 110

Gly His Asp Thr Phe Thr Lys Val Lys Pro Ser Ala Ala Ser
            115                 120                 125

<210> SEQ ID NO 148
<211> LENGTH: 124
<212> TYPE: PRT
<213> ORGANISM: Artificial Sequence
<220> FEATURE:
<223> OTHER INFORMATION: mutein 1 m34

<400> SEQUENCE: 148

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Trp Asp Ser Thr Leu Val Gly His
                100                 105                 110

Asp Thr Phe Thr Lys Val Lys Pro Ser Ala Ala Ser
            115                 120

<210> SEQ ID NO 149
<211> LENGTH: 126
<212> TYPE: PRT
<213> ORGANISM: Artificial Sequence
<220> FEATURE:
<223> OTHER INFORMATION: mutein 1 m14

<400> SEQUENCE: 149

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
```

```
                 20                  25                  30

Ala Arg Gly Asn Ala Glu Ser Arg Tyr Val Leu Thr Gly Arg Tyr Asp
             35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Arg Asn Ala Arg Ala Ser Thr Leu Val
            100                 105                 110

Gly His Asp Thr Phe Thr Lys Val Lys Pro Ser Ala Ala Ser
            115                 120                 125
```

<210> SEQ ID NO 150
<211> LENGTH: 126
<212> TYPE: PRT
<213> ORGANISM: Artificial Sequence
<220> FEATURE:
<223> OTHER INFORMATION: mutein 1 m18

<400> SEQUENCE: 150

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
             35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ser Asn Ala Ala Phe Ser Thr Leu Val
            100                 105                 110

Gly His Asp Thr Phe Thr Lys Val Lys Pro Ser Ala Ala Ser
            115                 120                 125
```

<210> SEQ ID NO 151
<211> LENGTH: 126
<212> TYPE: PRT
<213> ORGANISM: Artificial Sequence
<220> FEATURE:
<223> OTHER INFORMATION: mutein m19

<400> SEQUENCE: 151

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
             35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
 65                  70                  75                  80
```

Gly Gln Tyr Val Gly Gly Ala Glu Ala Arg Ile Asn Thr Gln Trp Leu
            85                  90                  95

Leu Thr Ser Gly Thr Thr Glu Gly Asn Ala Met Met Ser Thr Leu Val
            100                 105                 110

Gly His Asp Thr Phe Thr Lys Val Lys Pro Ser Ala Ala Ser
            115                 120             125

<210> SEQ ID NO 152
<211> LENGTH: 126
<212> TYPE: PRT
<213> ORGANISM: Artificial Sequence
<220> FEATURE:
<223> OTHER INFORMATION: m4001-m8

<400> SEQUENCE: 152

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Gly Asn Ala Gly Phe Ser Thr Leu Val
            100                 105                 110

Gly His Asp Thr Phe Thr Lys Val Lys Pro Ser Ala Ala Ser
            115                 120             125

<210> SEQ ID NO 153
<211> LENGTH: 126
<212> TYPE: PRT
<213> ORGANISM: Artificial Sequence
<220> FEATURE:
<223> OTHER INFORMATION: m4001-m21

<400> SEQUENCE: 153

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Asp Asn Ala Gly Tyr Ser Thr Leu Val
            100                 105                 110

Gly His Asp Thr Phe Thr Lys Val Lys Pro Ser Ala Ala Ser
            115                 120             125

<210> SEQ ID NO 154

<211> LENGTH: 126
<212> TYPE: PRT
<213> ORGANISM: Artificial Sequence
<220> FEATURE:
<223> OTHER INFORMATION: m4001-m9

<400> SEQUENCE: 154

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
        115                 120                 125
```

<210> SEQ ID NO 155
<211> LENGTH: 126
<212> TYPE: PRT
<213> ORGANISM: Artificial Sequence
<220> FEATURE:
<223> OTHER INFORMATION: m4001-m1

<400> SEQUENCE: 155

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Arg Asn Ala Met Met Ser Thr Leu Val
            100                 105                 110

Gly His Asp Thr Phe Thr Lys Val Lys Pro Ser Ala Ala Ser
        115                 120                 125
```

<210> SEQ ID NO 156
<211> LENGTH: 126
<212> TYPE: PRT
<213> ORGANISM: Artificial Sequence
<220> FEATURE:
<223> OTHER INFORMATION: m4001-m2

<400> SEQUENCE: 156

```
Glu Ala Gly Ile Thr Gly Thr Trp Tyr Asn Gln Leu Gly Ser Thr Phe
1               5                   10                  15
```

Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Arg Asn Ala Gly Phe Ser Thr Leu Val
                100                 105                 110

Gly His Asp Thr Phe Thr Lys Val Lys Pro Ser Ala Ala Ser
            115                 120                 125

<210> SEQ ID NO 157
<211> LENGTH: 126
<212> TYPE: PRT
<213> ORGANISM: Artificial Sequence
<220> FEATURE:
<223> OTHER INFORMATION: m4001-m3

<400> SEQUENCE: 157

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ala Asn Ala Pro Ala Ser Thr Leu Val
                100                 105                 110

Gly His Asp Thr Phe Thr Lys Val Lys Pro Ser Ala Ala Ser
            115                 120                 125

<210> SEQ ID NO 158
<211> LENGTH: 126
<212> TYPE: PRT
<213> ORGANISM: Artificial Sequence
<220> FEATURE:
<223> OTHER INFORMATION: m4001-m5

<400> SEQUENCE: 158

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Ala Asn Ala Met Val Ser Thr Leu Val
            100                 105                 110

Gly His Asp Thr Phe Thr Lys Val Lys Pro Ser Ala Ala Ser
            115                 120                 125

<210> SEQ ID NO 159
<211> LENGTH: 126
<212> TYPE: PRT
<213> ORGANISM: Artificial Sequence
<220> FEATURE:
<223> OTHER INFORMATION: m4001-m13

<400> SEQUENCE: 159

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
            35                  40                  45

Ser Ala Pro Ala Thr Asp Gly Ser Gly Thr Ala Leu Gly Trp Thr Val
            50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Gln Asn Ala Ser Ala Ser Thr Leu Val
            100                 105                 110

Gly His Asp Thr Phe Thr Lys Val Lys Pro Ser Ala Ala Ser
            115                 120                 125

<210> SEQ ID NO 160
<211> LENGTH: 126
<212> TYPE: PRT
<213> ORGANISM: Artificial Sequence
<220> FEATURE:
<223> OTHER INFORMATION: m4001-m14

<400> SEQUENCE: 160

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
            35                  40                  45

Ser Ala Pro Ala Thr Asp Gly Ser Gly Thr Ala Leu Gly Trp Thr Val
            50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Ala Asn Ala Gly Phe Ser Thr Leu Val
            100                 105                 110

Gly His Asp Thr Phe Thr Lys Val Lys Pro Ser Ala Ala Ser
            115                 120                 125

```
<210> SEQ ID NO 161
<211> LENGTH: 126
<212> TYPE: PRT
<213> ORGANISM: Artificial Sequence
<220> FEATURE:
<223> OTHER INFORMATION: m4001-m24

<400> SEQUENCE: 161

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Gln Asn Ala Met Val Ser Thr Leu Val
            100                 105                 110

Gly His Asp Thr Phe Thr Lys Val Lys Pro Ser Ala Ala Ser
        115                 120                 125

<210> SEQ ID NO 162
<211> LENGTH: 126
<212> TYPE: PRT
<213> ORGANISM: Artificial Sequence
<220> FEATURE:
<223> OTHER INFORMATION: m4001-m4

<400> SEQUENCE: 162

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Asn Asn Ala Gly Tyr Ser Thr Leu Val
            100                 105                 110

Gly His Asp Thr Phe Thr Lys Val Lys Pro Ser Ala Ala Ser
        115                 120                 125

<210> SEQ ID NO 163
<211> LENGTH: 126
<212> TYPE: PRT
<213> ORGANISM: Artificial Sequence
<220> FEATURE:
<223> OTHER INFORMATION: m4001-m6

<400> SEQUENCE: 163

Glu Ala Gly Ile Thr Gly Thr Trp Tyr Asn Gln Leu Gly Ser Thr Phe
1               5                   10                  15
```

```
Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ala Asn Ala Ala Val Ser Thr Leu Val
             100                 105                 110

Gly His Asp Thr Phe Thr Lys Val Lys Pro Ser Ala Ala Ser
             115                 120                 125

<210> SEQ ID NO 164
<211> LENGTH: 126
<212> TYPE: PRT
<213> ORGANISM: Artificial Sequence
<220> FEATURE:
<223> OTHER INFORMATION: m4001-m7

<400> SEQUENCE: 164

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ser Asn Ala Met Ile Ser Thr Leu Val
             100                 105                 110

Gly His Asp Thr Phe Thr Lys Val Lys Pro Ser Ala Ala Ser
             115                 120                 125

<210> SEQ ID NO 165
<211> LENGTH: 126
<212> TYPE: PRT
<213> ORGANISM: Artificial Sequence
<220> FEATURE:
<223> OTHER INFORMATION: m4001-m10

<400> SEQUENCE: 165

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
         20                  25                  30

Gly Arg Gly Asn Ala Glu Cys Arg Tyr Val Leu Thr Gly Arg Tyr Asp
         35                  40                  45

Ser Ala Pro Ala Thr Asp Gly Ser Gly Thr Ala Leu Gly Trp Thr Val
         50                  55                  60

Ala Trp Lys Asn Asn Tyr Arg Asn Ala His Ser Ala Thr Thr Trp Ser
```

```
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Asn Ala Gly Tyr Ser Thr Leu Val
            100                 105                 110

Gly His Asp Thr Phe Thr Lys Val Lys Pro Ser Ala Ala Ser
        115                 120                 125

<210> SEQ ID NO 166
<211> LENGTH: 126
<212> TYPE: PRT
<213> ORGANISM: Artificial Sequence
<220> FEATURE:
<223> OTHER INFORMATION: m4001-m15

<400> SEQUENCE: 166

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ser Asn Ala Met Ala Ser Thr Leu Val
            100                 105                 110

Gly His Asp Thr Phe Thr Lys Val Lys Pro Ser Ala Ala Ser
        115                 120                 125

<210> SEQ ID NO 167
<211> LENGTH: 126
<212> TYPE: PRT
<213> ORGANISM: Artificial Sequence
<220> FEATURE:
<223> OTHER INFORMATION: m4001-m23

<400> SEQUENCE: 167

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Gln Asn Ala Val Ala Ser Thr Leu Val
            100                 105                 110

Gly His Asp Thr Phe Thr Lys Val Lys Pro Ser Ala Ala Ser
        115                 120                 125
```

<210> SEQ ID NO 168
<211> LENGTH: 126
<212> TYPE: PRT
<213> ORGANISM: Artificial Sequence
<220> FEATURE:
<223> OTHER INFORMATION: m4001-m17

<400> SEQUENCE: 168

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Tyr Met Ser Thr Leu Val
            100                 105                 110

Gly His Asp Thr Phe Thr Lys Val Lys Pro Ser Ala Ala Ser
        115                 120                 125

<210> SEQ ID NO 169
<211> LENGTH: 126
<212> TYPE: PRT
<213> ORGANISM: Artificial Sequence
<220> FEATURE:
<223> OTHER INFORMATION: m4001-m12

<400> SEQUENCE: 169

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ala Cys
            20                  25                  30

Gly Arg Gly Asn Ala Glu Cys Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Leu Asn Ala Trp Gly Ser Thr Leu Val
            100                 105                 110

Gly His Asp Thr Phe Thr Lys Val Lys Pro Ser Ala Ala Ser
        115                 120                 125

<210> SEQ ID NO 170
<211> LENGTH: 126
<212> TYPE: PRT
<213> ORGANISM: Artificial Sequence
<220> FEATURE:
<223> OTHER INFORMATION: m4001-m20

<400> SEQUENCE: 170

Glu Ala Gly Ile Thr Gly Thr Trp Tyr Asn Gln Leu Gly Ser Thr Phe

```
                1               5                  10                 15
Ile Val Thr Ala Gly Ala Asp Gly Ala Leu Thr Gly Thr Tyr Ala Cys
            20                  25                 30

Gly Arg Gly Asn Ala Glu Cys Arg Tyr Val Leu Thr Gly Arg Tyr Asp
            35                  40                 45

Ser Ala Pro Ala Thr Asp Gly Ser Gly Thr Ala Leu Gly Trp Thr Val
            50                  55                 60

Ala Trp Lys Asn Tyr Arg Asn Ala His Ser Ala Thr Thr Trp Ser
65                  70                  75                      80

Gly Gln Tyr Val Gly Gly Ala Glu Ala Arg Ile Asn Thr Gln Trp Leu
            85                  90                 95

Leu Thr Ser Gly Thr Thr Glu His Asn Ala Ser Met Ser Thr Leu Val
            100                 105                110

Gly His Asp Thr Phe Thr Lys Val Lys Pro Ser Ala Ala Ser
            115                 120                125
```

<210> SEQ ID NO 171
<211> LENGTH: 126
<212> TYPE: PRT
<213> ORGANISM: Artificial Sequence
<220> FEATURE:
<223> OTHER INFORMATION: mutein 1 m101

<400> SEQUENCE: 171

```
Glu Ala Gly Ile Thr Gly Thr Trp Tyr Asn Gln Leu Gly Ser Thr Phe
1               5                   10                 15

Ile Val Thr Ala Gly Ala Asp Gly Ala Leu Thr Gly Thr Tyr Val Thr
            20                  25                 30

Ala Arg Gly Asn Ala Glu Ser Arg Tyr Val Leu Thr Gly Arg Tyr Asp
            35                  40                 45

Ser Ala Pro Ala Thr Asp Gly Ser Gly Thr Ala Leu Gly Trp Thr Val
            50                  55                 60

Ala Trp Lys Asn Asn Tyr Arg Asn Ala His Ser Ala Thr Thr Trp Ser
65                  70                  75                      80

Gly Gln Tyr Val Gly Gly Ala Glu Ala Arg Ile Asn Thr Gln Trp Leu
            85                  90                 95

Leu Thr Ser Gly Thr Thr Glu Tyr Asn Ala Phe Leu Ser Thr Leu Val
            100                 105                110

Gly His Asp Thr Phe Thr Lys Val Lys Pro Ser Ala Ala Ser
            115                 120                125
```

<210> SEQ ID NO 172
<211> LENGTH: 126
<212> TYPE: PRT
<213> ORGANISM: Artificial Sequence
<220> FEATURE:
<223> OTHER INFORMATION: mutein 1 m106

<400> SEQUENCE: 172

```
Glu Ala Gly Ile Thr Gly Thr Trp Tyr Asn Gln Leu Gly Ser Thr Phe
1               5                   10                 15

Ile Val Thr Ala Gly Ala Asp Gly Ala Leu Thr Gly Thr Tyr Val Thr
            20                  25                 30

Ala Arg Gly Asn Ala Glu Ser Arg Tyr Val Leu Thr Gly Arg Tyr Asp
            35                  40                 45

Ser Ala Pro Ala Thr Asp Gly Ser Gly Thr Ala Leu Gly Trp Thr Val
            50                  55                 60
```

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Phe Asn Ala Phe Leu Ser Thr Leu Val
            100                 105                 110

Gly His Asp Thr Phe Thr Lys Val Lys Pro Ser Ala Ala Ser
        115                 120                 125

<210> SEQ ID NO 173
<211> LENGTH: 126
<212> TYPE: PRT
<213> ORGANISM: Artificial Sequence
<220> FEATURE:
<223> OTHER INFORMATION: mutein 1 m111

<400> SEQUENCE: 173

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Leu Trp Ser Thr Leu Val
            100                 105                 110

Gly His Asp Thr Phe Thr Lys Val Lys Pro Ser Ala Ala Ser
        115                 120                 125

<210> SEQ ID NO 174
<211> LENGTH: 126
<212> TYPE: PRT
<213> ORGANISM: Artificial Sequence
<220> FEATURE:
<223> OTHER INFORMATION: mutein 1 m100

<400> SEQUENCE: 174

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Phe Asn Ala Tyr Ile Ser Thr Leu Val
            100                 105                 110

Gly His Asp Thr Phe Thr Lys Val Lys Pro Ser Ala Ala Ser
        115                 120                 125

<210> SEQ ID NO 175
<211> LENGTH: 126
<212> TYPE: PRT
<213> ORGANISM: Artificial Sequence
<220> FEATURE:
<223> OTHER INFORMATION: mutein 1 m110

<400> SEQUENCE: 175

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Tyr Leu Ser Thr Leu Val
            100                 105                 110

Gly His Asp Thr Phe Thr Lys Val Lys Pro Ser Ala Ala Ser
        115                 120                 125
```

<210> SEQ ID NO 176
<211> LENGTH: 126
<212> TYPE: PRT
<213> ORGANISM: Artificial Sequence
<220> FEATURE:
<223> OTHER INFORMATION: mutein 1 m104

<400> SEQUENCE: 176

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Tyr Asn Ala Tyr Gln Ser Thr Leu Val
            100                 105                 110

Gly His Asp Thr Phe Thr Lys Val Lys Pro Ser Ala Ala Ser
        115                 120                 125
```

<210> SEQ ID NO 177
<211> LENGTH: 126
<212> TYPE: PRT
<213> ORGANISM: Artificial Sequence
<220> FEATURE:
<223> OTHER INFORMATION: mutein 1 m108

<400> SEQUENCE: 177

-continued

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Phe Asn Ala Ile Trp Ser Thr Leu Val
            100                 105                 110

Gly His Asp Thr Phe Thr Lys Val Lys Pro Ser Ala Ala Ser
            115                 120                 125

<210> SEQ ID NO 178
<211> LENGTH: 124
<212> TYPE: PRT
<213> ORGANISM: Artificial Sequence
<220> FEATURE:
<223> OTHER INFORMATION: mutein 1 m207

<400> SEQUENCE: 178

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
            85                  90                  95

Leu Thr Ser Gly Thr Thr Glu Thr Trp Leu Ser Thr Leu Val Gly His
            100                 105                 110

Asp Thr Phe Thr Lys Val Lys Pro Ser Ala Ala Ser
            115                 120

<210> SEQ ID NO 179
<211> LENGTH: 124
<212> TYPE: PRT
<213> ORGANISM: Artificial Sequence
<220> FEATURE:
<223> OTHER INFORMATION: mutein 1 m212

<400> SEQUENCE: 179

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Trp Leu Ser Thr Leu Val Gly His
            100                 105                 110

Asp Thr Phe Thr Lys Val Lys Pro Ser Ala Ala Ser
        115                 120

<210> SEQ ID NO 180
<211> LENGTH: 124
<212> TYPE: PRT
<213> ORGANISM: Artificial Sequence
<220> FEATURE:
<223> OTHER INFORMATION: mutein 1 m202

<400> SEQUENCE: 180

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ile Trp Arg Ser Thr Leu Val Gly His
            100                 105                 110

Asp Thr Phe Thr Lys Val Lys Pro Ser Ala Ala Ser
        115                 120

<210> SEQ ID NO 181
<211> LENGTH: 124
<212> TYPE: PRT
<213> ORGANISM: Artificial Sequence
<220> FEATURE:
<223> OTHER INFORMATION: mutein 1 m204

<400> SEQUENCE: 181

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Trp Thr Ser Thr Leu Val Gly His
            100                 105                 110

Asp Thr Phe Thr Lys Val Lys Pro Ser Ala Ala Ser

<210> SEQ ID NO 182
<211> LENGTH: 124
<212> TYPE: PRT
<213> ORGANISM: Artificial Sequence
<220> FEATURE:
<223> OTHER INFORMATION: mutein 1 m206

<400> SEQUENCE: 182

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Thr Trp Arg Ser Thr Leu Val Gly His
            100                 105                 110

Asp Thr Phe Thr Lys Val Lys Pro Ser Ala Ala Ser
        115                 120

<210> SEQ ID NO 183
<211> LENGTH: 124
<212> TYPE: PRT
<213> ORGANISM: Artificial Sequence
<220> FEATURE:
<223> OTHER INFORMATION: mutein 1 m208

<400> SEQUENCE: 183

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Trp Arg Ser Thr Leu Val Gly His
            100                 105                 110

Asp Thr Phe Thr Lys Val Lys Pro Ser Ala Ala Ser
        115                 120

<210> SEQ ID NO 184
<211> LENGTH: 124
<212> TYPE: PRT
<213> ORGANISM: Artificial Sequence
<220> FEATURE:
<223> OTHER INFORMATION: mutein 1 m203

<400> SEQUENCE: 184

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Arg Trp Ser Ser Thr Leu Val Gly His
            100                 105                 110

Asp Thr Phe Thr Lys Val Lys Pro Ser Ala Ala Ser
            115                 120

<210> SEQ ID NO 185
<211> LENGTH: 124
<212> TYPE: PRT
<213> ORGANISM: Artificial Sequence
<220> FEATURE:
<223> OTHER INFORMATION: mutein 1 m209

<400> SEQUENCE: 185

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Asn Trp Arg Ser Thr Leu Val Gly His
            100                 105                 110

Asp Thr Phe Thr Lys Val Lys Pro Ser Ala Ala Ser
            115                 120

<210> SEQ ID NO 186
<211> LENGTH: 124
<212> TYPE: PRT
<213> ORGANISM: Artificial Sequence
<220> FEATURE:
<223> OTHER INFORMATION: mutein 1 m200

<400> SEQUENCE: 186

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val

```
                50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Lys Trp Ser Ser Thr Leu Val Gly His
            100                 105                 110

Asp Thr Phe Thr Lys Val Lys Pro Ser Ala Ala Ser
        115                 120
```

<210> SEQ ID NO 187
<211> LENGTH: 124
<212> TYPE: PRT
<213> ORGANISM: Artificial Sequence
<220> FEATURE:
<223> OTHER INFORMATION: mutein 1 m201

<400> SEQUENCE: 187

```
Glu Ala Gly Ile Thr Gly Thr Trp Tyr Asn Gln Leu Gly Ser Thr Phe
  1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
             35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ser Val Phe Ser Thr Leu Val Gly His
            100                 105                 110

Asp Thr Phe Thr Lys Val Lys Pro Ser Ala Ala Ser
        115                 120
```

<210> SEQ ID NO 188
<211> LENGTH: 124
<212> TYPE: PRT
<213> ORGANISM: Artificial Sequence
<220> FEATURE:
<223> OTHER INFORMATION: mutein 1 m211

<400> SEQUENCE: 188

```
Glu Ala Gly Ile Thr Gly Thr Trp Tyr Asn Gln Leu Gly Ser Thr Phe
  1               5                  10                  15

Ile Val Thr Ala Gly Ala Asp Gly Ala Leu Thr Gly Thr Tyr Val Thr
                 20                  25                  30

Ala Arg Gly Asn Ala Glu Ser Arg Tyr Val Leu Thr Gly Arg Tyr Asp
             35                  40                  45

Ser Ala Pro Ala Thr Asp Gly Ser Gly Thr Ala Leu Gly Trp Thr Val
 50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Lys Trp Thr Ser Thr Leu Val Gly His
            100                 105                 110
```

-continued

```
Asp Thr Phe Thr Lys Val Lys Pro Ser Ala Ala Ser
        115                 120

<210> SEQ ID NO 189
<211> LENGTH: 124
<212> TYPE: PRT
<213> ORGANISM: Artificial Sequence
<220> FEATURE:
<223> OTHER INFORMATION: mutein 1 m300

<400> SEQUENCE: 189

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Trp Tyr Ser Thr Leu Val Gly His
            100                 105                 110

Asp Thr Phe Thr Lys Val Lys Pro Ser Ala Ala Ser
        115                 120

<210> SEQ ID NO 190
<211> LENGTH: 124
<212> TYPE: PRT
<213> ORGANISM: Artificial Sequence
<220> FEATURE:
<223> OTHER INFORMATION: mutein 1 m301

<400> SEQUENCE: 190

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Trp Met Ser Thr Leu Val Gly His
            100                 105                 110

Asp Thr Phe Thr Lys Val Lys Pro Ser Ala Ala Ser
        115                 120

<210> SEQ ID NO 191
<211> LENGTH: 124
<212> TYPE: PRT
<213> ORGANISM: Artificial Sequence
<220> FEATURE:
<223> OTHER INFORMATION: mutein 1 m302
```

<400> SEQUENCE: 191

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu His Trp Tyr Ser Thr Leu Val Gly His
            100                 105                 110

Asp Thr Phe Thr Lys Val Lys Pro Ser Ala Ala Ser
        115                 120

<210> SEQ ID NO 192
<211> LENGTH: 124
<212> TYPE: PRT
<213> ORGANISM: Artificial Sequence
<220> FEATURE:
<223> OTHER INFORMATION: mutein 1 m303

<400> SEQUENCE: 192

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Trp Tyr Ser Thr Leu Val Gly His
            100                 105                 110

Asp Thr Phe Thr Lys Val Lys Pro Ser Ala Ala Ser
        115                 120

<210> SEQ ID NO 193
<211> LENGTH: 124
<212> TYPE: PRT
<213> ORGANISM: Artificial Sequence
<220> FEATURE:
<223> OTHER INFORMATION: mutein 1 m304

<400> SEQUENCE: 193

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Gln Trp Tyr Ser Thr Leu Val Gly His
                100                 105                 110

Asp Thr Phe Thr Lys Val Lys Pro Ser Ala Ala Ser
            115                 120

<210> SEQ ID NO 194
<211> LENGTH: 126
<212> TYPE: PRT
<213> ORGANISM: Artificial Sequence
<220> FEATURE:
<223> OTHER INFORMATION: mutein m1-9

<400> SEQUENCE: 194

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
                100                 105                 110

Gly His Asp Thr Phe Thr Lys Val Lys Pro Ser Ala Ala Ser
            115                 120                 125

<210> SEQ ID NO 195
<211> LENGTH: 8
<212> TYPE: PRT
<213> ORGANISM: Artificial Sequence
<220> FEATURE:
<223> OTHER INFORMATION: loop of the amino acids 114 to 121 of
      streptavidin

<400> SEQUENCE: 195

Thr Thr Glu Ala Asn Ala Trp Lys
1               5

<210> SEQ ID NO 196
<211> LENGTH: 7
<212> TYPE: PRT
<213> ORGANISM: Artificial Sequence
<220> FEATURE:
<223> OTHER INFORMATION: loop region of amino acids 115 to 121 of
      streptavidin

<400> SEQUENCE: 196

Thr Glu Ala Asn Ala Trp Lys
1               5

<210> SEQ ID NO 197

```
<211> LENGTH: 14
<212> TYPE: PRT
<213> ORGANISM: Artificial Sequence
<220> FEATURE:
<223> OTHER INFORMATION: mutein

<400> SEQUENCE: 197

His Pro Tyr Phe Tyr Ala Pro Glu Leu Leu Phe Phe Ala Lys
1               5                   10

<210> SEQ ID NO 198

<400> SEQUENCE: 198

000

<210> SEQ ID NO 199
<211> LENGTH: 5
<212> TYPE: PRT
<213> ORGANISM: Artificial Sequence
<220> FEATURE:
<223> OTHER INFORMATION: motif1
<220> FEATURE:
<221> NAME/KEY: MISC_FEATURE
<222> LOCATION: (1)..(1)
<223> OTHER INFORMATION: Xaa is Glu, Asp, Arg, His, Asn, Gln, Thr, Ser,
      Leu, Met
<220> FEATURE:
<221> NAME/KEY: MISC_FEATURE
<222> LOCATION: (5)..(5)
<223> OTHER INFORMATION: Xaa is Phe, Tyr, Met

<400> SEQUENCE: 199

Xaa Asn Ala Gly Xaa
1               5

<210> SEQ ID NO 200
<211> LENGTH: 5
<212> TYPE: PRT
<213> ORGANISM: Artificial Sequence
<220> FEATURE:
<223> OTHER INFORMATION: motif2
<220> FEATURE:
<221> NAME/KEY: MISC_FEATURE
<222> LOCATION: (1)..(1)
<223> OTHER INFORMATION: Xaa is Tyr, Phe, Arg, Trp, Gln
<220> FEATURE:
<221> NAME/KEY: MISC_FEATURE
<222> LOCATION: (4)..(4)
<223> OTHER INFORMATION: Xaa is Tyr, Phe, Leu, Ile, Met
<220> FEATURE:
<221> NAME/KEY: MISC_FEATURE
<222> LOCATION: (5)..(5)
<223> OTHER INFORMATION: Xaa is Leu, Ile, Met, Gln, Gly, Trp, Ser, Ala,
      Val

<400> SEQUENCE: 200

Xaa Asn Ala Xaa Xaa
1               5

<210> SEQ ID NO 201
<211> LENGTH: 5
<212> TYPE: PRT
<213> ORGANISM: Artificial Sequence
<220> FEATURE:
<223> OTHER INFORMATION: motif3
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
```

```
<222> LOCATION: (2)..(2)
<223> OTHER INFORMATION: Xaa is an amino acid deletion
<220> FEATURE:
<221> NAME/KEY: MISC_FEATURE
<222> LOCATION: (3)..(3)
<223> OTHER INFORMATION: Xaa is an amino acid deletion
<220> FEATURE:
<221> NAME/KEY: MISC_FEATURE
<222> LOCATION: (4)..(4)
<223> OTHER INFORMATION: Xaa is Trp or Val
<220> FEATURE:
<221> NAME/KEY: MISC_FEATURE
<222> LOCATION: (5)..(5)
<223> OTHER INFORMATION: Xaa is any amino acid

<400> SEQUENCE: 201

Xaa Xaa Xaa Xaa Xaa
1               5

<210> SEQ ID NO 202
<211> LENGTH: 5
<212> TYPE: PRT
<213> ORGANISM: Artificial Sequence
<220> FEATURE:
<223> OTHER INFORMATION: Motif2(Figure 2B)
<220> FEATURE:
<221> NAME/KEY: MISC_FEATURE
<222> LOCATION: (1)..(1)
<223> OTHER INFORMATION: Xaa is any amino acid or amino acid deletion
<220> FEATURE:
<221> NAME/KEY: MISC_FEATURE
<222> LOCATION: (2)..(3)
<223> OTHER INFORMATION: Xaa is an amino acid deletion
<220> FEATURE:
<221> NAME/KEY: MISC_FEATURE
<222> LOCATION: (4)..(5)
<223> OTHER INFORMATION: Xaa is any amino acid or amino acid deletion

<400> SEQUENCE: 202

Xaa Xaa Xaa Xaa Xaa
1               5

<210> SEQ ID NO 203
<211> LENGTH: 9
<212> TYPE: PRT
<213> ORGANISM: Artificial Sequence
<220> FEATURE:
<223> OTHER INFORMATION: Library 1
<220> FEATURE:
<221> NAME/KEY: MISC_FEATURE
<222> LOCATION: (1)..(2)
<223> OTHER INFORMATION: Xaa is any amino acid or an amino acid deletion
<220> FEATURE:
<221> NAME/KEY: misc_feature
<222> LOCATION: (9)..(9)
<223> OTHER INFORMATION: Xaa can be any naturally occurring amino acid

<400> SEQUENCE: 203

Xaa Xaa Ala Arg Gly Asn Ala Glu Xaa
1               5

<210> SEQ ID NO 204
<211> LENGTH: 9
<212> TYPE: PRT
<213> ORGANISM: Artificial Sequence
<220> FEATURE:
<223> OTHER INFORMATION: Library 2
<220> FEATURE:
<221> NAME/KEY: MISC_FEATURE
<222> LOCATION: (1)..(1)
<223> OTHER INFORMATION: Xaa is Ala or Gly
<220> FEATURE:
<221> NAME/KEY: MISC_FEATURE
```

```
<222> LOCATION: (3)..(4)
<223> OTHER INFORMATION: Xaa is any amino acid or an amino acid deletion

<400> SEQUENCE: 204

Xaa Cys Xaa Xaa Gly Asn Ala Glu Cys
1               5

<210> SEQ ID NO 205
<211> LENGTH: 9
<212> TYPE: PRT
<213> ORGANISM: Artificial Sequence
<220> FEATURE:
<223> OTHER INFORMATION: Library 2 wildtype

<400> SEQUENCE: 205

Glu Ser Ala Val Gly Asn Ala Glu Ser
1               5

<210> SEQ ID NO 206
<211> LENGTH: 5
<212> TYPE: PRT
<213> ORGANISM: Artificial Sequence
<220> FEATURE:
<223> OTHER INFORMATION: Library 3
<220> FEATURE:
<221> NAME/KEY: MISC_FEATURE
<222> LOCATION: (1)..(1)
<223> OTHER INFORMATION: Xaa is any amno acid or an amino acid deletion
<220> FEATURE:
<221> NAME/KEY: MISC_FEATURE
<222> LOCATION: (4)..(5)
<223> OTHER INFORMATION: Xaa is any amno acid or an amino acid deletion

<400> SEQUENCE: 206

Xaa Asn Ala Xaa Xaa
1               5

<210> SEQ ID NO 207
<211> LENGTH: 5
<212> TYPE: PRT
<213> ORGANISM: Artificial Sequence
<220> FEATURE:
<223> OTHER INFORMATION: Wt (Library 2), mutein "1(Library 2), Wt
      (Library 4), m4001 (Library 4), Wt (Library 5), mutein "1"
      (Library 5), Wt (Library 6), mutein "1" (Library 6), Wt (Library
      7), mutein "1" (Library 7)

<400> SEQUENCE: 207

Ala Asn Ala Trp Lys
1               5

<210> SEQ ID NO 208
<211> LENGTH: 5
<212> TYPE: PRT
<213> ORGANISM: Artificial Sequence
<220> FEATURE:
<223> OTHER INFORMATION: Library 4
<220> FEATURE:
<221> NAME/KEY: MISC_FEATURE
<222> LOCATION: (1)..(1)
<223> OTHER INFORMATION: Xaa is any amino acid or deletion
<220> FEATURE:
<221> NAME/KEY: MISC_FEATURE
<222> LOCATION: (4)..(5)
<223> OTHER INFORMATION: Xaa is any amino acid or deletion

<400> SEQUENCE: 208

Xaa Asn Ala Xaa Xaa
1               5
```

```
<210> SEQ ID NO 209
<211> LENGTH: 5
<212> TYPE: PRT
<213> ORGANISM: Artificial Sequence
<220> FEATURE:
<223> OTHER INFORMATION: Library 5
<220> FEATURE:
<221> NAME/KEY: misc_feature
<222> LOCATION: (1)..(1)
<223> OTHER INFORMATION: Xaa is Phe/Tyr
<220> FEATURE:
<221> NAME/KEY: misc_feature
<222> LOCATION: (4)..(5)
<223> OTHER INFORMATION: Xaa is any amino acid or amino acid deletion

<400> SEQUENCE: 209

Xaa Asn Ala Xaa Xaa
1               5

<210> SEQ ID NO 210
<211> LENGTH: 5
<212> TYPE: PRT
<213> ORGANISM: Artificial Sequence
<220> FEATURE:
<223> OTHER INFORMATION: Library 6
<220> FEATURE:
<221> NAME/KEY: misc_feature
<222> LOCATION: (1)..(1)
<223> OTHER INFORMATION: Xaa is any amino acid or amino acid deletion
<220> FEATURE:
<221> NAME/KEY: misc_feature
<222> LOCATION: (2)..(3)
<223> OTHER INFORMATION: Xaa is an amino acid deletion
<220> FEATURE:
<221> NAME/KEY: misc_feature
<222> LOCATION: (4)..(5)
<223> OTHER INFORMATION: Xaa is any amino acid or amino acid deletion

<400> SEQUENCE: 210

Xaa Xaa Xaa Xaa Xaa
1               5

<210> SEQ ID NO 211
<211> LENGTH: 5
<212> TYPE: PRT
<213> ORGANISM: Artificial Sequence
<220> FEATURE:
<223> OTHER INFORMATION: Library 7
<220> FEATURE:
<221> NAME/KEY: MISC_FEATURE
<222> LOCATION: (1)..(1)
<223> OTHER INFORMATION: Xaa is any amino acid or amino acid deletion
<220> FEATURE:
<221> NAME/KEY: MISC_FEATURE
<222> LOCATION: (2)..(3)
<223> OTHER INFORMATION: Xaa is an amino acid deletion
<220> FEATURE:
<221> NAME/KEY: MISC_FEATURE
<222> LOCATION: (5)..(5)
<223> OTHER INFORMATION: Xaa is any amino acid or amino acid deletion

<400> SEQUENCE: 211

Xaa Xaa Xaa Trp Xaa
1               5

<210> SEQ ID NO 212
<211> LENGTH: 126
<212> TYPE: PRT
<213> ORGANISM: Artificial Sequence
<220> FEATURE:
<223> OTHER INFORMATION: Wt streptavidin amino acid sequence (residues
      14 to 139)
```

```
<400> SEQUENCE: 212

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
            115                 120                 125
```